(12) United States Patent
Wagner et al.

(10) Patent No.: US 9,980,793 B2
(45) Date of Patent: May 29, 2018

(54) ORAL HYGIENE SYSTEM

(71) Applicant: WATER PIK, INC., Fort Collins, CO (US)

(72) Inventors: Robert Wagner, Firestone, CO (US); Kurt M. Taylor, Fort Collins, CO (US); Harold A. Luettgen, Windsor, CO (US); Jeremy James Johnson, Longmont, CO (US)

(73) Assignee: Water Pik, Inc., Fort Collins, CO (US)

( * ) Notice: Subject to any disclaimer, the term of this patent is extended or adjusted under 35 U.S.C. 154(b) by 723 days.

(21) Appl. No.: 14/590,751

(22) Filed: Jan. 6, 2015

(65) Prior Publication Data

US 2015/0182319 A1    Jul. 2, 2015

Related U.S. Application Data

(63) Continuation-in-part of application No. 14/555,339, filed on Nov. 26, 2014.
(Continued)

(51) Int. Cl.
*A61C 17/02* (2006.01)
*A61C 17/20* (2006.01)
(Continued)

(52) U.S. Cl.
CPC ...... *A61C 17/0202* (2013.01); *A61C 17/0205* (2013.01); *A61C 17/20* (2013.01);
(Continued)

(58) Field of Classification Search
CPC . A61C 17/0202; A61C 17/34; A61C 17/0205; A61C 17/20; A61C 17/224; A61C 1/0092
See application file for complete search history.

(56) References Cited

U.S. PATENT DOCUMENTS

| 555,588 A | 3/1896 | Spencer |
| 1,278,225 A | 9/1918 | Schamberg |

(Continued)

FOREIGN PATENT DOCUMENTS

| CA | 851479 | 9/1970 |
| CH | 655237 | 4/1987 |

(Continued)

OTHER PUBLICATIONS

US RE27,274, 01/1972, Mattingly (withdrawn)
(Continued)

*Primary Examiner* — Quang D Thanh
(74) *Attorney, Agent, or Firm* — Dorsey & Whitney LLP

(57) ABSTRACT

An apparatus for oral hygiene is disclosed herein. The apparatus includes a base unit containing a reservoir, an oral irrigation handle, a sonic toothbrush, and an accessory container. The apparatus may include a pump, which may move pressurized water from a reservoir to a tip in fluid communication with the pump. The apparatus contains a drive mechanism in a gear housing that is continually drained by one or more apertures in the base. The base may include a plurality of footings that elevate the base unit above a surface supporting the base unit. The oral irrigation handle includes a pause switch that translates longitude motion into rotational motion to close a valve.

19 Claims, 39 Drawing Sheets

Related U.S. Application Data

(60) Provisional application No. 61/909,738, filed on Nov. 27, 2013, provisional application No. 61/924,053, filed on Jan. 6, 2014.

(51) Int. Cl.
*A61C 17/22* (2006.01)
*A61C 17/34* (2006.01)
*A61C 1/00* (2006.01)

(52) U.S. Cl.
CPC ............ *A61C 17/224* (2013.01); *A61C 17/34* (2013.01); *A61C 1/0092* (2013.01)

(56) References Cited

U.S. PATENT DOCUMENTS

| | | |
|---|---|---|
| 1,452,258 A | 4/1923 | Smith |
| 1,464,419 A | 8/1923 | Gill |
| 1,480,310 A | 1/1924 | Smith |
| 1,498,267 A | 6/1924 | Hachman |
| 1,602,742 A | 10/1926 | Bennet |
| 1,650,686 A | 11/1927 | Binks |
| 1,669,889 A | 5/1928 | Andrews et al. |
| 1,681,320 A | 8/1928 | Bergl et al. |
| 1,933,454 A | 10/1933 | Sidney |
| 1,940,111 A | 12/1933 | Austin |
| D93,019 S | 8/1934 | Hose |
| 1,977,782 A | 10/1934 | Roy |
| 2,107,686 A | 2/1938 | Bramsen et al. |
| D159,872 S | 8/1950 | Skold |
| 2,531,730 A | 11/1950 | Henderson |
| 2,595,666 A | 5/1952 | Hutson |
| 2,669,233 A | 2/1954 | Friend |
| 2,709,227 A | 5/1955 | Foley et al. |
| 2,733,713 A | 2/1956 | Kabnick |
| 2,783,919 A | 3/1957 | Ansell |
| 2,794,437 A | 6/1957 | Tash |
| 2,870,932 A | 1/1959 | Davis |
| 2,984,452 A | 6/1961 | Hooper |
| 3,089,490 A | 5/1963 | Goldberg |
| 3,096,913 A | 7/1963 | Jousson |
| 3,144,867 A | 8/1964 | Trupp et al. |
| D202,041 S | 8/1965 | Burzlaff |
| 3,209,956 A | 10/1965 | McKenzie |
| 3,216,619 A | 11/1965 | Richards et al. |
| 3,225,759 A | 12/1965 | Drapen et al. |
| 3,227,158 A | 1/1966 | Mattingly |
| 3,266,623 A | 8/1966 | Poferl |
| 3,297,558 A | 1/1967 | Hillquist |
| D208,778 S | 10/1967 | Koch |
| D209,202 S | 11/1967 | Fulton et al. |
| D209,203 S | 11/1967 | Mattingly et al. |
| D209,204 S | 11/1967 | St. Clair et al. |
| D209,395 S | 11/1967 | Gilbert |
| D210,018 S | 1/1968 | Mattingly et al. |
| D210,019 S | 1/1968 | Johnson et al. |
| 3,370,214 A | 2/1968 | Aymar |
| 3,391,696 A | 7/1968 | Woodward |
| 3,393,673 A | 7/1968 | Mattingly et al. |
| 3,400,999 A | 9/1968 | Goldstein |
| 3,418,552 A | 12/1968 | Holmes |
| 3,420,228 A | 1/1969 | Kalbfeld |
| 3,425,410 A | 2/1969 | Cammack |
| 3,453,969 A | 7/1969 | Mattingly |
| 3,465,751 A | 9/1969 | Powers |
| 3,467,083 A | 9/1969 | Mattingly |
| 3,467,286 A | 9/1969 | Ostrowsky |
| D215,920 S | 11/1969 | McCarty et al. |
| 3,487,828 A | 1/1970 | Troy |
| 3,489,268 A | 1/1970 | Meierhoefer |
| 3,495,587 A | 2/1970 | Freedman |
| 3,496,933 A | 2/1970 | Lloyd |
| 3,499,440 A | 3/1970 | Gibbs |
| 3,500,824 A | 3/1970 | Gilbert |
| 3,501,203 A | 3/1970 | Falk |
| 3,502,072 A | 3/1970 | Stillman |
| 3,517,669 A | 6/1970 | Buono et al. |
| D218,270 S | 8/1970 | Soper |
| 3,522,801 A | 8/1970 | Robinson |
| 3,532,221 A | 10/1970 | Kaluhiokalani et al. |
| 3,536,065 A | 10/1970 | Moret |
| 3,537,444 A | 11/1970 | Garn |
| 3,538,950 A | 11/1970 | Porteners |
| 3,547,110 A | 12/1970 | Balamuth |
| 3,561,433 A | 2/1971 | Kovach |
| D220,334 S | 3/1971 | Mackay et al. |
| 3,570,525 A | 3/1971 | Borsum |
| 3,572,375 A | 3/1971 | Rosenberg |
| 3,578,884 A | 5/1971 | Jacobson |
| D220,996 S | 6/1971 | Irons |
| 3,583,609 A | 6/1971 | Oppenheimer |
| 3,590,813 A | 7/1971 | Roszyk |
| 3,608,548 A | 9/1971 | Lewis |
| D222,862 S | 1/1972 | Cook |
| 3,636,947 A | 1/1972 | Balamuth |
| 3,651,576 A | 3/1972 | Massa |
| 3,669,101 A | 6/1972 | Kleiner |
| 3,703,170 A | 11/1972 | Ryckman, Jr. |
| 3,718,974 A | 3/1973 | Buchtel et al. |
| 3,747,595 A | 7/1973 | Grossan |
| 3,768,472 A | 10/1973 | Hodosh et al. |
| 3,771,186 A | 11/1973 | Moret et al. |
| 3,783,364 A | 1/1974 | Gallanis et al. |
| 3,809,506 A | 5/1974 | Malcosky |
| 3,809,977 A | 5/1974 | Balamuth et al. |
| 3,811,432 A | 5/1974 | Moret |
| 3,820,532 A | 6/1974 | Eberhardt et al. |
| 3,827,147 A | 8/1974 | Condon |
| 3,837,166 A | 9/1974 | Hiraoka |
| 3,840,795 A | 10/1974 | Roszyk et al. |
| 3,847,145 A | 11/1974 | Grossan |
| 3,854,209 A | 12/1974 | Franklin et al. |
| 3,863,628 A | 2/1975 | Vit |
| 3,871,560 A | 3/1975 | Crippa |
| 3,874,506 A | 4/1975 | Hill et al. |
| 3,911,796 A | 10/1975 | Hull et al. |
| 3,912,125 A | 10/1975 | Acklin |
| 3,943,628 A | 3/1976 | Kronman et al. |
| 3,959,883 A | 6/1976 | Walls et al. |
| 3,973,558 A | 8/1976 | Stouffer et al. |
| 3,977,084 A | 8/1976 | Sloan |
| 4,001,526 A | 1/1977 | Olson |
| 4,004,302 A | 1/1977 | Hori |
| 4,007,739 A | 2/1977 | Bron et al. |
| 4,013,227 A | 3/1977 | Herrera |
| 4,022,114 A | 5/1977 | Hansen, III |
| 4,052,002 A | 10/1977 | Stouffer et al. |
| D246,667 S | 12/1977 | Mackay et al. |
| D246,668 S | 12/1977 | Mackay et al. |
| 4,060,870 A | 12/1977 | Cannarelia |
| 4,075,761 A | 2/1978 | Behne et al. |
| 4,078,558 A | 3/1978 | Woog et al. |
| 4,089,079 A | 5/1978 | Nicholson |
| 4,094,311 A | 6/1978 | Hudson |
| 4,108,167 A | 8/1978 | Hickman et al. |
| 4,108,178 A | 8/1978 | Betush |
| 4,109,650 A | 8/1978 | Peclard |
| 4,122,845 A | 10/1978 | Stouffer et al. |
| 4,133,971 A | 1/1979 | Boyd et al. |
| 4,135,501 A | 1/1979 | Leunissan |
| 4,141,352 A | 2/1979 | Ebner et al. |
| 4,144,646 A | 3/1979 | Takemoto et al. |
| 4,149,315 A | 4/1979 | Page, Jr. et al. |
| 4,154,375 A | 5/1979 | Bippus |
| 4,160,383 A | 7/1979 | Rauschenberger |
| 4,171,572 A | 10/1979 | Nash |
| 4,182,038 A | 1/1980 | Fleer |
| 4,200,235 A | 4/1980 | Monschke |
| 4,201,200 A | 5/1980 | Hubner |
| 4,210,380 A | 7/1980 | Brzostek |
| 4,215,476 A | 8/1980 | Armstrong |
| 4,219,618 A | 8/1980 | Leonard |
| 4,227,878 A | 10/1980 | Lohn |
| 4,229,634 A | 10/1980 | Hickman et al. |

(56) References Cited

U.S. PATENT DOCUMENTS

| | | |
|---|---|---|
| 4,236,889 A | 12/1980 | Wright |
| D258,097 S | 2/1981 | Wistrand |
| 4,248,589 A | 2/1981 | Lewis |
| 4,249,899 A | 2/1981 | Davis |
| 4,257,458 A | 3/1981 | Kondo et al. |
| 4,262,799 A | 4/1981 | Perrett |
| 4,266,934 A | 5/1981 | Pernot |
| 4,276,023 A | 6/1981 | Phillips et al. |
| 4,276,880 A | 7/1981 | Malmin |
| 4,302,186 A | 11/1981 | Cammack et al. |
| 4,303,064 A | 12/1981 | Buffa |
| 4,303,070 A | 12/1981 | Ichikawa et al. |
| 4,306,862 A | 12/1981 | Knox |
| 4,315,741 A | 2/1982 | Reichl |
| 4,319,568 A | 3/1982 | Tregoning |
| 4,331,422 A | 5/1982 | Heyman |
| 4,337,040 A | 6/1982 | Cammack et al. |
| 4,340,365 A | 7/1982 | Pisanu |
| 4,340,368 A | 7/1982 | Lococo |
| D266,117 S | 9/1982 | Oberheim |
| 4,353,694 A | 10/1982 | Pelerin |
| 4,363,626 A | 12/1982 | Schmidt et al. |
| 4,365,376 A | 12/1982 | Oda et al. |
| 4,370,131 A | 1/1983 | Banko |
| 4,374,354 A | 2/1983 | Petrovic et al. |
| 4,382,167 A | 5/1983 | Maruyama et al. |
| 4,382,786 A | 5/1983 | Lohn |
| D270,000 S | 8/1983 | Ketler |
| 4,396,011 A | 8/1983 | Mack et al. |
| 4,412,823 A | 11/1983 | Sakai et al. |
| 4,416,628 A | 11/1983 | Cammack |
| 4,442,830 A * | 4/1984 | Markau ............... A61C 17/02 433/80 |
| 4,442,831 A | 4/1984 | Trenary |
| 4,452,238 A | 6/1984 | Kerr |
| 4,454,866 A | 6/1984 | Fayen |
| 4,512,769 A | 4/1985 | Kozam et al. |
| 4,517,962 A | 5/1985 | Heckele |
| 4,531,912 A | 7/1985 | Schuss et al. |
| 4,531,913 A | 7/1985 | Taguchi |
| 4,534,340 A | 8/1985 | Kerr et al. |
| 4,552,130 A | 11/1985 | Kinoshita |
| 4,561,214 A | 12/1985 | Inoue |
| D283,374 S | 4/1986 | Cheuk-Yiu |
| 4,585,415 A | 4/1986 | Hommann |
| 4,591,777 A | 5/1986 | McCarty et al. |
| 4,592,728 A | 6/1986 | Davis |
| 4,602,906 A | 7/1986 | Grunenfelder |
| 4,607,627 A | 8/1986 | Leber et al. |
| 4,613,074 A | 9/1986 | Schulze |
| 4,619,009 A | 10/1986 | Rosenstatter |
| 4,619,612 A | 10/1986 | Weber et al. |
| 4,629,425 A | 12/1986 | Detsch |
| 4,636,198 A | 1/1987 | Stade |
| 4,642,037 A | 2/1987 | Fritchman |
| 4,644,937 A | 2/1987 | Hommann |
| 4,645,488 A | 2/1987 | Matukas |
| 4,647,831 A | 3/1987 | O'Malley et al. |
| 4,648,838 A | 3/1987 | Schlachter |
| 4,650,475 A | 3/1987 | Smith et al. |
| 4,655,198 A | 4/1987 | Hommann |
| 4,669,453 A | 6/1987 | Atkinson et al. |
| 4,672,953 A | 6/1987 | DiVito |
| 4,673,396 A | 6/1987 | Urbaniak |
| D291,354 S | 8/1987 | Camens |
| 4,716,352 A | 12/1987 | Hurn et al. |
| 4,749,340 A | 6/1988 | Ikeda et al. |
| 4,770,632 A | 9/1988 | Ryder et al. |
| D298,565 S | 11/1988 | Kohler, Jr. et al. |
| 4,783,321 A | 11/1988 | Spence |
| 4,787,845 A | 11/1988 | Valentine |
| 4,787,847 A | 11/1988 | Martin et al. |
| 4,798,292 A | 1/1989 | Hauze |
| 4,803,974 A | 2/1989 | Powell |
| 4,804,364 A | 2/1989 | Dieras et al. |
| 4,810,148 A | 3/1989 | Aisa et al. |
| 4,818,229 A | 4/1989 | Vasile |
| 4,820,152 A | 4/1989 | Warrin et al. |
| 4,821,923 A | 4/1989 | Skorka |
| 4,824,368 A | 4/1989 | Hickman |
| 4,826,431 A | 5/1989 | Fujimura et al. |
| 4,827,551 A | 5/1989 | Maser et al. |
| 4,832,683 A | 5/1989 | Idemoto et al. |
| 4,854,869 A | 8/1989 | Lawhorn |
| 4,861,340 A | 8/1989 | Smith et al. |
| 4,862,876 A | 9/1989 | Lih-Sheng |
| 4,864,918 A | 9/1989 | Martin |
| 4,869,720 A | 9/1989 | Chernack |
| 4,880,382 A | 11/1989 | Moret et al. |
| 4,886,452 A | 12/1989 | Lohn |
| 4,900,252 A | 2/1990 | Liefke et al. |
| 4,902,225 A | 2/1990 | Lohn |
| 4,903,687 A | 2/1990 | Lih-Sheng |
| 4,906,187 A | 3/1990 | Amadera |
| 4,907,744 A | 3/1990 | Jousson |
| 4,915,304 A | 4/1990 | Campani |
| 4,925,450 A | 5/1990 | Imonti et al. |
| 4,928,675 A | 5/1990 | Thornton |
| 4,930,660 A | 6/1990 | Porteous |
| 4,941,459 A | 7/1990 | Mathur |
| 4,950,159 A | 8/1990 | Hansen |
| 4,958,629 A | 9/1990 | Peace et al. |
| 4,958,751 A | 9/1990 | Curtis et al. |
| 4,959,199 A | 9/1990 | Brewer |
| 4,961,698 A | 10/1990 | Vlock |
| 4,966,551 A | 10/1990 | Betush |
| 4,969,874 A | 11/1990 | Michel et al. |
| 4,973,246 A | 11/1990 | Black |
| 4,973,247 A | 11/1990 | Varnes et al. |
| 4,973,250 A | 11/1990 | Milman |
| 4,975,054 A | 12/1990 | Esrock |
| 4,979,503 A | 12/1990 | Chernack |
| 4,979,504 A | 12/1990 | Mills |
| 4,989,590 A | 2/1991 | Baum et al. |
| 4,998,880 A | 3/1991 | Nerli |
| 5,013,241 A | 5/1991 | Von Gutfeld et al. |
| 5,014,884 A | 5/1991 | Wunsch |
| 5,019,054 A | 5/1991 | Clement et al. |
| 5,027,798 A | 7/1991 | Primiano |
| 5,029,576 A | 7/1991 | Evans, Sr. |
| 5,033,617 A | 7/1991 | Hartwein et al. |
| 5,033,961 A | 7/1991 | Kankler et al. |
| D318,918 S | 8/1991 | Hartwein |
| 5,046,486 A | 9/1991 | Grulke et al. |
| 5,049,071 A | 9/1991 | Davis et al. |
| 5,060,825 A | 10/1991 | Palmer et al. |
| 5,061,180 A | 10/1991 | Wiele |
| 5,062,795 A | 11/1991 | Woog |
| 5,064,168 A | 11/1991 | Raines et al. |
| D322,314 S | 12/1991 | Ohbayashi |
| 5,071,346 A | 12/1991 | Domaas |
| 5,082,115 A | 1/1992 | Hutcheson |
| 5,082,443 A | 1/1992 | Lohn |
| 5,085,317 A | 2/1992 | Jensen et al. |
| 5,086,756 A | 2/1992 | Powell |
| 5,095,893 A | 3/1992 | Rawden, Jr. |
| 5,098,291 A | 3/1992 | Curtis et al. |
| 5,098,676 A | 3/1992 | Brooks, Jr. |
| 5,100,319 A | 3/1992 | Baum |
| 5,117,871 A | 6/1992 | Gardner et al. |
| 5,125,835 A | 6/1992 | Young |
| 5,127,831 A | 7/1992 | Bab |
| 5,142,723 A | 9/1992 | Lustig et al. |
| 5,150,841 A | 9/1992 | Silvenis et al. |
| 5,172,810 A | 12/1992 | Brewer |
| 5,173,273 A | 12/1992 | Brewer |
| 5,183,035 A | 2/1993 | Weir |
| 5,197,458 A | 3/1993 | Ito et al. |
| 5,197,460 A | 3/1993 | Ito et al. |
| 5,199,871 A | 4/1993 | Young |
| 5,203,697 A | 4/1993 | Malmin |
| 5,203,769 A | 4/1993 | Clement et al. |
| 5,204,004 A | 4/1993 | Johnston et al. |
| 5,208,933 A | 5/1993 | Lustig et al. |

(56) References Cited

U.S. PATENT DOCUMENTS

| | | |
|---|---|---|
| 5,215,193 A | 6/1993 | Dennis |
| 5,218,956 A | 6/1993 | Handler et al. |
| 5,220,914 A | 6/1993 | Thompson |
| 5,228,646 A | 7/1993 | Raines |
| 5,230,624 A | 7/1993 | Wolf et al. |
| 5,232,687 A | 8/1993 | Geimer |
| 5,235,968 A | 8/1993 | Woog |
| 5,241,714 A | 9/1993 | Barry |
| 5,246,367 A | 9/1993 | Ito et al. |
| 5,252,064 A | 10/1993 | Baum et al. |
| D341,200 S | 11/1993 | Yoshimoto |
| 5,257,933 A | 11/1993 | Jousson |
| 5,261,448 A | 11/1993 | Furuya et al. |
| D341,943 S | 12/1993 | Si-Hoe |
| 5,267,586 A | 12/1993 | Jankavaara |
| 5,269,684 A | 12/1993 | Fischer |
| 5,281,137 A | 1/1994 | Jousson |
| 5,281,139 A | 1/1994 | Frank et al. |
| 5,282,745 A | 2/1994 | Wiltrout et al. |
| 5,286,192 A | 2/1994 | Dixon |
| 5,286,201 A | 2/1994 | Yu |
| 5,295,832 A | 3/1994 | Evans |
| 5,297,962 A | 3/1994 | O'Connor et al. |
| D346,212 S | 4/1994 | Hosl |
| 5,301,381 A | 4/1994 | Klupt |
| 5,302,123 A | 4/1994 | Bechard |
| 5,317,691 A | 5/1994 | Traeger |
| 5,321,865 A | 6/1994 | Kaeser |
| 5,323,770 A | 6/1994 | Ito et al. |
| 5,331,704 A | 7/1994 | Rosen et al. |
| 5,344,317 A | 9/1994 | Pacher et al. |
| 5,346,677 A | 9/1994 | Risk |
| 5,349,896 A | 9/1994 | Delaney |
| D351,892 S | 10/1994 | Wolf et al. |
| 5,360,338 A | 11/1994 | Waggoner |
| 5,368,548 A | 11/1994 | Jousson |
| 5,370,534 A | 12/1994 | Wolf et al. |
| D354,168 S | 1/1995 | Hartwein |
| D354,559 S | 1/1995 | Knute |
| 5,378,149 A | 1/1995 | Stropko |
| 5,380,201 A | 1/1995 | Kawata |
| D356,864 S | 3/1995 | Woog |
| 5,399,089 A | 3/1995 | Eichman et al. |
| D358,883 S | 5/1995 | Vos |
| 5,456,672 A | 10/1995 | Diederich et al. |
| 5,465,445 A | 11/1995 | Yeh |
| 5,467,495 A | 11/1995 | Boland et al. |
| 5,468,148 A | 11/1995 | Ricks |
| 5,470,305 A | 11/1995 | Arnett et al. |
| 5,474,450 A | 12/1995 | Chronister |
| 5,474,451 A | 12/1995 | Dalrymple et al. |
| 5,476,379 A | 12/1995 | Disel |
| 5,484,281 A | 1/1996 | Renow et al. |
| 5,487,877 A | 1/1996 | Choi |
| 5,490,779 A | 2/1996 | Malmin |
| 5,505,916 A | 4/1996 | Berry, Jr. |
| D369,656 S | 5/1996 | Vos |
| D370,125 S | 5/1996 | Craft et al. |
| 5,525,058 A | 6/1996 | Gallant et al. |
| 5,526,841 A | 6/1996 | Detsch et al. |
| 5,540,587 A | 7/1996 | Malmin |
| 5,547,374 A | 8/1996 | Coleman |
| D373,631 S | 9/1996 | Maeda et al. |
| 5,554,014 A | 9/1996 | Becker |
| 5,554,025 A | 9/1996 | Kinsel |
| 5,556,001 A | 9/1996 | Weissman et al. |
| 5,564,629 A | 10/1996 | Weissman et al. |
| D376,893 S | 12/1996 | Gornet |
| D377,091 S | 12/1996 | Scott, Sr. |
| 5,613,259 A | 3/1997 | Craft et al. |
| 5,616,028 A | 4/1997 | Hafele et al. |
| 5,626,472 A | 5/1997 | Pennetta |
| 5,634,791 A | 6/1997 | Matsuura et al. |
| 5,636,987 A | 6/1997 | Serfaty |
| 5,640,735 A | 6/1997 | Manning |
| D382,407 S | 8/1997 | Craft et al. |
| 5,653,591 A | 8/1997 | Loge |
| 5,659,995 A | 8/1997 | Hoffman |
| 5,667,483 A | 9/1997 | Santos |
| D386,576 S | 11/1997 | Wang et al. |
| 5,683,192 A | 11/1997 | Kilfoil |
| 5,685,829 A | 11/1997 | Allen |
| 5,685,851 A | 11/1997 | Murphy et al. |
| 5,697,784 A | 12/1997 | Hafele et al. |
| D388,612 S | 1/1998 | Stutzer et al. |
| D388,613 S | 1/1998 | Stutzer et al. |
| D389,091 S | 1/1998 | Dickinson |
| 5,709,545 A | 1/1998 | Johnston et al. |
| D390,934 S | 2/1998 | McKeone |
| 5,716,007 A | 2/1998 | Nottingham et al. |
| 5,718,668 A | 2/1998 | Arnett et al. |
| 5,746,595 A | 5/1998 | Ford |
| 5,749,726 A | 5/1998 | Kinsel |
| 5,759,502 A | 6/1998 | Spencer et al. |
| 5,779,471 A | 7/1998 | Tseng et al. |
| 5,779,654 A | 7/1998 | Foley et al. |
| 5,795,153 A | 8/1998 | Rechmann |
| 5,796,325 A | 8/1998 | Lundell et al. |
| 5,833,065 A | 11/1998 | Burgess |
| 5,836,030 A | 11/1998 | Hazeu et al. |
| D402,744 S | 12/1998 | Zuege |
| 5,851,079 A | 12/1998 | Horstman et al. |
| D403,511 S | 1/1999 | Serbinski |
| D406,334 S | 3/1999 | Rosenthal et al. |
| 5,876,201 A | 3/1999 | Wilson et al. |
| D408,511 S | 4/1999 | Allen et al. |
| 5,901,397 A | 5/1999 | Häfele et al. |
| 5,934,902 A | 8/1999 | Abahusayn |
| D413,975 S | 9/1999 | Maeda |
| D416,999 S | 11/1999 | Miyamoto |
| D417,082 S | 11/1999 | Classen et al. |
| 5,993,402 A | 11/1999 | Sauer et al. |
| 6,030,215 A | 2/2000 | Ellion et al. |
| 6,038,960 A | 3/2000 | Fukushima et al. |
| 6,039,180 A | 3/2000 | Grant |
| 6,041,462 A | 3/2000 | Marques |
| 6,047,429 A | 4/2000 | Wu |
| D424,181 S | 5/2000 | Caplow |
| D425,615 S | 5/2000 | Bachman et al. |
| D425,981 S | 5/2000 | Bachman et al. |
| 6,056,710 A * | 5/2000 | Bachman ............... A61C 17/02 601/162 |
| D426,633 S | 6/2000 | Bachman et al. |
| 6,089,865 A | 7/2000 | Edgar |
| 6,116,866 A | 9/2000 | Tomita et al. |
| 6,120,755 A | 9/2000 | Jacobs |
| 6,124,699 A | 9/2000 | Suzuki et al. |
| D434,500 S | 11/2000 | Pollock et al. |
| 6,159,006 A | 12/2000 | Cook et al. |
| 6,164,967 A | 12/2000 | Sale et al. |
| D435,905 S | 1/2001 | Bachman et al. |
| D437,049 S | 1/2001 | Hartwein |
| 6,193,512 B1 | 2/2001 | Wallace |
| 6,193,932 B1 | 2/2001 | Wu et al. |
| 6,199,239 B1 | 3/2001 | Dickerson |
| 6,200,134 B1 | 3/2001 | Kovac |
| D439,781 S | 4/2001 | Spore |
| 6,217,835 B1 | 4/2001 | Riley et al. |
| D441,861 S | 5/2001 | Hafliger |
| 6,230,717 B1 | 5/2001 | Marx et al. |
| 6,233,773 B1 | 5/2001 | Karge et al. |
| 6,234,205 B1 | 5/2001 | D'Amelio et al. |
| 6,237,178 B1 | 5/2001 | Krammer et al. |
| 6,247,929 B1 | 6/2001 | Bachman et al. |
| 6,280,190 B1 | 8/2001 | Hoffman |
| D448,236 S | 9/2001 | Murray |
| 6,293,792 B1 | 9/2001 | Hanson |
| D449,884 S | 10/2001 | Tobin et al. |
| 6,299,419 B1 | 10/2001 | Hunklinger |
| D453,453 S | 2/2002 | Lun |
| D455,201 S | 4/2002 | Jones |
| D455,203 S | 4/2002 | Jones |
| 6,363,565 B1 | 4/2002 | Paffrath |
| D457,949 S | 5/2002 | Krug |

(56) References Cited

U.S. PATENT DOCUMENTS

| | | |
|---|---|---|
| D464,799 S | 10/2002 | Crossman et al. |
| 6,468,482 B1 | 10/2002 | Frieze et al. |
| 6,475,173 B1 | 11/2002 | Bachman et al. |
| 6,485,451 B1 | 11/2002 | Roberts et al. |
| 6,497,375 B1 | 12/2002 | Srinath et al. |
| 6,497,572 B2 | 12/2002 | Hood et al. |
| 6,502,584 B1 | 1/2003 | Fordham |
| D470,660 S | 2/2003 | Schaber |
| 6,532,837 B1 | 3/2003 | Magussen, Jr. |
| 6,558,344 B2 | 5/2003 | McKinnon et al. |
| 6,561,808 B2 | 5/2003 | Neuberger et al. |
| D475,346 S | 6/2003 | McCurrach et al. |
| D476,743 S | 7/2003 | D'Silva et al. |
| 6,589,477 B1 | 7/2003 | Frieze et al. |
| 6,602,071 B1 | 8/2003 | Ellion et al. |
| 6,632,091 B1 | 10/2003 | Cise et al. |
| D482,451 S | 11/2003 | Page et al. |
| 6,640,999 B2 | 11/2003 | Peterson |
| 6,647,577 B2 | 11/2003 | Tam |
| 6,659,674 B2 | 12/2003 | Carlucci et al. |
| 6,669,059 B2 | 12/2003 | Mehta |
| D484,971 S | 1/2004 | Hartwein |
| 6,681,418 B1 | 1/2004 | Bierend |
| D486,573 S | 2/2004 | Callaghan et al. |
| 6,689,078 B1 | 2/2004 | Rehkemper et al. |
| 6,699,208 B2 | 3/2004 | Bachman et al. |
| 6,719,561 B2 | 4/2004 | Gugel et al. |
| D489,183 S | 5/2004 | Akahori et al. |
| 6,739,782 B1 | 5/2004 | Rehkemper et al. |
| 6,740,053 B2 | 5/2004 | Kaplowitz |
| D490,899 S | 6/2004 | Gagnon |
| D491,728 S | 6/2004 | Jimenez |
| D492,996 S | 7/2004 | Rehkemper et al. |
| 6,761,324 B2 | 7/2004 | Chang |
| 6,766,549 B2 | 7/2004 | Klupt |
| D495,142 S | 8/2004 | Berde |
| D495,143 S | 8/2004 | Berde |
| 6,779,216 B2 | 8/2004 | Davies et al. |
| 6,783,004 B1 | 8/2004 | Rinner |
| 6,783,505 B1 | 8/2004 | Lai |
| 6,796,796 B2 | 9/2004 | Segal |
| 6,808,331 B2 | 10/2004 | Hall et al. |
| D498,643 S | 11/2004 | Pryor |
| 6,814,259 B1 | 11/2004 | Foster et al. |
| D499,885 S | 12/2004 | Xi |
| 6,835,181 B2 | 12/2004 | Hippensteel |
| D500,599 S | 1/2005 | Callaghan |
| 6,836,917 B2 | 1/2005 | Blaustein et al. |
| 6,837,708 B2 | 1/2005 | Chen et al. |
| 6,884,069 B2 | 4/2005 | Goldman |
| 6,902,337 B1 | 6/2005 | Kuo |
| 6,907,879 B2 | 6/2005 | Drinan et al. |
| D509,685 S | 9/2005 | Kling et al. |
| D513,638 S | 1/2006 | Pan |
| D515,215 S | 2/2006 | Wang |
| D522,652 S | 6/2006 | Massey |
| 7,080,980 B2 | 7/2006 | Klupt |
| D529,661 S | 10/2006 | Schmidt |
| D530,010 S | 10/2006 | Luettgen et al. |
| 7,117,555 B2 | 10/2006 | Fattori et al. |
| D532,570 S | 11/2006 | Vizcarra |
| 7,131,838 B2 | 11/2006 | Suzuki et al. |
| D533,720 S | 12/2006 | Vu |
| 7,147,468 B2 | 12/2006 | Snyder et al. |
| D538,474 S | 3/2007 | Sheppard et al. |
| D548,334 S | 8/2007 | Izumi |
| D550,097 S | 9/2007 | Lepoitevin |
| D553,980 S | 10/2007 | VerWeyst |
| 7,276,035 B2 | 10/2007 | Lu |
| 7,314,456 B2 | 1/2008 | Shaw |
| D565,175 S | 3/2008 | Boyd et al. |
| 7,344,510 B1 | 3/2008 | Yande |
| D565,713 S | 4/2008 | Gao |
| 7,367,803 B2 | 5/2008 | Egeresi |
| D574,952 S | 8/2008 | Boyd et al. |
| 7,414,337 B2 | 8/2008 | Wilkinson et al. |
| D577,198 S | 9/2008 | Jimenez |
| D577,814 S | 9/2008 | Seki et al. |
| D581,279 S | 11/2008 | Oates |
| 7,455,521 B2 | 11/2008 | Fishburne, Jr. |
| 7,469,440 B2 | 12/2008 | Boland et al. |
| D585,132 S | 1/2009 | Pukall |
| D588,262 S | 3/2009 | Pukall |
| 7,500,584 B2 | 3/2009 | Schutz |
| D590,492 S | 4/2009 | Powell |
| D592,748 S | 5/2009 | Boulton |
| D595,136 S | 6/2009 | Canamasas Puigbo |
| D601,694 S | 10/2009 | Rocklin |
| D601,697 S | 10/2009 | Sobeich et al. |
| D603,708 S | 11/2009 | Handy |
| D608,430 S | 1/2010 | Slothower |
| 7,670,141 B2 | 3/2010 | Thomas et al. |
| 7,677,888 B1 | 3/2010 | Halm |
| D613,550 S | 4/2010 | Picozza et al. |
| D621,949 S | 8/2010 | Seki et al. |
| D622,928 S | 9/2010 | Griebel |
| D623,376 S | 9/2010 | Griebel |
| D625,406 S | 10/2010 | Seki et al. |
| 7,814,585 B1 | 10/2010 | Reich |
| D629,884 S | 12/2010 | Stephens |
| 7,857,623 B2 | 12/2010 | Grez |
| 7,862,536 B2 | 1/2011 | Chen et al. |
| 7,878,403 B2 | 2/2011 | Hennick et al. |
| 7,959,597 B2 | 6/2011 | Baker et al. |
| D640,872 S | 7/2011 | Nanda |
| D648,539 S | 11/2011 | Wai |
| D651,409 S | 1/2012 | Papenfu |
| D651,805 S | 1/2012 | Hay |
| D653,340 S | 1/2012 | Goerge et al. |
| 8,113,832 B2 | 2/2012 | Snyder et al. |
| D655,380 S | 3/2012 | Taylor |
| D658,381 S | 5/2012 | Gebski |
| 8,220,726 B2 | 7/2012 | Qiu et al. |
| D666,912 S | 9/2012 | Kawai |
| 8,256,979 B2 | 9/2012 | Hilscher et al. |
| D668,339 S | 10/2012 | Luoto |
| D669,169 S | 10/2012 | Washington et al. |
| 8,297,534 B2 | 10/2012 | Li et al. |
| D670,373 S | 11/2012 | Taylor et al. |
| D670,958 S | 11/2012 | Picozza et al. |
| D671,637 S | 11/2012 | Gebski et al. |
| D672,018 S | 12/2012 | Bucher |
| 8,366,024 B2 | 2/2013 | Leber et al. |
| 8,403,577 B2 | 3/2013 | Khoshnevis |
| 8,403,665 B2 | 3/2013 | Thomas et al. |
| 8,408,483 B2 | 4/2013 | Boyd et al. |
| 8,418,300 B2 | 4/2013 | Miller et al. |
| D686,311 S | 7/2013 | Mori |
| D694,378 S | 11/2013 | Bates |
| D694,398 S | 11/2013 | Taylor |
| D700,343 S | 2/2014 | Liu |
| D702,819 S | 4/2014 | Garland |
| D702,821 S | 4/2014 | Garland |
| D707,350 S | 6/2014 | Woodard |
| D709,183 S | 7/2014 | Kemlein |
| 8,801,667 B2 | 8/2014 | Taylor |
| D714,929 S | 10/2014 | Kim et al. |
| D714,930 S | 10/2014 | Kim et al. |
| D717,412 S | 11/2014 | Bucher |
| D717,427 S | 11/2014 | Kim |
| D718,855 S | 12/2014 | Kim et al. |
| D723,387 S | 3/2015 | Fath |
| D725,770 S | 3/2015 | Kim et al. |
| D731,640 S | 6/2015 | Kim et al. |
| 9,050,157 B2 | 6/2015 | Boyd et al. |
| D735,305 S | 7/2015 | Obara |
| D740,936 S | 10/2015 | Kim et al. |
| D745,329 S | 12/2015 | Ong |
| D746,975 S | 1/2016 | Schenck |
| D747,464 S | 1/2016 | Taylor |
| D754,330 S | 4/2016 | Kim et al. |
| D756,122 S | 5/2016 | Taylor |
| D764,051 S | 8/2016 | Wang |
| D782,326 S | 3/2017 | Fath |

(56) References Cited

U.S. PATENT DOCUMENTS

| | | |
|---|---|---|
| 9,642,677 B2 | 5/2017 | Luettgen et al. |
| D788,907 S | 6/2017 | Kim |
| D798,440 S | 9/2017 | Kim |
| 2002/0090252 A1 | 7/2002 | Hall et al. |
| 2002/0108193 A1 | 8/2002 | Gruber |
| 2002/0119415 A1 | 8/2002 | Bailey |
| 2002/0152565 A1 | 10/2002 | Klupt |
| 2003/0060743 A1 | 3/2003 | Chang |
| 2003/0098249 A1 | 5/2003 | Rollock |
| 2003/0162146 A1 | 8/2003 | Shortt et al. |
| 2003/0204155 A1 | 10/2003 | Egeresi |
| 2003/0213075 A1 | 11/2003 | Hui et al. |
| 2004/0045107 A1 | 3/2004 | Egeresi |
| 2004/0076921 A1 | 4/2004 | Gofman et al. |
| 2004/0122377 A1 | 6/2004 | Fischer et al. |
| 2004/0126730 A1 | 7/2004 | Panagotacos |
| 2004/0180569 A1 | 10/2004 | Chiou |
| 2004/0209222 A1 | 10/2004 | Snyder |
| 2005/0004498 A1 | 1/2005 | Klupt |
| 2005/0049620 A1 | 3/2005 | Chang |
| 2005/0064371 A1 | 3/2005 | Soukos et al. |
| 2005/0101894 A1 | 5/2005 | Hippensteel |
| 2005/0102773 A1 | 5/2005 | Obermann et al. |
| 2005/0144745 A1 | 7/2005 | Russell |
| 2005/0177079 A1 | 8/2005 | Pan |
| 2005/0271531 A1 | 12/2005 | Brown et al. |
| 2006/0008373 A1 | 1/2006 | Schutz |
| 2006/0010624 A1 | 1/2006 | Cleland |
| 2006/0021165 A1 | 2/2006 | Boland et al. |
| 2006/0026784 A1 | 2/2006 | Moskovich et al. |
| 2006/0057539 A1 | 3/2006 | Sodo |
| 2006/0078844 A1 | 4/2006 | Goldman et al. |
| 2006/0079818 A1 | 4/2006 | Yande |
| 2006/0207052 A1 | 9/2006 | Tran |
| 2007/0082316 A1 | 4/2007 | Zhadanov et al. |
| 2007/0082317 A1 | 4/2007 | Chuang |
| 2007/0113360 A1 | 5/2007 | Tsai |
| 2007/0202459 A1 | 8/2007 | Boyd et al. |
| 2007/0203439 A1 | 8/2007 | Boyd et al. |
| 2007/0254260 A1 | 11/2007 | Alden |
| 2008/0008979 A1 | 1/2008 | Thomas et al. |
| 2008/0189951 A1 | 8/2008 | Molema et al. |
| 2008/0213719 A1 | 9/2008 | Giniger et al. |
| 2008/0253906 A1 | 10/2008 | Strong |
| 2008/0307591 A1 | 12/2008 | Farrell et al. |
| 2009/0070949 A1 | 3/2009 | Sagel et al. |
| 2009/0071267 A1 | 3/2009 | Mathus et al. |
| 2009/0082706 A1 | 3/2009 | Shaw |
| 2009/0124945 A1 | 5/2009 | Reich et al. |
| 2009/0139351 A1 | 6/2009 | Reichmuth |
| 2009/0163839 A1 | 6/2009 | Alexander |
| 2009/0188780 A1 | 7/2009 | Watanabe |
| 2009/0281454 A1 | 11/2009 | Baker et al. |
| 2010/0010524 A1 | 1/2010 | Barrington |
| 2010/0015566 A1 | 1/2010 | Shaw |
| 2010/0049177 A1 | 2/2010 | Boone, III et al. |
| 2010/0190132 A1 | 7/2010 | Taylor et al. |
| 2010/0239998 A1 | 9/2010 | Snyder et al. |
| 2010/0261134 A1 | 10/2010 | Boyd et al. |
| 2010/0261137 A1 | 10/2010 | Boyd et al. |
| 2010/0326536 A1 | 12/2010 | Nan |
| 2010/0330527 A1 | 12/2010 | Boyd et al. |
| 2011/0027749 A1 | 2/2011 | Syed |
| 2011/0076090 A1 | 3/2011 | Wu et al. |
| 2011/0097683 A1 | 4/2011 | Boyd et al. |
| 2011/0139826 A1 | 6/2011 | Hair et al. |
| 2011/0144588 A1 | 6/2011 | Taylor et al. |
| 2011/0184341 A1 | 7/2011 | Baker et al. |
| 2011/0307039 A1 | 12/2011 | Cornell |
| 2012/0021374 A1 | 1/2012 | Cacka et al. |
| 2012/0045730 A1* | 2/2012 | Sayder .................. A61C 17/02 433/29 |
| 2012/0064480 A1 | 3/2012 | Hegemann |
| 2012/0077145 A1 | 3/2012 | Tsurukawa |
| 2012/0141952 A1 | 6/2012 | Snyder et al. |
| 2012/0179118 A1 | 7/2012 | Hair |
| 2012/0189976 A1 | 7/2012 | McDonough et al. |
| 2012/0266396 A1 | 10/2012 | Leung |
| 2012/0277663 A1 | 11/2012 | Millman et al. |
| 2012/0277677 A1 | 11/2012 | Taylor et al. |
| 2012/0277678 A1 | 11/2012 | Taylor et al. |
| 2012/0279002 A1 | 11/2012 | Sokol et al. |
| 2012/0295220 A1 | 11/2012 | Thomas et al. |
| 2013/0089832 A1 | 4/2013 | Lee |
| 2013/0295520 A1 | 11/2013 | Hsieh |
| 2014/0106296 A1 | 4/2014 | Woodard et al. |
| 2014/0193774 A1 | 7/2014 | Snyder et al. |
| 2014/0259474 A1 | 9/2014 | Sokol et al. |
| 2014/0272769 A1 | 9/2014 | Luettgen et al. |
| 2014/0272782 A1 | 9/2014 | Luettgen et al. |
| 2014/0352088 A1 | 12/2014 | Wu |
| 2015/0004559 A1 | 1/2015 | Luettgen et al. |
| 2015/0147717 A1 | 5/2015 | Taylor et al. |
| 2015/0173850 A1 | 6/2015 | Garrigues et al. |
| 2015/0182319 A1 | 7/2015 | Wagner et al. |
| 2016/0151133 A1 | 6/2016 | Luettgen et al. |
| 2017/0239132 A1 | 8/2017 | Luettgen et al. |

FOREIGN PATENT DOCUMENTS

| | | |
|---|---|---|
| CN | 204049908 | 12/2014 |
| DE | 1466963 | 5/1969 |
| DE | 1566490 | 11/1970 |
| DE | 2019003 | 11/1971 |
| DE | 2409752 | 9/1975 |
| DE | 2545936 | 4/1977 |
| DE | 2714876 | 10/1978 |
| DE | 2910982 | 2/1980 |
| DE | 3346651 | 7/1985 |
| EP | 0023672 | 7/1980 |
| EP | 0515983 | 2/1992 |
| EP | 1825827 | 8/2007 |
| FR | 2556954 | 6/1985 |
| FR | 2654627 | 5/1991 |
| GB | 838564 | 6/1960 |
| GB | 1182031 | 2/1970 |
| GB | 2018605 | 10/1979 |
| GB | 2237505 | 5/1991 |
| JP | 2-134150 | 4/1990 |
| JP | 2009-39455 | 2/2009 |
| KR | 20120126265 | 11/2012 |
| WO | WO95/016404 | 6/1995 |
| WO | WO01/10327 | 2/2001 |
| WO | WO01/19281 | 3/2001 |
| WO | WO04/021958 | 3/2004 |
| WO | WO04/039205 | 5/2004 |
| WO | WO2004/062518 | 7/2004 |
| WO | WO2004060259 A2 | 7/2004 |
| WO | WO2008/070730 | 6/2008 |
| WO | WO2008157585 A1 | 12/2008 |
| WO | WO2013/095462 | 6/2013 |
| WO | WO2013/124691 | 8/2013 |
| WO | WO2014145890 | 9/2014 |

OTHER PUBLICATIONS

The Right Tool, Electron Fusion Devices, Inc., 2 pages, at least as early as Feb. 1991.

Japanese Packaging, 2 pages, at least as early as Dec. 2002.

Japanese Instruction Brochure, 20 pages, at least as early as Dec. 2002.

Brochure: Woog International, "You have a 98% chance of getting gum disease. Unless you read this.", Lancaster, Pennsylvania, 5 pages, Feb. 1987.

Brochure: Woog International, "We put the control of home dental care back into the hands of the professional", Lancaster, Pennsylvania, 2 pages, Feb. 1987.

Brochure: WOOG International, "Products at a Glance: Home Dental Care System" WOOG ORAJET, 3 pages, at least as early as Dec. 18, 1998.

Website: http://www.just4teeth.com/product/Panasonic/Panasonic_Portable_Irrigator.htm, 2 pages, at least as early as Jun. 20, 2003.

(56) References Cited

OTHER PUBLICATIONS

Website: http://www.videodirectstore.com/store/merchant.mv?Screen=PROD&Product_Code=EW1' . . . , 2 pages, at least as early as Jun. 20, 2003.
Website: http://products.consumerguide.com/cp/family/review/index.cfm/id/18742, 2 pages, at least as early as Jun. 20, 2003.
Website: http://www.racekarteng.com/images/walbroparts.gif and http://www.muller.net/mullermachine/docs/walbro1.html, 4 pages, at least as early as Jun. 20, 2003.
European Search Report, EPO Application No. 07250799.9, dated Jul. 5, 2007.
European Search Report, EPO Application No. 07252693.2, 14 pages, dated Apr. 28, 2008.
European Examination Report, EPO Application No. 07250799.9, dated Feb. 5, 2009.
International Search Report, Application No. PCT/US2010/028180, 2 pages, dated May 18, 2010.
International Search Report, PCT/US2010/060800, 2 pages, dated Feb. 11, 2011.
International Search Report, PCT/US2011/052795, 10 pages, dated Jan. 17, 2012.
Waterpik SinuSense Website: http://www.insightsbyapril.com/2012/03/waterpik-natural-remedy-for-sinus.html, 8 pages, retrieved on May 31, 2012.
Waterpik WP 350W Oral Irrigator. Dentist.net. Copyright date 2013. Date accessed: Mar. 30, 2017, 2 pages <http://www.dentalhoo.com/waterpik-wp350.asp>.
iPik Portable Oral Irrigator. AliExpress. Date reviewed: Oct. 5, 2016. <https://www.aliexpress.com/...e-Oral-Care-Product-Nasal-Irrigator-Tooth-Flosser-Water/1525541997.html?aff_platform=aaf&cpt=1490913714609&sk=yfAeyJa&aff_trace_key=c5a300c4f02e46d08c042f5292e1762f-1490913714609-07517-yfAeyJa>, 18 pages.
Brite Leafs Professional Portable 2-in-1 Nasal Sinus & Oral Irrigator. Brite Leafs. Copyright date 2012, <http://www.briteleafs.com/product6.html>, 1 page.
AliExpress. Date reviewed: Jan. 12, 2017. <https://www.aliexpress.com/item/Cordless-Water-Floss-Portable-Oral-Irrigator-Dental-Water-Flosser-Waterpic-Whatpick-Dental-Water-Pic-Whater-Pick/32769416341.html?spm=2114.40010308.4.75.Owuzfj>.
Suvo. "Helical Gears vs Spur Gears—Advantages and Disadvantages Compared." Brighthub Engineering, Aug. 18, 2010, www.brighthubengineering.com/manufacturing-technology/33535-helical-gears-vs-spur-gears/., 7 pages.
Waterpik ADA Accepted WP-663, posted at amazon.com, earliest date reviewed on Feb. 6, 2014, [online], acquired on Feb. 12, 2018. Available from Internet, <URL: https://www.amazon.com/Waterpik-Accepted-WP-663-Aquarius-Flosser/dp/B072JFVXSY/ref=cm_cr_arp_d_product_top?ie=UTF8&th=1> (Year: 2014).
Waterpik Classic Professional Water Flosser, WP-72, posted at amazon.com, earliest date reviewed on Mar. 5, 2016, [online], acquired on Feb. 23, 2018. Available from Internet, <URL: https://www.amazon.com/Waterpik-Classic-Professional-Flosser-WP-72/dp/B00HFQQOU6/ref=cm_cr_arp_d_product_top?ie=UTF8> (Year: 2016).

\* cited by examiner

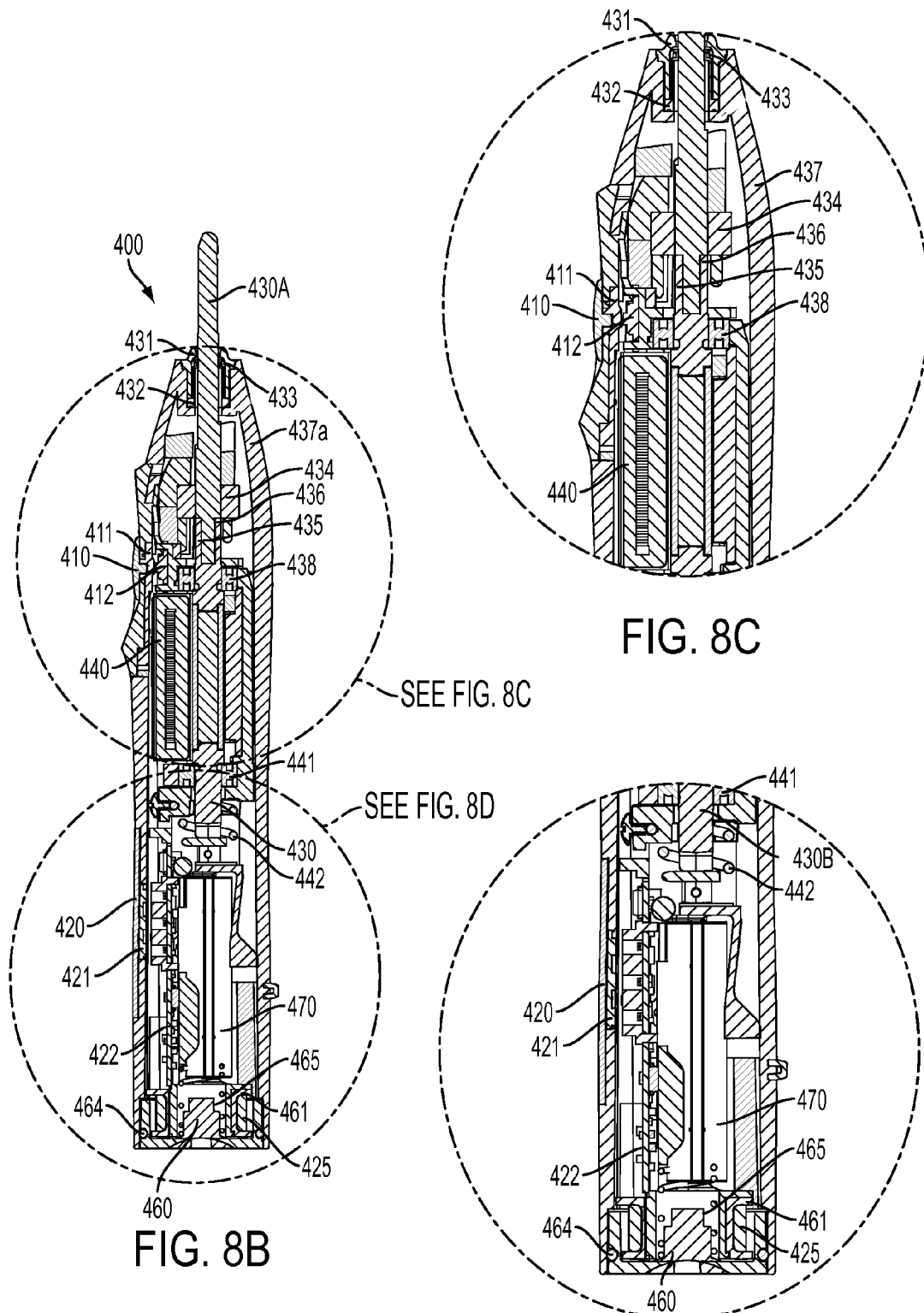

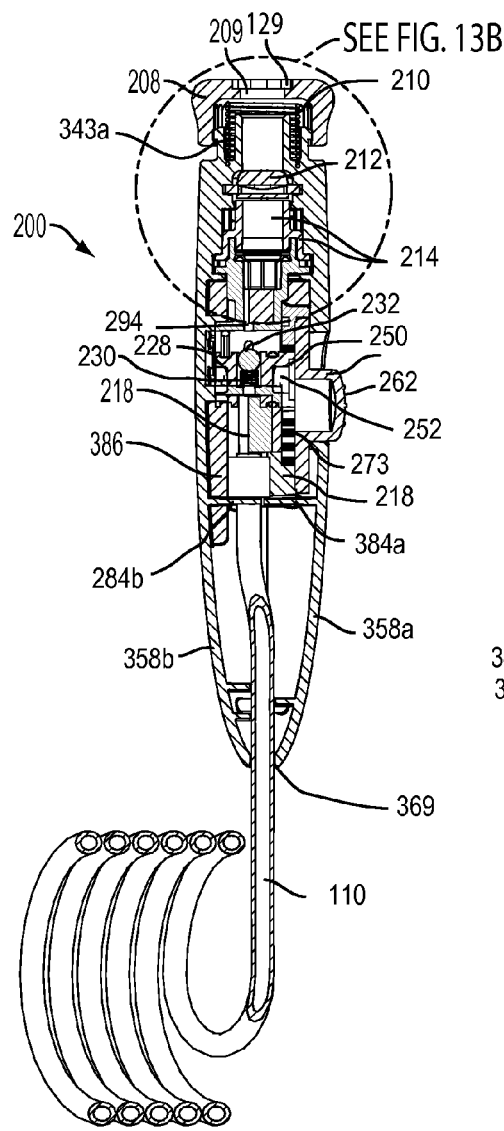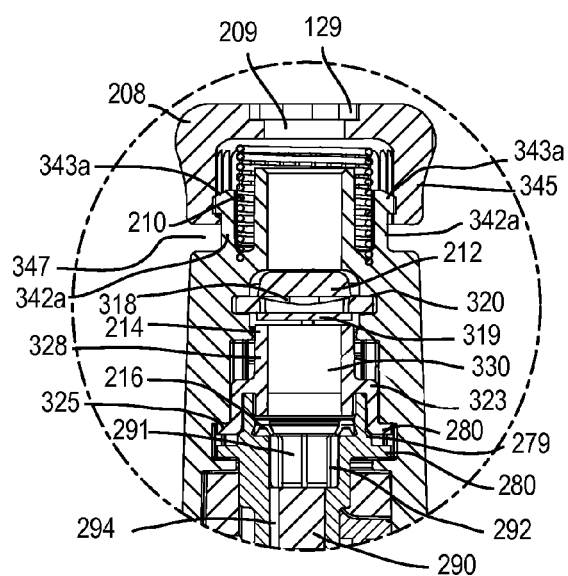
FIG. 13A
FIG. 13B

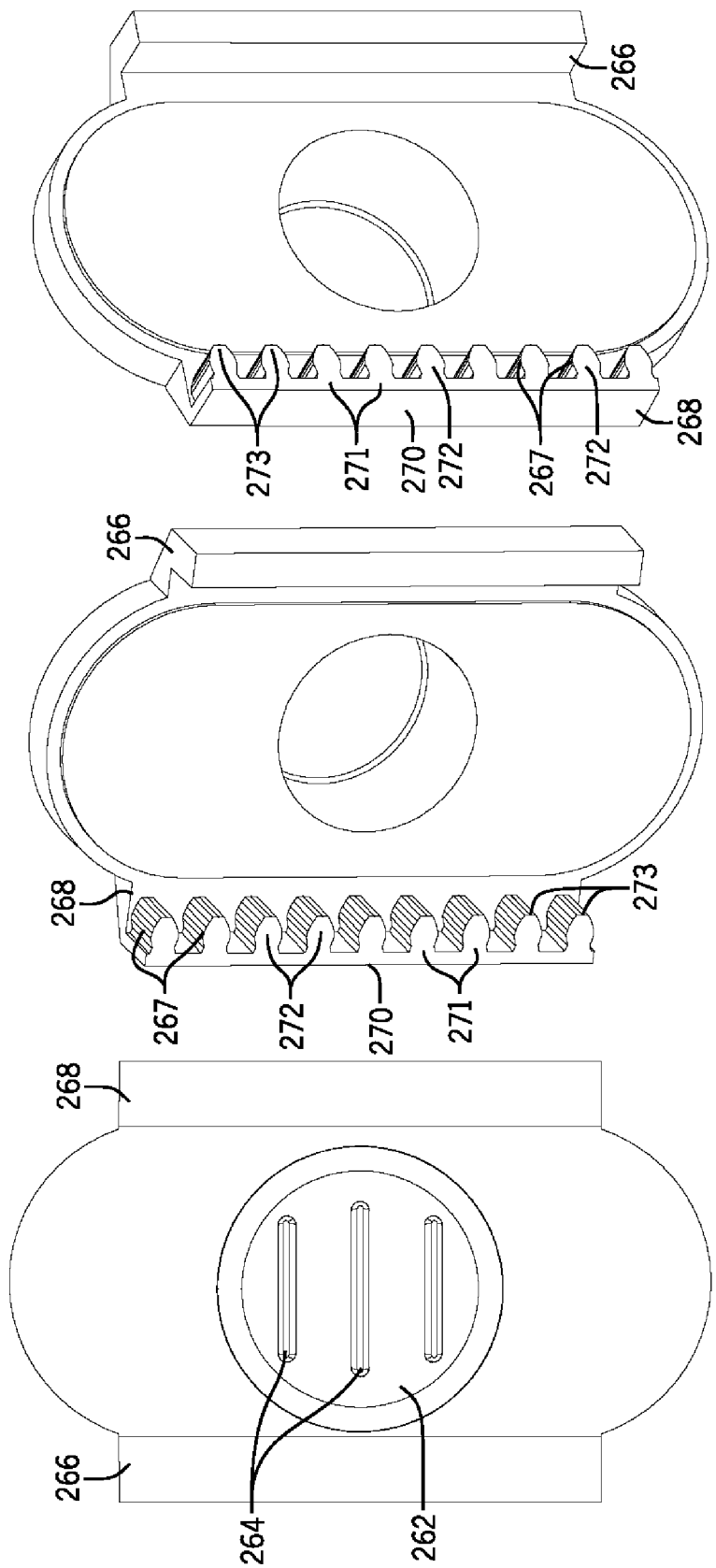

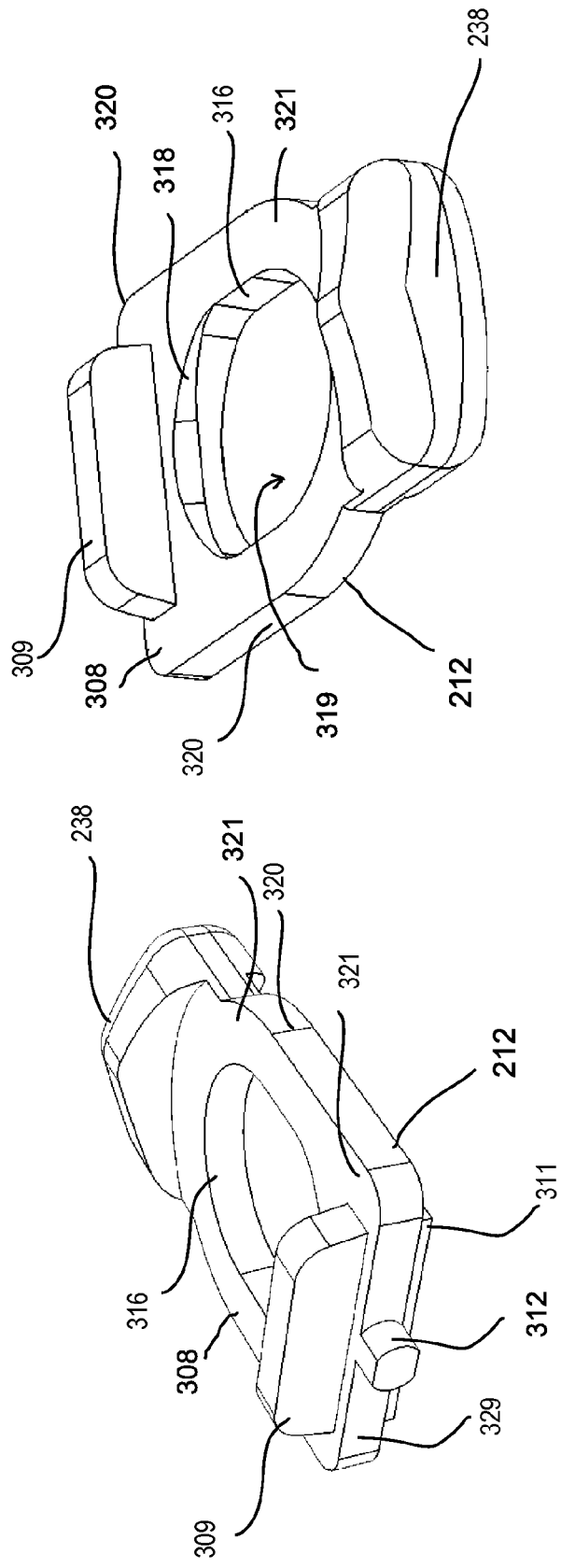

ORAL HYGIENE SYSTEM

CROSS REFERENCE TO RELATED APPLICATIONS

The present application is a continuation-in-part of U.S. patent application Ser. No. 14/555,339 filed 26 Nov. 2014 "Oral Irrigator with Slide Pause Switch," which claims the benefit of priority pursuant to 35 U.S.C. § 119(e) of U.S. provisional application No. 61/909,738 filed 27 Nov. 2013 entitled "Oral Irrigator with Slide Pause Switch," both of which are incorporated herein by reference in their entireties. This application also claims priority pursuant to 35 U.S.C. § 119(e) to U.S. provisional application No. 61/924,053 filed 6 Jan. 2014 entitled "Oral Hygiene Device," which is hereby incorporated herein by reference in its entirety.

BACKGROUND

Oral irrigators typically are used to clean a user's teeth and gums by discharging a pressurized fluid stream into a user's oral cavity. The fluid impacts the teeth and gums to remove debris. Often, the oral irrigator includes a fluid supply, such as a reservoir, that is fluidly connected by a pump to an oral irrigator tip, often through a handle. In some oral irrigators, water flow through the handle can be stopped only by turning off power to the irrigator. Other oral irrigators include actuators to pause fluid flow through the handle without turning off power to the irrigator, but these often include electrical circuitry within the handle and in close proximity to fluid conduits, which creates a safety hazard. Oral irrigators with such electrical actuators are also expensive to manufacture.

Toothbrushes are also frequently used oral hygiene devices. A variety of toothbrush designs exist including electro-magnetic and oscillating mechanical brushes. The different styles include their own characteristics. Electromagnetic systems frequently have a relatively high production cost. There are also currently many toothbrushes that provide oscillating output brush motion from continuously rotating input drivers. Mechanically driven toothbrushes typically have a reduced manufacturing cost as compared to toothbrushes employing electro-magnetic drivers. However, such rotating systems all perform the oscillating function at speeds well below sonic level.

The information included in this Background section of the specification, including any references cited herein and any description or discussion thereof, is included for technical reference purposes only and is not to be regarded subject matter by which the scope of the invention as defined in the claims is to be bound.

SUMMARY

In accordance with various embodiments a dental hygiene apparatus may include a base housing which encloses a pump system driven by a plunger connected to an eccentric bushing mounted to helical gear driven by a motor, which drives the plunger. The helical gear may be enclosed in a gear housing. The dental hygiene apparatus may also include an oral irrigation handle with a removable tip fluidly connected to the pump system via a tube. The apparatus may include a toothbrush removably positioned within a support collar formed as a contiguous part of the base housing. The apparatus may include a reservoir having a volume for holding a fluid. The reservoir may be mounted on the base housing. The apparatus may also include an accessory storage container. The accessory storage container may have a lid connected to and movable relative to the accessory storage container. The apparatus may include a drain hole located below the gear housing. The drain hole may be operable to remove fluid and debris from the gear housing. The apparatus may include a second lid covering the reservoir.

The toothbrush may be a sonic toothbrush driven by a motor located within a housing of the toothbrush. The toothbrush support collar may include an inductive coil operable to charge a rechargeable battery within the toothbrush.

The oral irrigation handle may include a sliding pause switch that translates longitudinal motion into a rotational motion. The switch may engage or disengage a valve internal to the handle. The oral irrigation handle may include a tip retention aperture located below a spring loaded head portion. The spring loaded head portion may force the tip against the tip retention aperture. The tip retention aperture may slide transversely across the handle and engage a retention groove in the tip.

At least one of the lids may include a ventilation aperture located in the lid for ventilating the accessory storage container when the lid is in a closed position. The accessory storage container and the lid may define a substantially enclosed volume for storing at least one item, wherein the lid includes at least one hinged position. The accessory storage container includes walls formed within the accessory storage container and configured to receive and retain a tip therein.

The pump system may be powered by a power cord routed through a channel on a bottom surface. The cord may be supported by internal strain relief comprising a strain relief with a plurality of walls that protrude into the channel.

The apparatus may include a helical gear attached to the motor. The motor helical gear may drive the helical gear engaged with eccentric bushing. The motor may be located above the gear housing. A motor shaft passes through the gear housing and into the motor helical gear. The gear housing may include an aperture that the plunger passes through. The aperture may extend from the gear housing into the base housing which encloses the pump the motor. The interior of the gear housing may be sealed off from the cavity of the base housing that encloses the pump and the motor at the aperture by an elastomer seal that contacts the gear housing and contacts the plunger. The elastomer seal may be a water resistant barrier that limits any contents of the gear housing from contaminating the water utilized in the oral hygiene apparatus.

The apparatus may include elastomer supports located on a bottom surface. The elastomer supports may include a flat surface parallel with the bottom of the base housing and having annular walls that extend from the flat surface. The elastomer supports may be connected to the bottom of the base housing by screws that are coaxial with the annular walls and extend through the flat surface and through the bottom of the base housing. The annular walls may extend past the screw heads such that in response to being set on a flat surface the annular walls support the base housing.

The apparatus may include a second drain hole located in a lower chassis that forms the bottom of the gear housing. The lower chassis may separate an interior of the gear housing from a bottom plate of the base housing. The first drain hole and the second drain hole are operable to evacuate the liquid and debris within the gear housing to the exterior of the base housing.

While multiple examples are disclosed, still other examples of the present invention will become apparent to those skilled in the art from the following detailed description, which shows and describes illustrative examples of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 8B is a cross-sectional view of the toothbrush along line 8-8 in FIG. 4.

FIG. 8C is a sectional view of the cross-sectional view of FIG. 8B depicting the toothbrush along line 8-8 in FIG. 4.

FIG. 8D is a sectional view of the cross-sectional view of FIG. 8B depicting the toothbrush along line 8-8 in FIG. 4.

FIG. 13A is a cross-sectional view of the irrigator handle along line 13A-13A in FIG. 2.

FIG. 13B is a sectional view of the cross-sectional view of FIG. 13A depicting the oral irrigator handle along line 13A-13A in FIG. 2.

FIG. 15A is a front view of the pause control actuator.

FIG. 15B is a perspective rear view showing the gear tooth of the pause control actuator.

FIG. 15C is a perspective rear view showing the flange of the pause control actuator.

FIG. 17A is a perspective front view of the spool body.

FIG. 17B is a perspective rear view of the spool body.

DETAILED DESCRIPTION

Figure 1:
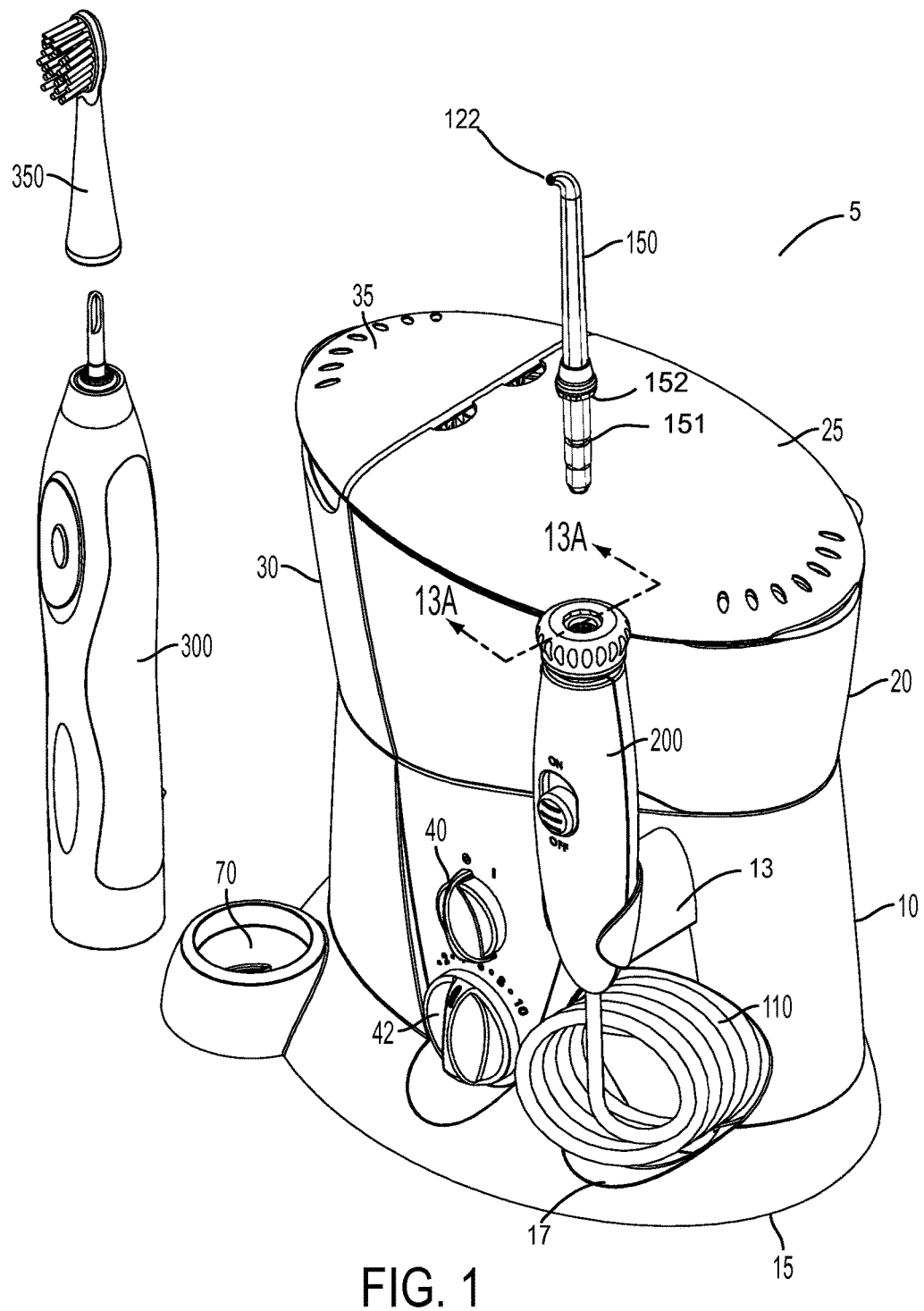
FIG. 1 is a front perspective view of a combination oral hygiene device.

An oral hygiene system may take the form of an apparatus for providing a pressurized water stream for cleaning gums and teeth, as well as a toothbrush. One embodiment includes a base unit defining a cavity. The cavity contains a pump, which moves pressurized water from a reservoir to a tip in fluid communication with the pump. The reservoir may be supported on the base unit and in fluid communication with the pump. The pump may be connected to an electrical power source in order to power the pump. The pump may be turned on and off using a switch. A flow control knob may be turned to selectively adjust the water pressure supplied by the tip between a minimum and a maximum value. The reservoir may be removed from the base unit so that it may be filled with a fluid, such as water, from a fluid source (such as a water faucet). The reservoir may support a container for storing tips or other items.

Fluid may flow from the reservoir, through the base supporting the reservoir, along a tube, into the handle, and into the tip. The fluid may be propelled by a motive source, such as a plunger, to facilitate this flow. Fluid may ultimately be ejected from the tip and into the mouth of a user (for example) to provide oral irrigation and/or cleaning of the teeth, gums, and tongue. The flow of fluid may further be controlled on the handle by a pause switch. Fluid flow is interrupted by a mechanically controlled pause mode conveniently located on the handle of the irrigator. In one exemplary embodiment, manually operating a control actuator slides an attached rack gear, which rotates the coupled pinion gear of a valve gear, which in turn moves a ball inside the valve gear into a position that blocks fluid flow through the handle. The tip may be removable from the handle by pressing a tip eject button. The oral hygiene device may also include an electro-mechanically driven sonic toothbrush. The toothbrush may be mountable and charged via a coil contained in the base unit of the oral hygiene device.

System Components

With reference to FIGS. 1-5, the oral irrigator 5 may include a base, a reservoir 20, a handle 200, and a toothbrush 300. The oral irrigator 5 may also include a lid 25 for the reservoir 20 and a lid 35 for an accessory compartment 30. The base 10 may provide support for the reservoir 20 and the handle 200, as well as house many of the drive and power assembly components of the oral irrigator 5. For example, the base 10 may house a pump, control circuitry, and/or motor, and/or an induction coil for charging the toothbrush.

The base 10 may include a lower base body 15 and an upper base body 10. The lower base body 15 forms a platform or tray that sits within the upper base body 10. The lower base body 15 provides support for one or more of the internal components of the oral irrigator 5 and the upper base body 10 encloses those components to conceal them, as well as provide protection for those components.

The base 10 may also include a clip 13, clamp, or other structure to releasably support the handle 200. In some examples, the clamp 13 may be a C-clip; however, other attachment mechanisms are envisioned. The base 10 may also include a tube cavity 17 or tube box that may receive and support the tube 110 in a coiled position. The tube cavity 17 may be recessed into the upper base body 10. The tube cavity 17 may be flush with the upper base body 10. The tube cavity 17 may extend outwards from the upper base body 10.

The base 10 may also include a power cable to connect a power source (not shown) to the pump. The power cable may pass through the lower base body 15 via opening 45. A first control actuator 40 may be configured to selectively power the oral irrigator 5. For example, the first control actuator 40 may be a power button or knob to turn the oral irrigator 5 on and off. With reference to FIGS. 7B and 7C, the control actuator 40 may translate mechanical movement into an electrical signal. The control actuator 40 may be mounted on an actuator plate 700 that is positioned within the housing. The actuator plate 700 supports the first control actuator 40 and the second control actuator 42 (discussed in more detail below). For example, the actuator plate 700 may include a control recess 704 that receives the second control actuator 42.

The actuation assembly for the first control actuator 40, includes the actuator 40 or knob that is rotated by a user, a knob gear 706 connected to a back side of the first control actuator 40, a switch gear 412, and a switch 702. The knob gear 706 is connected to the first control actuator 40 by a fastener 718, such that as the actuator 40 rotates, the knob gear 706 rotates therewith. The knob gear 706 includes a plurality of gear teeth 716 extending from one end and a limited 708 extending from a second end opposite of the gear teeth 716. The limiter 708 prevents a user from over-rotating the actuator 40.

The switch 706 is an electrical switch and is electrical communication with the power source, circuit board 600, and/or motor 500 for the oral irrigator. The switch 702 may be configured to activate one or more components of the oral irrigator. The switch 702 includes a plurality of prongs that may be connected to one or more wires or other communication pathways to provide communication from the switch 702 to the circuit board 600 or the like. The switch gear 712 is positioned on a back surface of the switch 702 and movable longitudinally relative thereto. The switch gear 712 is connected to the switch 702 so as to change the switch from a first state to a second state. For example, in a first position of the switch gear 412 the switch 702 is in a first state (e.g., on) and in a second position of the switch gear 712 the switch 702 is in a second state (e.g., off). The switch gear 412 includes a plurality of gear teeth 714. The gear teeth 714 of the switch gear 712 mesh with the gear teeth 716 of the knob gear 706.

To operate the first actuation assembly, the user rotates the first control actuator 40 along a rotational path R. When the first control actuator 40 is rotated in a first rotational direction, the knob gear 706 rotates correspondingly, and the gear teeth 716 of the knob gear 706 mesh with the gear teeth 714 of the switch gear 712 to move the switch gear 712 vertically along the length of the switch 702, which causes the gears witch 712 to move between a first position and a second position, changing the state of the switch 702 from a first state to a second state (e.g., from off to on).

A second control actuator 42 may be configured to vary a fluid pressure of fluid as it exits a tip 150 on the handle. For example, the second control actuator 42 may be operably connected to a valve assembly within a pump that selectively changes the diameter and/or length of the fluid pathway between reservoir 20 and the tip 150. As the pathway changes, such as due to a user turning the second control actuator 42, the outlet fluid pressure as fluid is expelled from the tip 150 may be selectively modified. A similar control actuator 42 is disclosed in U.S. Pat. No. 8,408,483 entitled "Adjustable Flow Regulator for Dental Water Jet," which is hereby incorporated herein in its entirety.

Figure 2:
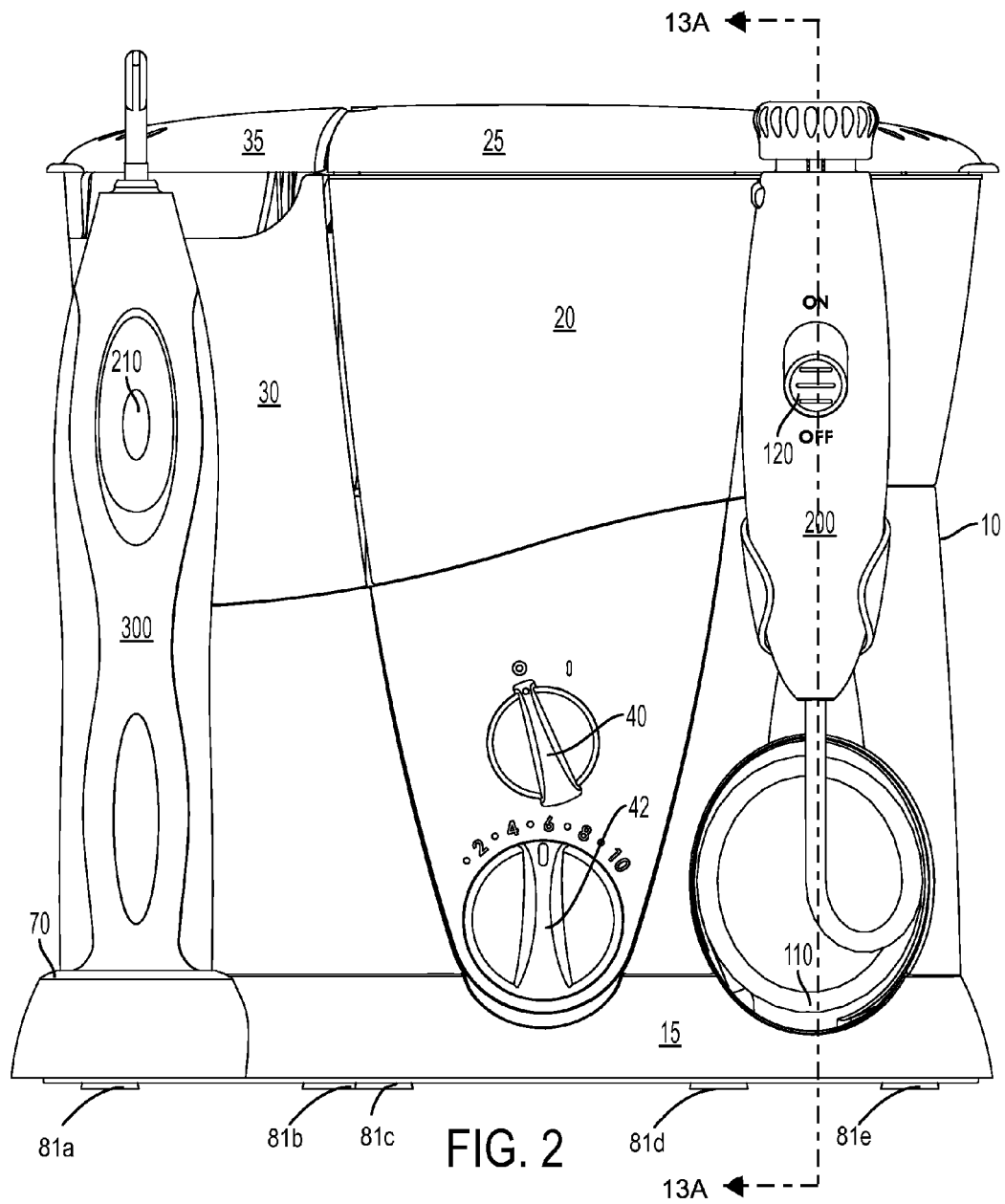
FIG. 2 is a front view of the oral hygiene device of FIG. 1.

With further reference to FIGS. 1 and 2, the handle 200 is removable from the clip 13 on the base 10 and is in fluid communication with the reservoir 20. For example, the tube 110 fluidly connects the reservoir 20 to the handle 200 via a hose connector 125 such that liquid held in the reservoir 20 can be expelled through the tip 114 connected to the handle 200. As described in more detail below, the handle 200 may be used to vary one or more characteristics of the fluid flow output by the tip 150 separate from or in addition to the features (e.g., the first, second, and third control actuators 40, 42) for controlling the fluid output within the base 10.

The tip 150 is selectively removable from the handle 200. For example, and as described in more detail below, a tip eject button 238 can selectively release the tip 150 from the handle 200. The tip 150 defines a fluid pathway that is fluidly connected to the tube 110. The tip 150 includes a tip outlet 122 from which fluid from the reservoir 20 is expelled into a user's mouth from the oral irrigator 5. The tip 150 generally is configured to be inserted into a user's mouth and to expel fluid against a user's teeth, gums, tongue, etc. In some examples, the tip outlet 122 portion of the tip 150 may be shaped as a nozzle or may include a nozzle or other attachment connected thereto. Although a tip 150 is shown, in other embodiments, the oral irrigator 5 may include other accessories, such as a brush head, a nozzle with one or more bristles or cleaning elements, or the like. Accordingly, the discussion of the tip 150 as an outlet for the oral irrigator 5 is meant as illustrative only.

With further reference to FIGS. 1-5, the toothbrush 300 is removable from the toothbrush receptacle 70. The toothbrush receptacle 70 may be formed as part of lower base body 15 and may be integral therewith. As discussed in more detail below, the integrated base and toothbrush holder allows a user to more easily store both components of the oral hygiene system and helps to provide a reminder for a user to complete both the irrigating and brushing steps for oral hygiene, since both components are connected together.

The toothbrush receptacle 70 may be operable to secure and/or charge toothbrush 300. The toothbrush 300 may also include a removable toothbrush tip 350 attachable at the end of the toothbrush. The toothbrush 300 may also include switch 310 operable to turn the toothbrush power on and off.

Figure 3:
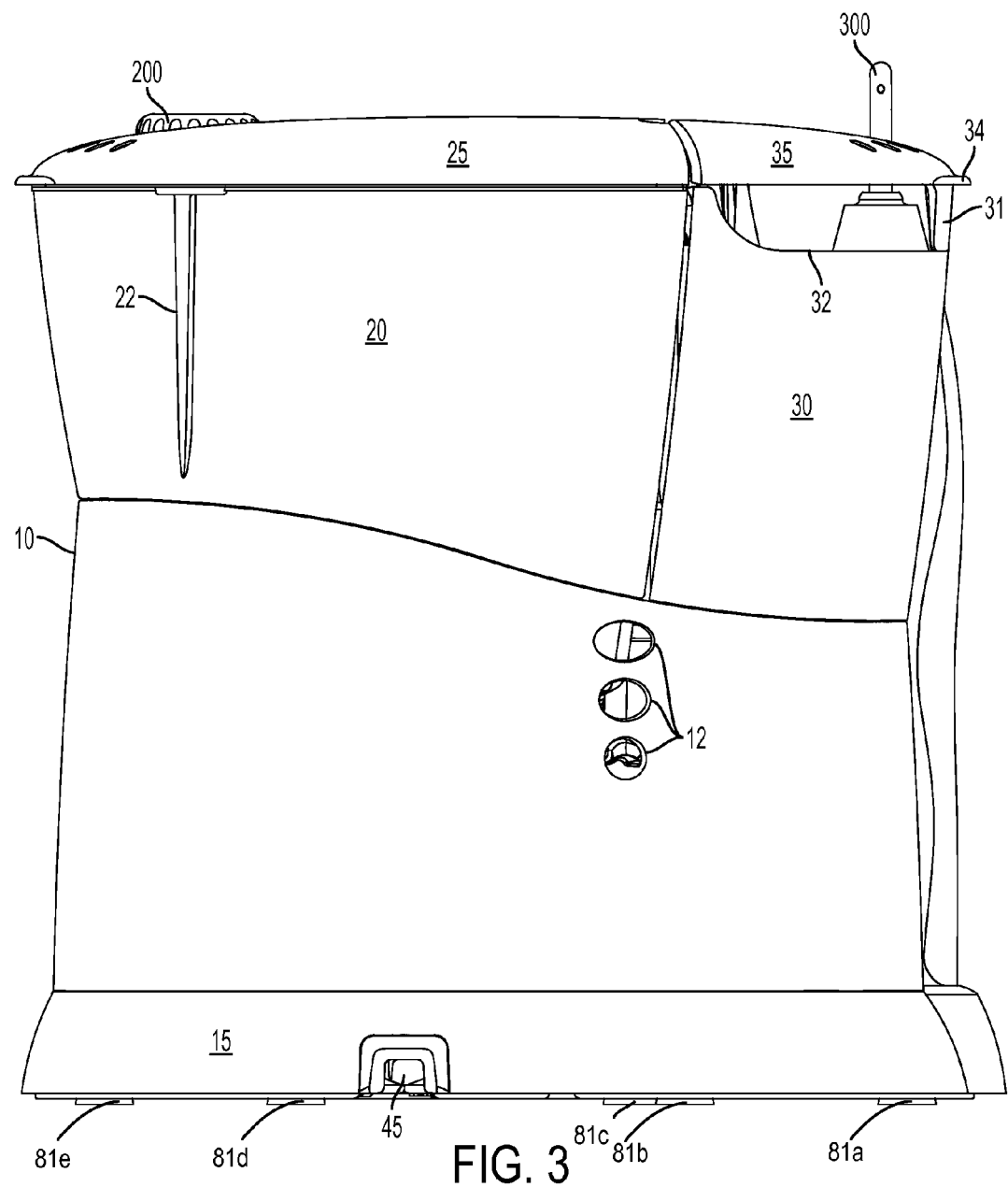
FIG. 3 is a rear view of the oral hygiene device of FIG. 1.

FIG. 3 depicts a rear view of the oral irrigator 5. The upper base body 10 may include one or more drain holes 12 that pass through the upper base body 10. The one or more holes may be positioned vertically in a line. In various embodiments, there may be three drain holes 12. The lowest of three vertical drain holes may be circular, the middle of the three vertical may be oblong compared to the lowest hole and the highest of the three drain holes 12 may be oblong compared to the middle of the three vertical drain holes 12. The drain holes 12 may be operable to drain water form the upper base body 10 which may accumulate water below the reservoir 20. The drain holes prevent fluids from building up in the base unit and encourage quick evaporation.

Figure 4:
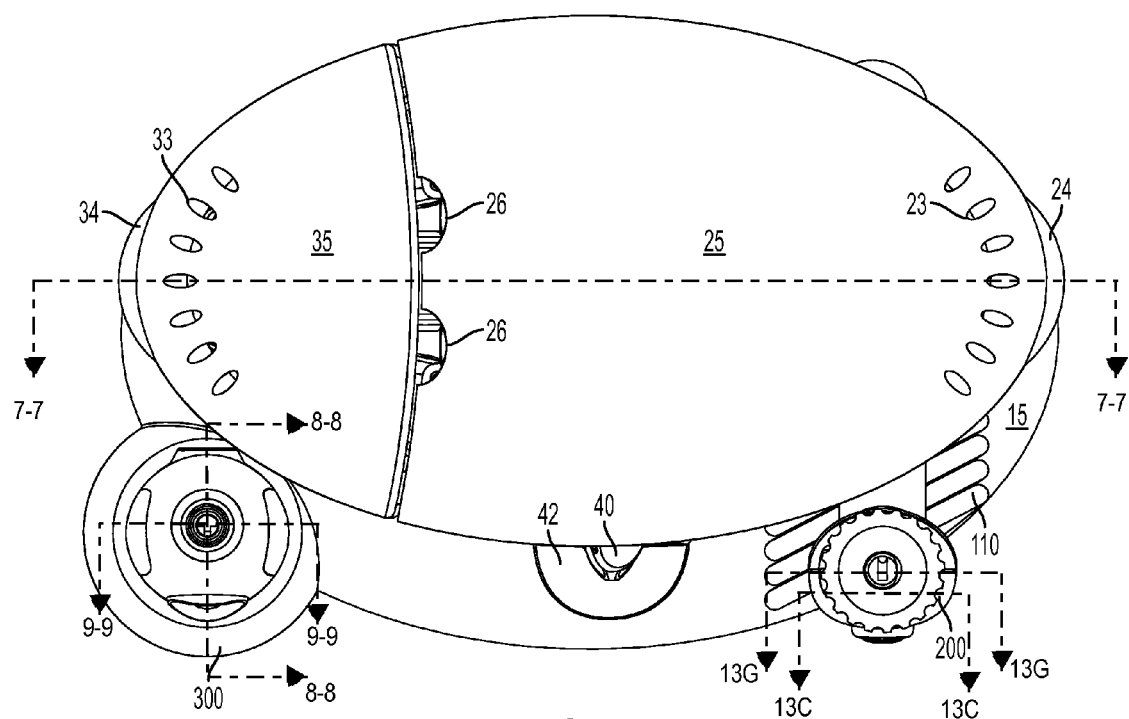
FIG. 4 is a top view of the oral hygiene device of FIG. 1.

As indicated above, the oral irrigator 5 may also include a reservoir 20. The reservoir 20 may include a rib and support platform 22. As shown in FIG. 4, the support platform 22 and reservoir 20 supports a lid 24. The lid 25 may have one or more vent holes 23. The lid 25 may have a tab 24. The tab 24 may extend from one end of the lid 25 and the tab 24 may be operable to engage with a user's finger for opening lid 25. One or more hinges 26 may extend from one side of lid 35. The one or more hinges 26 may extend from the opposite side of tab 24.

With reference to FIGS. 1-4, as indicated above, the oral irrigator 5 may also include an accessory compartment 30. The accessory compartment 30 may have a lid 35. The lid 35 may have one or more vent holes 33 arranged around a portion of the outer periphery edge of the lid 35. The lid 35 may have a tab 34 extending from one end of the lid 35 and the tab 34 may be operable to engage with a user's finger for opening lid 35. One or more hinges 26 may extend from one side of lid 35. The one or more hinges 26 may extend from the lid 35 on the opposite side from tab 34. As shown in FIG. 3, the lid 35 may have a standoff 31 extending from a bottom surface thereof. The standoff 31 or support may extend below tab 34 toward the accessory compartment 30. The standoff 31 may engage a top surface 32. The standoff 31 may support the lid 35 above the accessory compartment 30 and surface 32, defining a space between the surface 32 and the lid 35, which encourages air flow into the accessory compartment 30 and assists in drying the various accessories.

Figure 5:
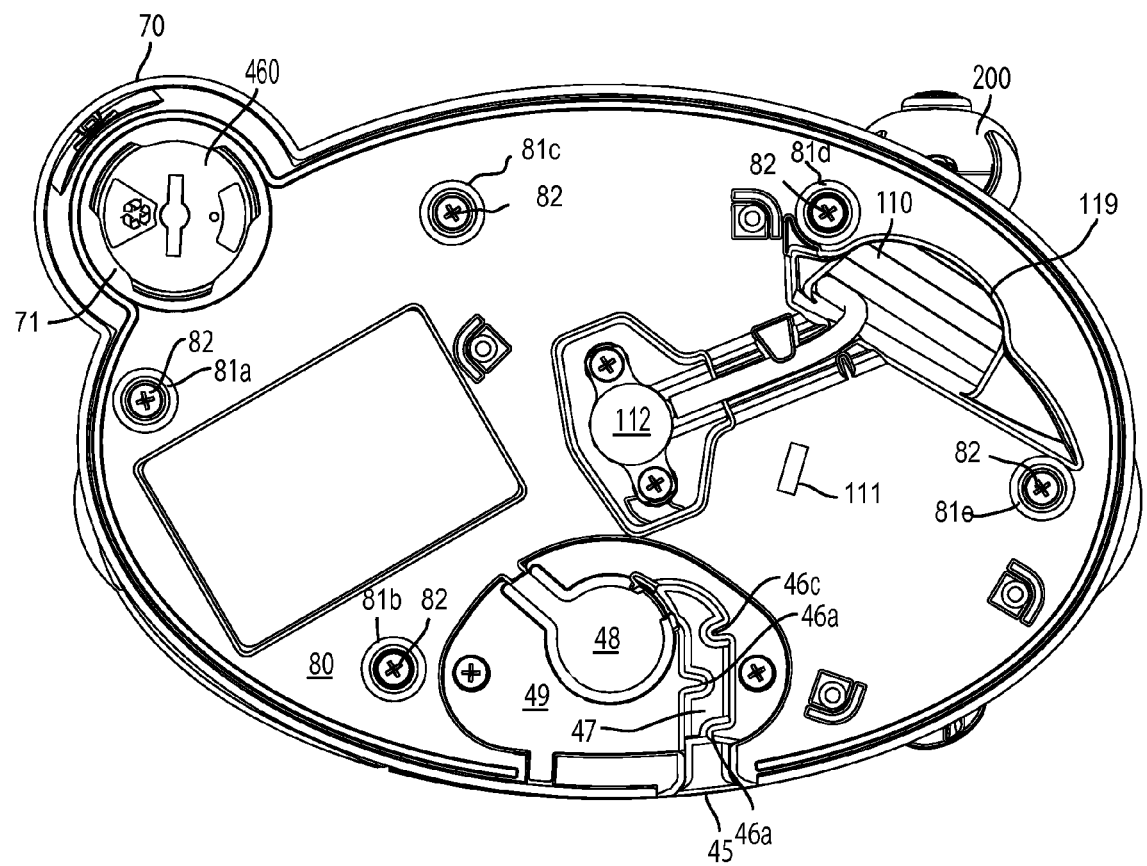
FIG. 5 is a bottom view of the oral hygiene device of FIG. 1.

FIG. 5 depicts a bottom view of the oral irrigator 5. The oral irrigator 5 may include a bottom plate 80 operable to support components on the underside of the oral irrigator. The bottom plate 80 may be attached to and supported by elastomer supports 81a, 81b, 81c, 81d, and 81e. Elastomer supports 81a, 81b, 81c, 81d, and 81e may be used to elevate the outer surface of the base unit above a surface upon which the base unit may be supported. Further vibration reduction for the pump may be obtained by use of elastomer supports 81a, 81b, 81c, 81d, and 81e composed of rubber or other suitable vibration dampening material. The elastomer supports 81a, 81b, 81c, 81d, and 81e may have annular walls which extend from a flat surface. The elastomer supports 81a, 81b, 81c, 81d, and 81e may be attached to bottom plate 80 by screws 82. The screws 82 may be coaxial with the annular walls and extend through the flat surface of the elastomer supports 81a, 81b, 81c, 81d, and 81e. The screws 82 may extend through the bottom plate 80 of the base unit and into standoffs attached to the housing of the base unit thus attaching the bottom plate of the base unit to the housing of the base unit. The annular walls may extend past the screw heads such that in response to being set on a flat surface the annular walls support the base housing and prevent or limit any contact between the flat surface and the heads of screws 82. The elastomer supports 81a, 81b, 81c, 81d, and 81e may be generally cylindrical and may include a recessed surface from which a generally circular footing wall may extend. However it may be noted that the elastomer supports 81a, 81b, 81c, 81d, and 81e may be any shape sufficient to support the base unit. In various embodiments the elastomer supports 81a, 81b, 81c, 81d, and 81e may be feet. The feet may be sliding resistant feet. For example, the feet may be rubber to help resist sliding. The feet may reduce vibrations that may be transmitted from the oral irrigator 5 to the surface supporting the oral irrigator 5.

The power connection for the oral irrigator 5 may be routed under the bottom plate 80. For example, the power cable may pass through the lower base body 15 via opening 45. The cord may pass through channel 47. The channel 47 may include wall protrusions 46a-c. The power cable may be restrained within channel 47 by the protrusions 46a-c. Each of the protrusions 46a-c may press the power cable against the opposing wall of the channel. This configuration further limits the power cable from being pulled out of the connection, while also preventing the power cord from affecting the stability of the base when it is on a counter top or other support surface. A power plate 49 may be removably attached to the bottom plate 80. The power plate may include the opening 45, the protrusions 46a-c, and/or the channel 47. The power plate may also include an aperture 48 that allows the power cord to pass through the bottom plate 80 and/or the power plate 49 into the internal components of the oral irrigator.

As indicated above the toothbrush receptacle 70 may be formed as part of lower base body 15. For example, the toothbrush receptacle 70 or collar extends outwards from a side of the lower base body 15. The toothbrush receptacle 70 may be operable to secure and/or charge toothbrush 300 and may define a recess that receives the bottom end of the toothbrush and a collar or upper wall that supports the toothbrush wall to help support the toothbrush and prevent the toothbrush from leaning or falling when received in the receptacle 70. The toothbrush receptacle 70 may include an inductive coil 71 electrically connected to the oral irrigator 5. The inductive coil 71 may induce a current in the toothbrush receptacle in order to charge a battery within toothbrush 300. The inductive coil 71 is electrically connected to the same power supply as the irrigator so that the toothbrush and the irrigator may be operated by a single power supply. The toothbrush 300 may include a base end 460 shown through an aperture in the inductive coil 71.

The tube 110 may be routed under the bottom plate 80. Fluid may flow from the reservoir 20 to the pump outlet 112. Fluid entering the pump outlet 112 may flow through the pump outlet 112, into the tube 110, through the handle 200, and ultimately into the tip 350 in order to irrigate or spray fluid into a user's mouth. The tube 110 may pass through an aperture 119 and up to the handle 200.

As liquids may leak from any of the internal valves, pump, tubing, and/or the reservoir, it is possible that those liquids may build up inside housing of the oral irrigator 5. As such the bottom plate 80 may include one or more apertures to drain any liquid build up. For example, with reference to FIG. 5, drain aperture 111 may pass through the bottom plate. In various embodiments, the drain aperture 111 may be positioned near the pump, or valve system, or any other location where leaking liquids are possible. The drain aperture 111 drains liquids and debris away from the pump and/or valve system, which helps to prevent clogging of the various internal components and help to prolong the life of the systems and accurate performance.

Figure 6:
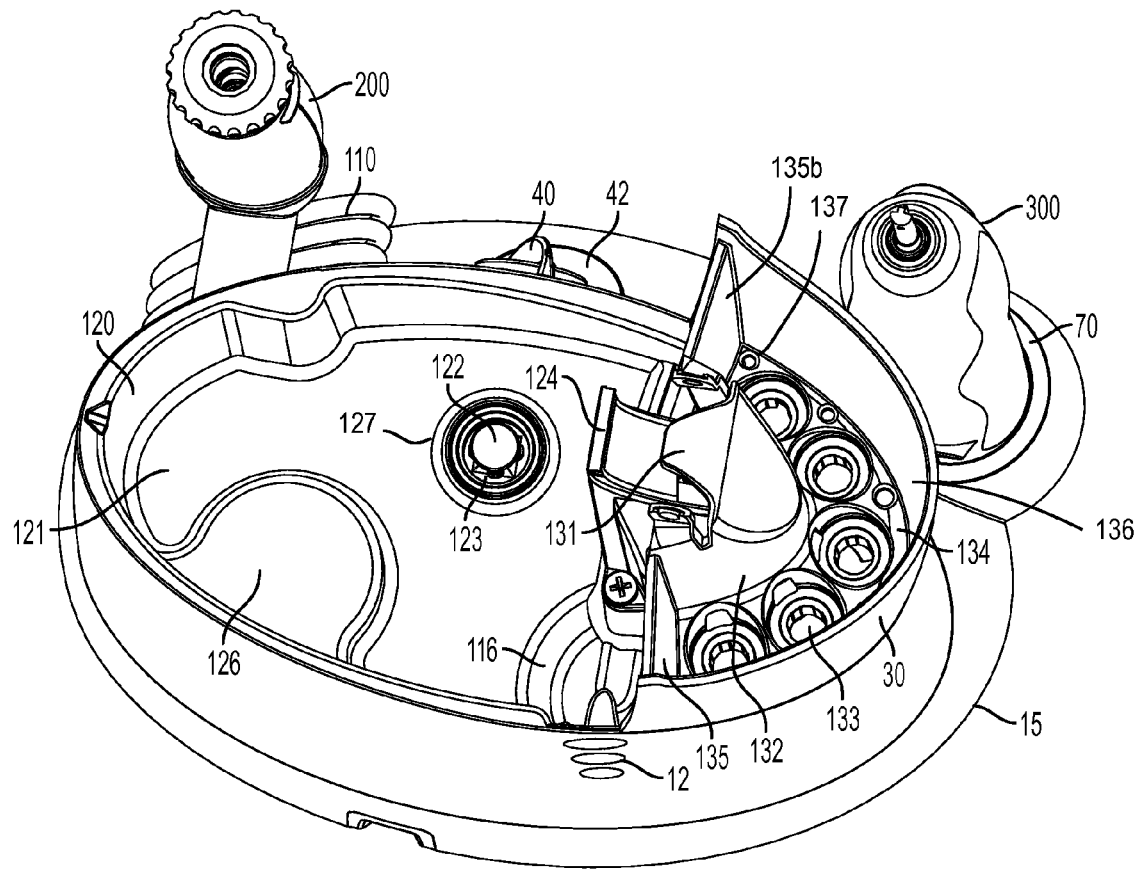
FIG. 6 is a perspective top view of the oral hygiene device of FIG. 1 with lids removed.

FIG. 6 is a perspective top view of the oral hygiene device showing the top of the device with the lids 25, 35 and reservoir 20 removed. Under the reservoir 20, the oral irrigator 5 may include support surface 121. The support surface 121 may support the reservoir and separate the reservoir form the internal components of oral irrigator 5. The support surface 121 may include a raised protrusion 126 that provides a raised surface or bulkhead forming a larger internal volume within housing 10 of the oral irrigator 5, such that a motor may be housed below the support surface 121 and below the reservoir 20. The support surface 121 may include a port aperture 127. A reservoir valve 123 and the reservoir valve head 122 may protrude through the port aperture 127.

The reservoir valve 123 may be generally cylindrical with a generally circular reservoir valve head 122 formed on one end. The reservoir valve head 122 may extend into the reservoir 20. A sidewall 120 may wrap around the perimeter of surface 121 and 126. Together the support surface 121, bulkhead or raised protrusion 126, and sidewall 120 may provide a volume for receiving and supporting reservoir 20. The support surface 121 may include recessed surface 116 that lowers the surface area to a level at or below the lowest of the drain holes 12. The recessed area 116 forms a drainage compartment and allows for water to drain out of drain holes 12 and outside of the oral irrigator 5 to prevent fluid from accumulating beneath the reservoir.

As shown in FIG. 6 with the lid 35 to the accessory compartment 30 removed, the accessory compartment 30 may include an interior wall 132, a reservoir wall 135a, a reservoir wall 135b, an exterior wall 136, and a floor 134. Together the interior wall 132, the reservoir wall 135a, the reservoir wall 135b, the exterior wall 136, and the floor 134 may form the accessory compartment volume 30. The accessory compartment volume may be operable to store spare accessories such as oral irrigator tips or toothbrush tips. The accessory compartment 30 may include a plurality of recesses 133 in the floor 134. These recesses may be sized and shaped the same as one end of an accessory such that the recesses 133 are operable to hold the accessories upright. The accessory compartment 30 may include a plurality of drain holes 137 operable to drain any liquid from the accessory compartment volume. Liquid may drain out of the accessory compartment through drain holes 137 and into the recessed surface 116. The liquids may then flow out of drain holes 12. The accessory compartment 30 may include tab 131. Tab 131 may be curved toward the reservoir.

Figure 7:
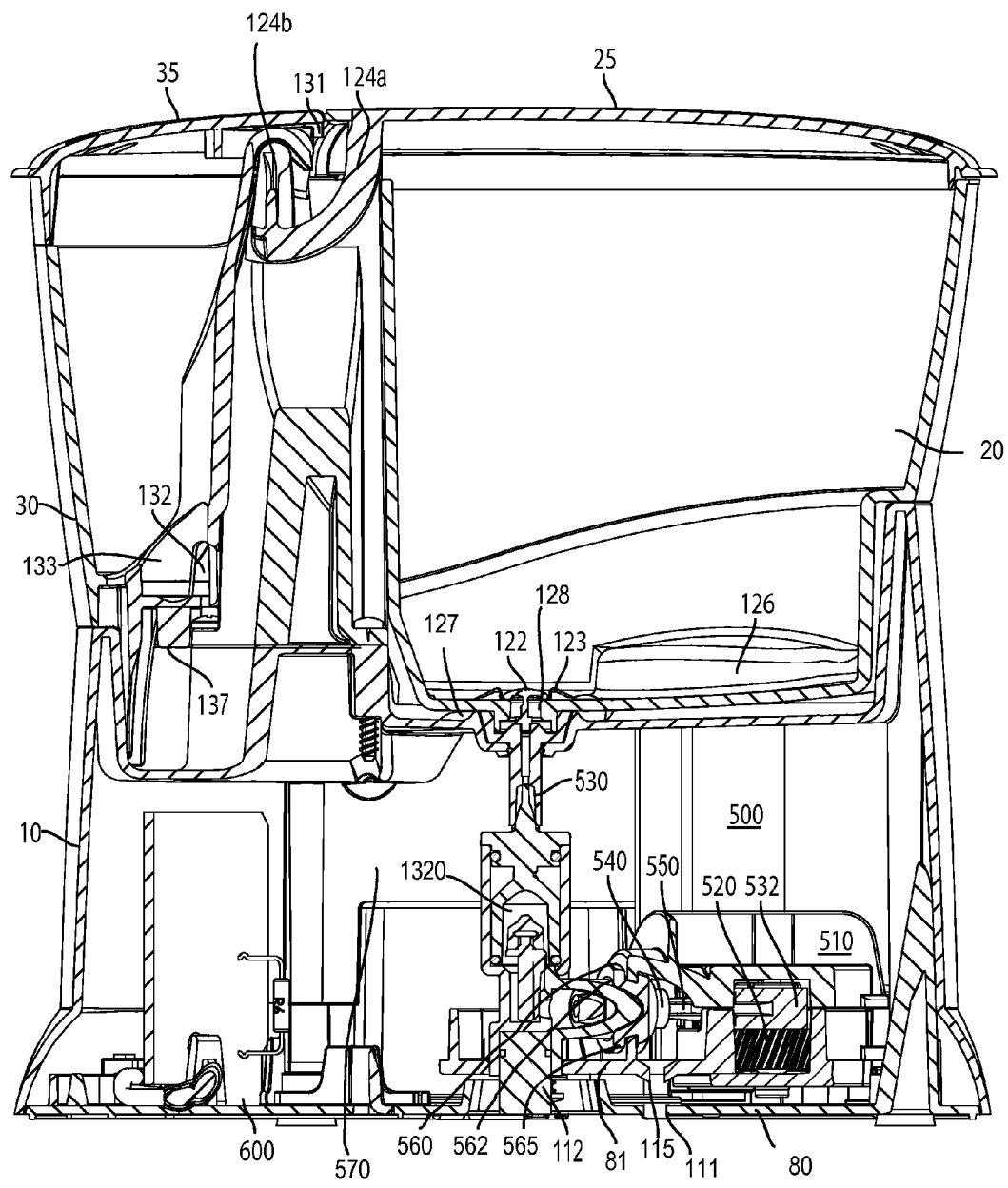
FIG. 7 is a cross-sectional view of the oral hygiene device of FIG. 1 along line 7-7 in FIG. 4.
Figure 7A:
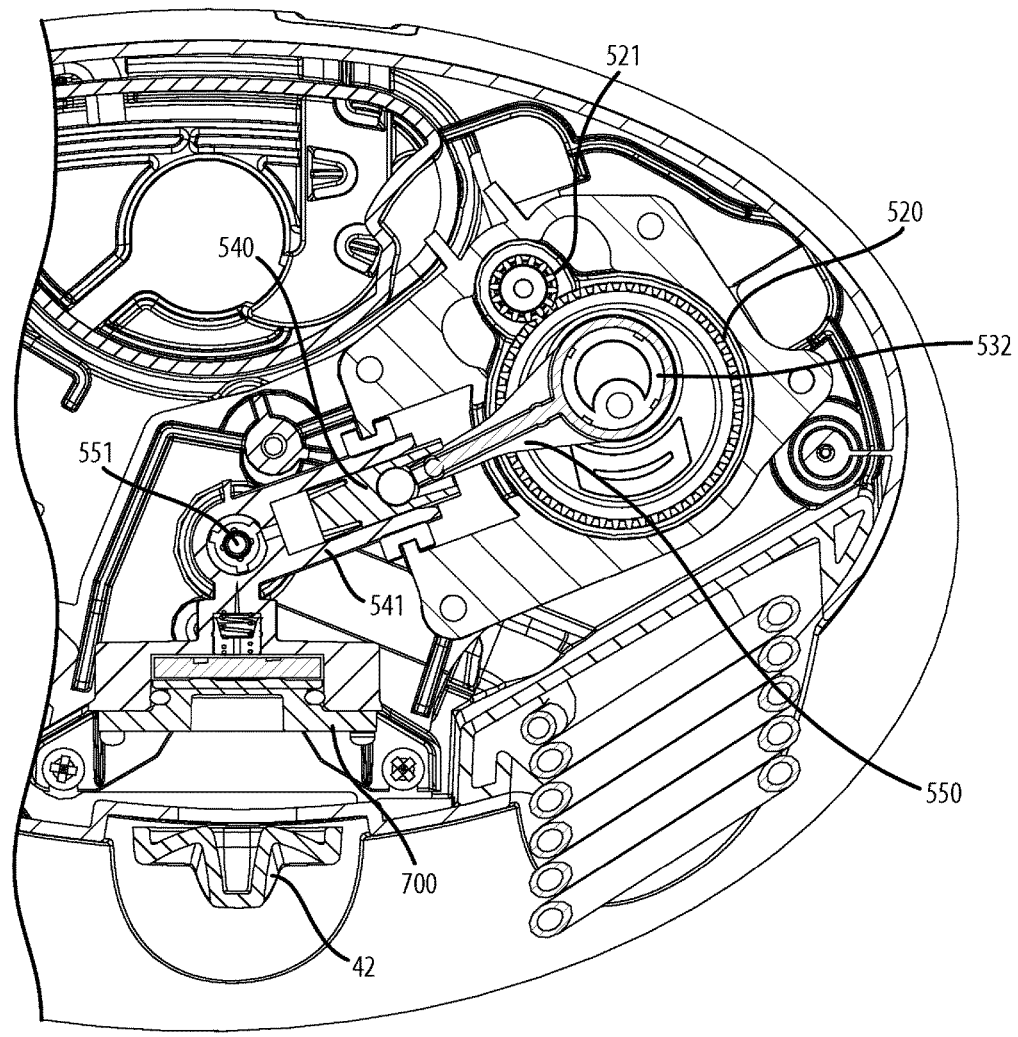
FIG. 7A is a cross-sectional view of the oral hygiene device of FIG. 1 along line 7A-7A in FIG. 2.
Figure 7B:
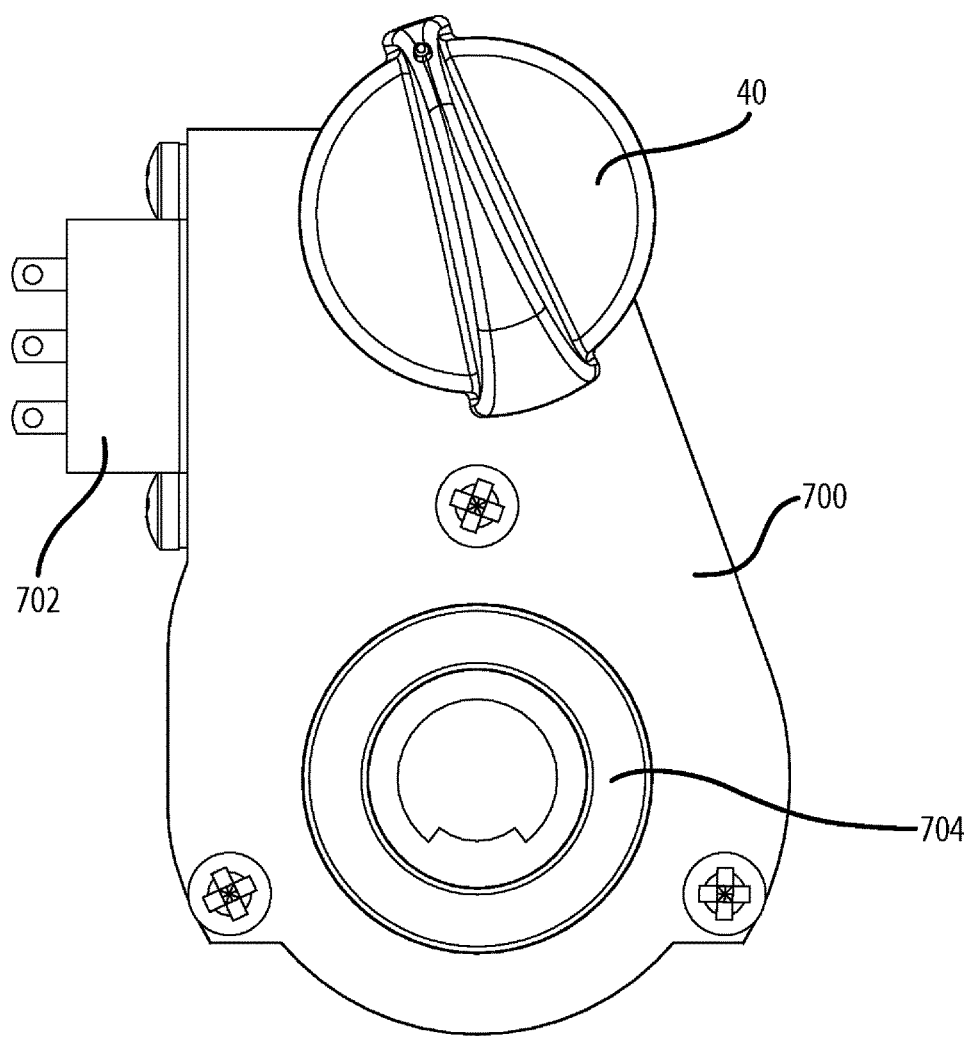
FIG. 7B is a front view of an actuation assembly for the oral hygiene device of FIG. 1.
Figure 7C:
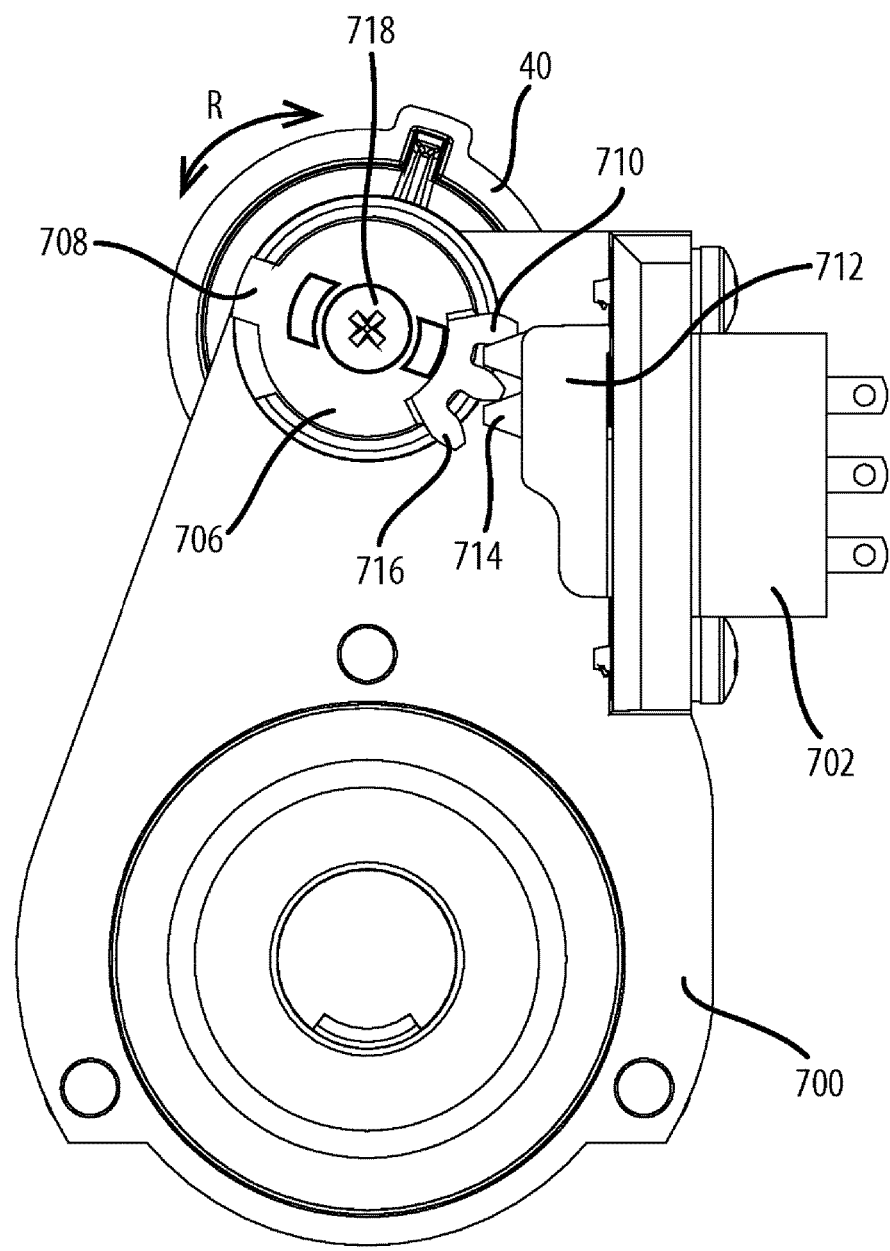
FIG. 7C is a rear view of the actuation assembly of FIG. 7B.

As shown in FIG. 7, reservoir 20 may include a port aperture 128. The reservoir valve head 122 may protrude through the reservoir port aperture 128. The reservoir valve 123 may be in contact with the bottom of the reservoir 20 to seal against the edges of the reservoir defining the port aperture 128. The reservoir valve 123 may be located below and in contact against the reservoir. The valve head 122 protruding through the aperture 128 may allow fluid to flow out of the reservoir and into linkage tube 530. The linkage tube 530 may be connected to the pump valve 1320.

The suction of the pump that allows water to be drawn into and forced out of pump valve 1320 may be created by the pump. The pump includes a pump body 541, a plunger 540 seated within the pump body 541, a connecting rod 550, a driven helical gear 520, an eccentric bushing 532 connected to and extending from the helical gear 520, and a pinion gear 521 connected to the drive shaft of the motor 500. The plunger 540 may be situated perpendicular to the pump valve 1320 and linkage tube 530 within the pump body 541. The plunger 540 may be attached to the connecting rod 550 that is articulated back and forth by the eccentric gear bushing 532. The eccentric gear bushing 532 may be fixedly attached to the connecting rod 550. The eccentric gear bushing 532 may be driven by the helical gear 520. The eccentric relationship between bushing 532 and the helical gear 520 allows the rotational movement of helical gear 520 to be translated into the back and forth movement which drives the plunger 540 via the connecting rod 550. The helical gear 520 may be driven by motor 500 having a corresponding helical pinion gear 521 attached thereto. The motor is located above the gear housing as shown in FIG. 7. This orientation provides for a compact configuration for the pump assembly as the motor and gear housing may be located a relatively small space.

The motor shaft passes through the gear housing to engage the helical pinion gear 521. The motor 500 may be controlled by the circuit card 600. The circuit card 600 may be connected to 40 and 42 such that the circuit card 600 receives user control input from the user. Based on the user control input the circuit is able to power the motor driving the pump to deliver liquid from the reservoir to the handle 200 and ultimately out the tip 150 (see FIG. 1). The circuit card may also control the amount of flow to the tip based on input from 42 that allows for selection of motor speeds, for example, in 10 increments from a low speed to a maximum speed.

In accordance with various embodiments, the motor 500 may be any of a variety of motors including a high voltage DC motor. For example, the motor 500 may be a high voltage direct current motor which operates on 120V alternating current that is rectified to 170V direct current (DC). By operating a high voltage DC motor, the motor is able to be much smaller than a lower voltage DC motor while still being able to operate the pump at similar levels. The decrease in motor size enables the motor to be positioned closer to the circuit card 600 and/or the pump assembly. The decrease in motor size also enables the motor to better fit between the top of the gear housing and the top of the base unit housing under reservoir 20.

As discussed herein, the motor is separated from the pump by helical gear 520 which drives the plunger 540 via the connecting rod 550 within the plunger housing. The plunger 540 and the plunger housing are connected to the pump valve 1320. As such, due to this stack up of components the motor is limited in its position. The motor may be positioned such that its distance from the pump is minimized. Having a smaller motor package aids in minimizing this distance. In various embodiments, the pump valve 1320 may engage the helical gear 520 at a location other than the opposite side of helical gear 520 from where the plunger 540 extends. However, it may be noted that the motor 500 may be positioned opposite of the plunger 540 if minimizing the package size is not a concern. In one example, the pump may engage helical gear 520 between 2 and 3 o'clock as viewed from the bottom of oral irrigator base 10. As the motor is positioned closer to the pump valve 1320 the motor approaches seal 565. A smaller motor 500 housing diameter enables the motor to be positioned closer to seal 565 and thereby be positioned closer to the other components enabling an overall reduction in the size of the oral irrigator base 10. As such, utilizing the high voltage DC motor 500 the motor is positioned such that the overall packaging of the components within oral irrigator base 10 is minimized. The motor and control assembly will now be discussed in more detail. The motor 500 may be a high voltage direct current motor. In one example, the motor 500 operates at 120V alternating current (AC) and is rectified to 170 V direct current (DC), without using a transformer. This allows the motor 500 to be compact and suited for high volume production, as the manufacturing processes for the motor 500 are automated, reducing manufacturing costs for the oral irrigator and improving reliability. In other embodiments, the motor 500 may be a 12 VDC motor with a switching/global power supply.

In accordance with various embodiments, the drive mechanism that includes the helical gear 520, the eccentric bushing 532, the connecting rod 550, and the motor 500 with the helical pinion that engages the helical gear 520, may be enclosed on the bottom by the bottom plate 80. In accordance with other embodiments the drive mechanism may be enclosed on the bottom by a lower chassis 81. The lower chassis 81 may be removably attached to the bottom plate 80. The drive mechanism may also be enclosed by a gear housing 510. Together the lower chassis 81 and the gear housing 510 may form a cavity that contains the drive mechanism. The gear housing 510 is oriented to shield the electronic components from grease and water that may accumulate within the gear housing 510. The gear housing includes an aperture 560 through which the plunger 540 and connecting rod 550 passes from the gear housing into the base housing 570. The base housing 570 encloses the pump and the motor and other components. The interior of the gear housing may be sealed off from the cavity of the base housing 570 with a seal 565. The seal 565 may be an elastomer seal that contacts the gear housing 510 on its external circumference at the aperture 560 and contacts the plunger on its internal circumference 562. The elastomer seal 565 may be operable as a water resistant barrier which limits any contents of the gear housing from contaminating the water utilized in the dental water jet.

As discussed above and illustrated in FIGS. 6 and 7, drain holes 115 and 111 may be positioned below the gear housing cover 510. The drain hole 111 may be a part of a depression and/or an aperture in the bottom plate 80. The drain hole 115 may be a part of a depression and/or an aperture in lower chassis 81. In various embodiments, a depression may surround the drain hole 111, 115 allowing the drain holes to funnel liquids for expulsion from the cavity formed by the gear housing cover 510. For example, bottom surface 80 may include drain hole 111. Above and partially overlapping drain hole 111 may be a second drain hole 115 in the lower chassis 81. However, it may be noted that the holes 111, 115 may be located anywhere suitable for draining the cavity whether they overlap or not. As the pump operates some water from the pump gets into the gear housing and may mix with gear oil and/or debris found in the gear housing (e.g. material that accumulates due to wear on moving components). The drain holes enable drainage of the water, oil, and/or debris from the gear housing and limit the ability of contaminated water from re-entering the system.

As shown in FIG. 7, lid 25 may include a curved tab 124a that extends down to a hinge pivot point 124b. The curved tab 124a allows the lid 25 to pivot at 124b and rotate up and over lid 35 without contact. Lid 35 may include a tab 131 which helps limit the egress of liquid from reservoir 25 into accessory compartment 30.

Components of the Toothbrush

Various embodiments of a mechanically driven, sonic toothbrush system are disclosed herein. The sonic toothbrush system makes use of an electro-mechanical driver (e.g., a DC or AC drive assembly) as an input driver that operates a linkage system that changes the input driver into a desired sonic output motion, which drives the attached toothbrush head at a sonic speed or speeds.

In accordance with various embodiments, the toothbrush systems disclosed herein may provide an input drive system that provides oscillating, sonic-speed toothbrush output motion with an extremely low level of mechanical vibration and noise. The use of "sonic" or "sonic speed" may reference a frequency of oscillation of the brush head of the toothbrush. The frequency may be in the range of frequencies between for example 20 HZ and 20,000 HZ. In various embodiments, the sonic toothbrush system may operate at between 200 and 300 oscillations per second. It may be noted that the toothbrush may also oscillate slower than 200 oscillations per second or faster than 300 oscillations per second.

In accordance with various embodiments, sonic toothbrush system 400 disclosed herein is depicted in FIGS. 8-11. The sonic toothbrush system 400 may include toothbrush end 350 (shown in FIG. 1). The system 400 may include a base end 460 opposite the brush end. The system 400 may include one or more housing sections. Housing 437a may extend between the base end 460 and the brush end 350. The system 400 may also include an over molding 437b which may be over-molded over the first housing 437a. The over molding 437b may include separate over molding portions such as faceplate 412a and side plates 412b/c.

The system 400 may be stood upright on a planar surface, such as a countertop. For example, base end 460 may be flat such that it supports the system 400. An end shaft 430A extends out of the housing 437a at the housing end 404 that is proximal the brush 350. It extends from a system drive assembly 440 enclosed by the housing 437a. A shaft seal 431 extends about the end shaft 430A. Shaft seal 431 is disposed between the housing 437a and the end shaft 430A at the brush end 350. Shaft seal 431 is configured to allow the end shaft 430A to oscillate while limiting fluids from entering into the interior of the housing. A seal bushing 432 may be located axially within the shaft seal 431. An o-ring 437 may be positioned circumferentially around the seal 432 and between the seal 432 and the seal 431. The o-ring may further limit fluids from entering the interior of system 400.

The toothbrush 400 may also include a plurality of indicators mounted on a circuit board 422. The plurality of indicators provide feedback to a user. For example, the indicators may be one or more light emitting diodes (LEDs) that illuminate, change color, and/or pulse to indicate a variety modes. The variety modes may include power, speed, battery charge, or the like. The indicators may include lens cover 420 positioned on the outside of the housing 437a. An LED adhesive tape 423 may be positioned under the lens. The tape 423 may help hold the lens cover 420 in place and create an opaque cover such that the indicator light is only seen through the apertures in the lens tape 423. A lens 424 may be positioned between the lens cover 420 and the circuit board 422. The lens 424 may focus the LED light and/or color the LED light. An LED separator 421 may be positioned between the circuit board 422 and the lens 424. Together the indicator assembly including lens cover 420, LED separator 421, circuit board 422, LED adhesive tape 423, and lens 424 may allow the light from an LED on the circuit board to be transmitted to the exterior of the device to function as an indicator.

The housing 437 may be generally cylindrically shaped to ergonomically fit in the hand of a user. The cylindrical shape may taper in the direction of the brush end 350. The control button 410 may be mounted on a PCB switch 411. A control button 410 and or the PCB switch 411 may be supported on the housing 237*b*. The faceplate 412*a* which may be part of the over molding, may support the control button 410. The control button 410 actuates the electro-magnetic actuator between on and off. In various embodiments, the control button may actuate different ranges of speeds.

The system 400 includes an internal support structure formed by a chassis 465 extending towards the base end 460. An induction coil 425 is wound around a carrier coil frame 461 and is located between the interior side of the end cap 460 and the end of the chassis 465. A rechargeable battery pack 470 is electrically coupled to the induction coil 425. The rechargeable battery pack 470 is supported by the chassis 465. The batteries may be separated from chassis 465 and/or end cap 460 by a spring 463 (see e.g. FIGS. 9 and 10). The spring may maintain a bias in the battery making sure the battery remains continually in contact with its contacts. A carrier coil tape 463 wraps the carrier coil 425. An end cap o-ring 464 is disposed around the outside of the end cap 460 and in between the inside of housing 237*a* and the outside of the end cap 460.

As discussed, the drive assembly 440 is supported off of the chassis 465. The drive assembly 440 is electrically coupled to the battery pack 470 via electrical control circuits of a printed circuit board 422 supported off of the chassis 465. The electrical control circuits are actuated via the control button 410 to cause the drive assembly 440 to operate at different states (e.g., on, off, high speed, low speed, etc.). In one embodiment, the electrical control circuits controlling the drive assembly 440 may include one or more trim pots that allow precise control of frequency and drive assembly speed.

Figure 8A:
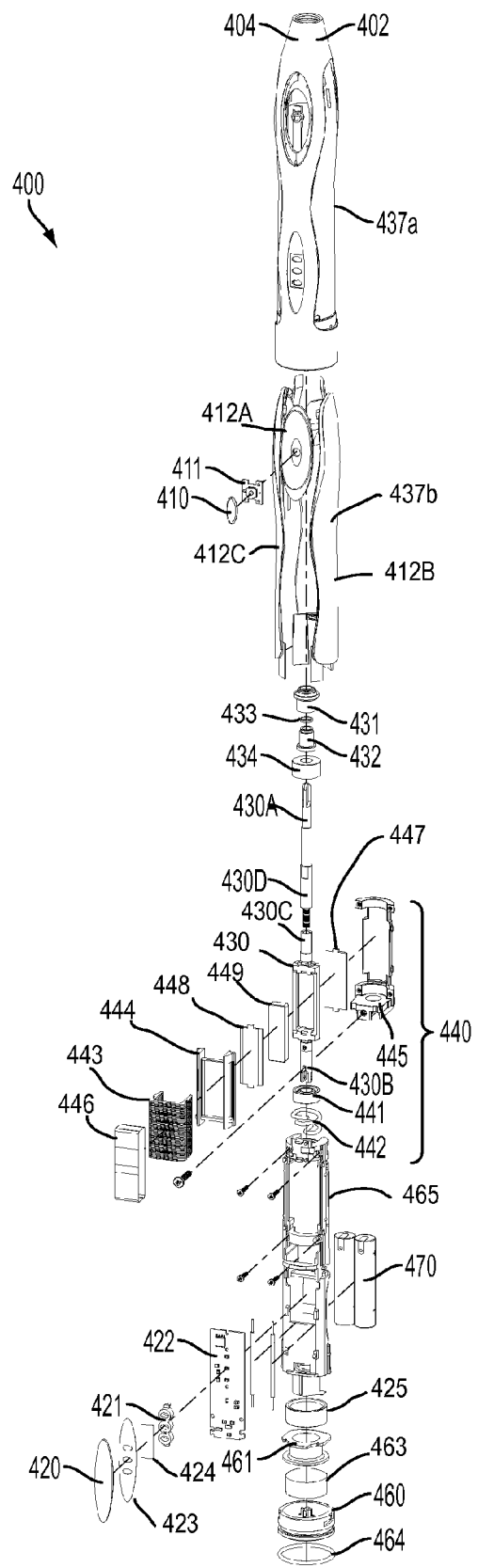
FIG. 8A is an exploded perspective view of the toothbrush.
Figure 9:
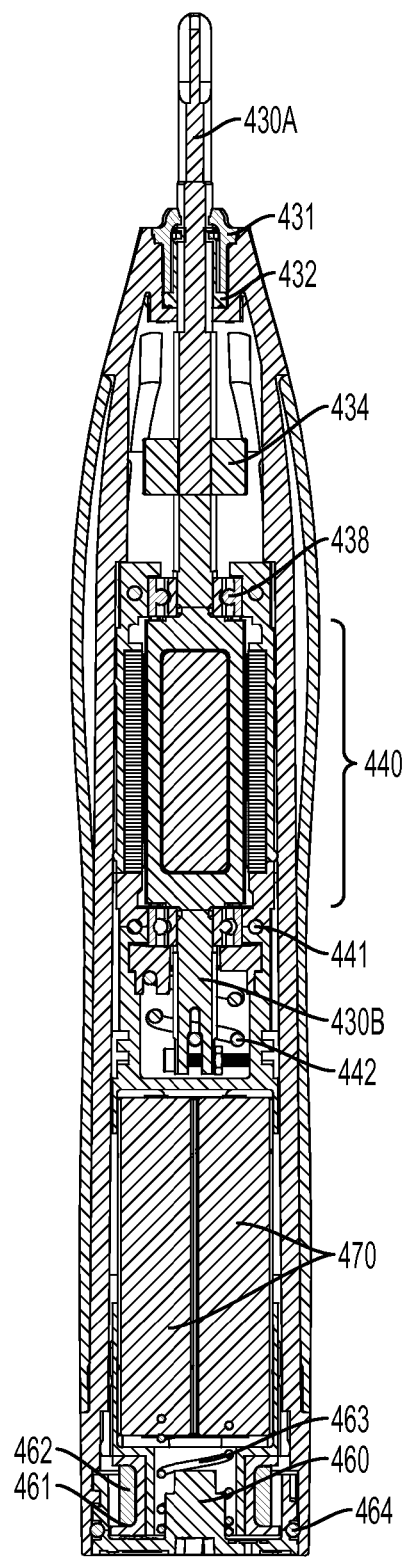
FIG. 9 is a cross-sectional view of the toothbrush along line 9-9 in FIG. 4.

With reference to FIG. 8A, in accordance with various embodiments, the system 400 may include a drive assembly 440. The drive assembly 440 may include a frame support 444 that contains a stator coil 446, core 443, extension magnet 447/448, and armature magnet 449. The frame support 444 may connect core 443 and coil 446 to bracket 445. The coil 446 may be a coil of windings that are wound around the exterior of core 443 such that core 443 passes through the center of the windings. The bracket 445, frame support 444, core 443, and bracket 445 may be positioned together forming a stator. The extension magnet 447, extension magnet 448, armature magnet 449, and shaft frame 430 may be connected together forming an armature.

The shaft frame 430 includes a lower shaft 430B and an upper shaft 430C. A linkage shaft 430D may extend from the upper shaft 430C. The linkage shaft 430D may be separable. For example, the linkage shaft 430D may have a slot cut into it as shown by walls 435,436. The end shaft 430A may extend from the linkage shaft 430D. A thinned portion of end shaft 430A may engage the slot defined by walls 435,436 (See FIG. 8C). The linkage shaft 430D mechanically couples the upper shaft 430C of the drive assembly 440 to the brush 350 to cause the brush 350 to oscillate at sonic speeds.

The drive assembly may include bearing 438/441. A bracket 445 may be removably connected to the frame 465. The bearings 438/441 may be positioned between bracket 445 and frame 465. The bearings 438/441 may restrain shafts 430A-D laterally and longitudinally and allow shafts 430A-D to oscillate axially. The bearings 438/441 may be ball or roller type bearings in some embodiments. The lower shaft 430B may have a slot that engages with a spring 442. The spring may also be fixedly attached to frame 465. The spring may limit the axial rotation of the shafts 430A-D, causing them to be centered in the spring's free state. As the shafts rotate in either direction, the force from the spring against the shafts increase.

Either the linkage shaft 430D or the end shaft 430A includes a balance weight 434. The weight 434 may be operable to counterbalance the components of the drive assembly 440 on which the weights 434 is mounted to reduce noise and vibration in the drive assembly 440. The specific size and location of the weights for each component may then be finalized based on the mass of the material used for a component and the space constraints of the mechanism envelope in order to satisfy the desired resultant center of mass locations.

In exemplary embodiments, various components including the drive shafts 430A-D, bracket 445 and frame 465 may be formed of a polymer material, while the weights 434 may be formed of a metal material such as, for example, stainless steel, tungsten, etc. In other embodiments, the drive assembly components and weights may be formed of any material known or developed in the art.

Components of the Oral Irrigator

FIGS. 12-17 depict various views of the handle 200 of the oral irrigator 5. The handle 200 may be defined by a handle housing 202 comprised of a first handle housing segment 204 and a second handle-housing segment 206 that are joined together to house additional components of the handle 200. Each of the first and second handle housing segments 204, 206 may be comprised of a neck 342*a*, 342*b*, body 340*a*, 340*b*, and conical portion 344*a*, 344*b*. Some or all of the neck 342*a*, 342*b*, body 340*a*, 340*b*, and conical portion 344*a*, 344*b* may be constructed of a rigid material that resists deformation, such as a hard plastic.

FIGS. 13C-D and 17A-B depicts one embodiment of a tip eject mechanism of the handle 200. The tip eject mechanism comprises the valve cap 214, as described above, a latch 212 including a tip eject button 238. The latch 212 may comprise a latch body 308 to which spring 310 are attached via a stud 312. The latch 212 may be in contact with a spring 310 which may extend laterally from a stud 312. The stud 312 may extend from surface 329. The surface 329 may be positioned on the latch 212 opposite the eject button 238. The spring 310 may contact a sidewall 313 of 358*a/b*. The latch 212 may also include stop walls 311, 309 that extend from the body 308. The stop walls 311, 309 may be operable to engage the housing 200 limiting the range of motion of the latch 212. For example, walls 311, 309 may contact support walls 354.

Figure 18A:
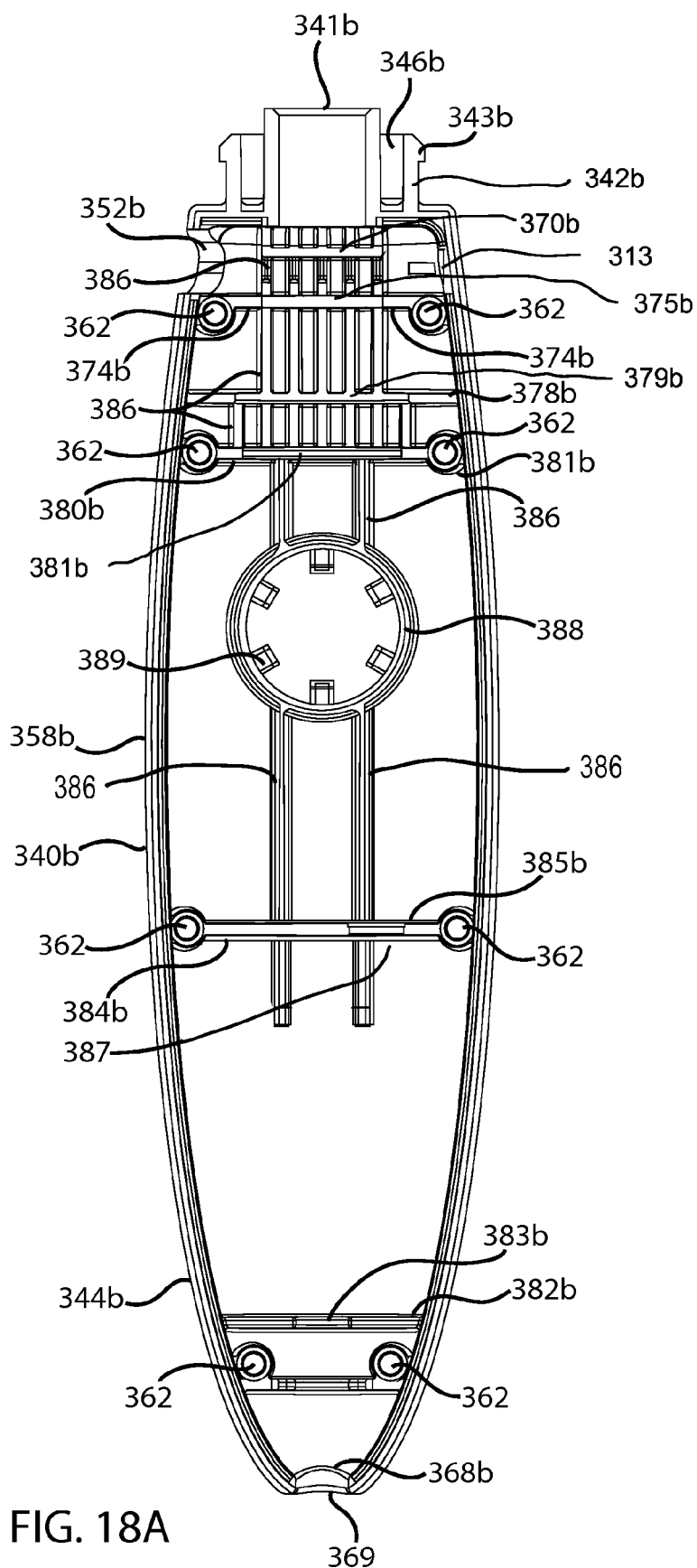
FIG. 18A is an interior view of the front handle housing segment.
Figure 18B:
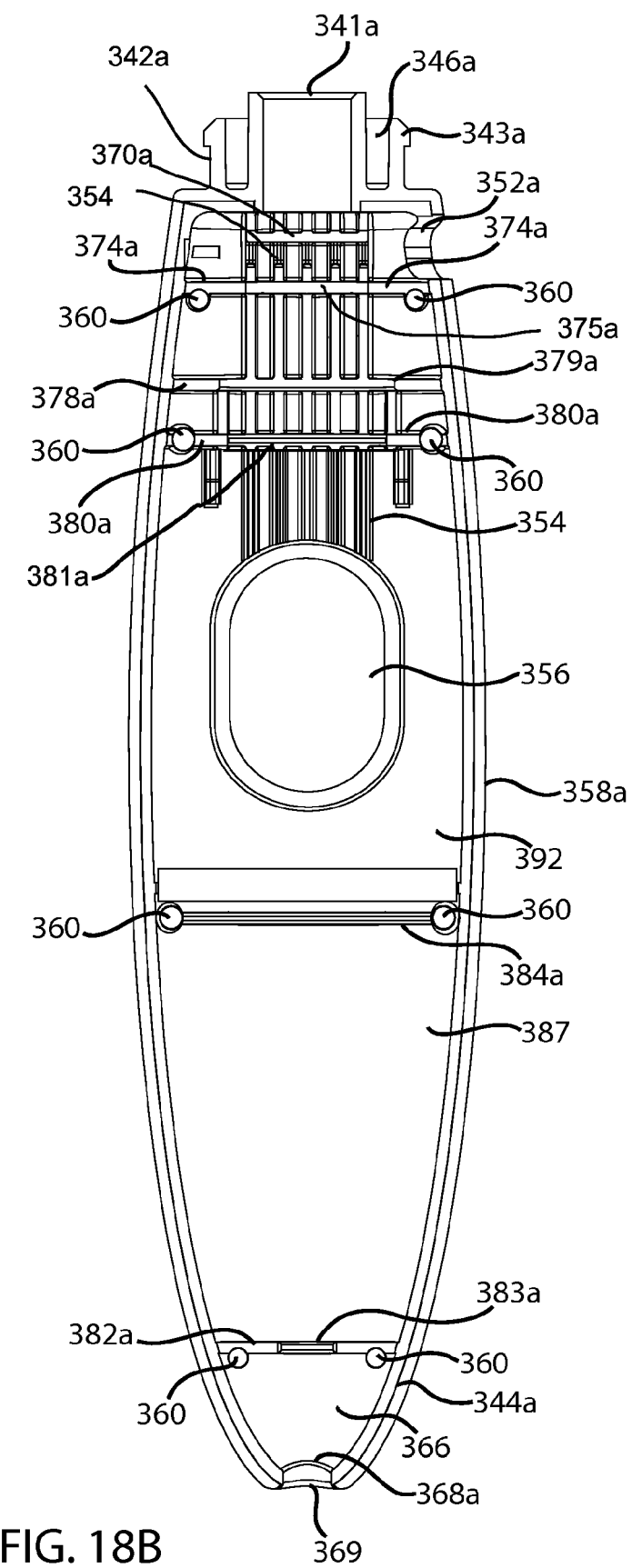
FIG. 18B is an interior view of the rear handle housing segment.
Figure 19:
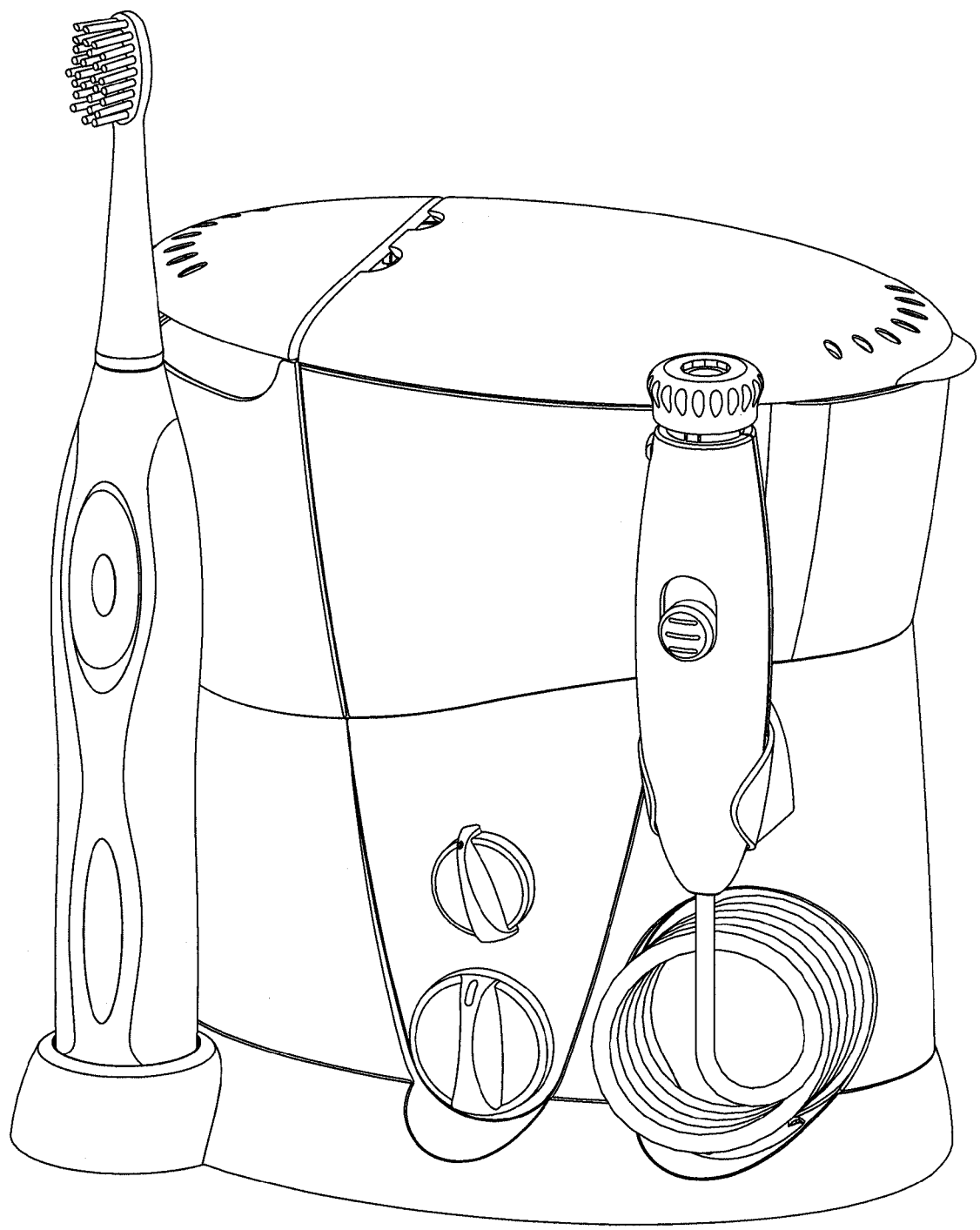
FIG. 19 is a front perspective view of another example of a combination oral hygiene device.
Figure 20:
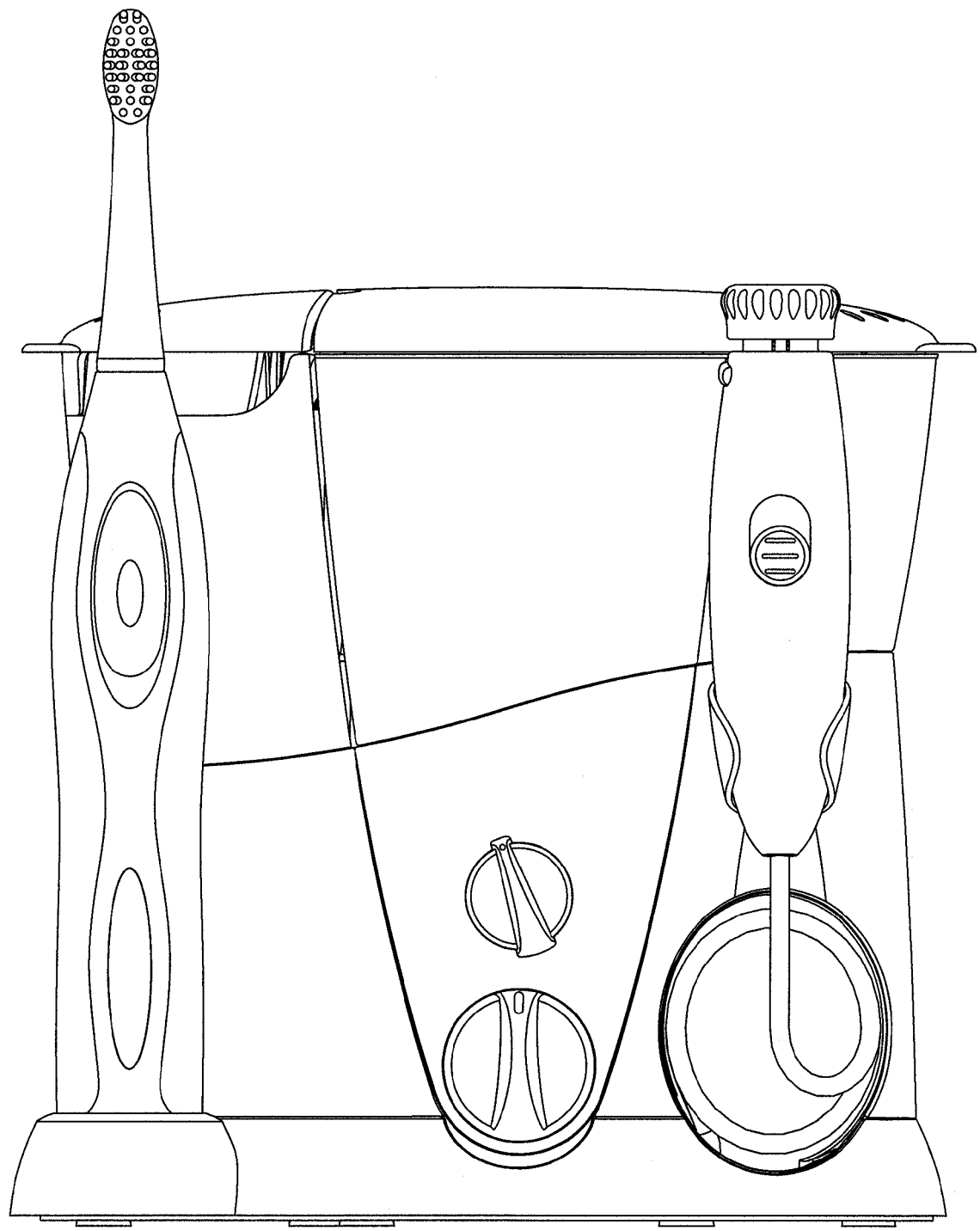
FIG. 20 is a front elevation view of the combination oral hygiene device of FIG. 19.
Figure 21:
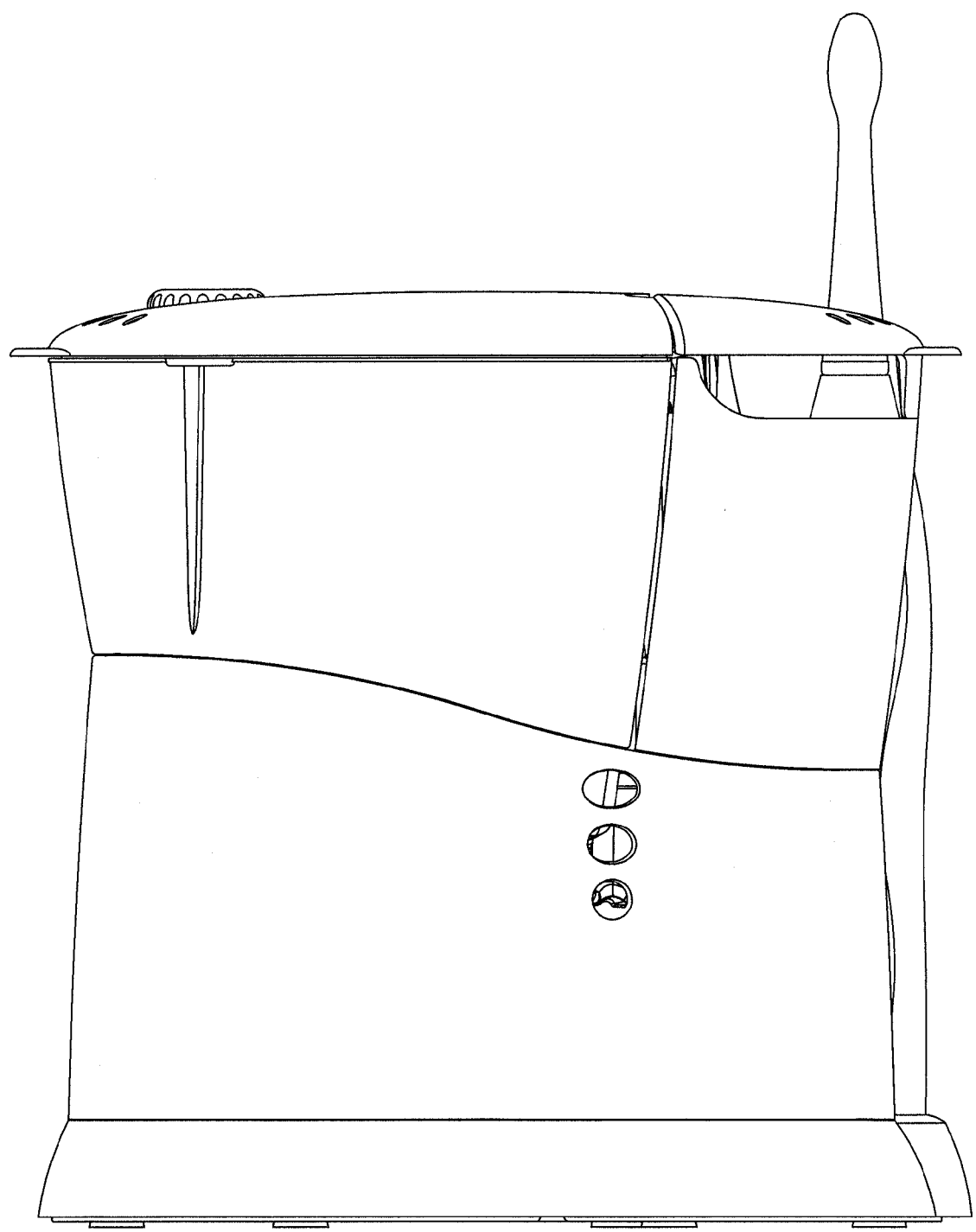
FIG. 21 is a rear elevation view of the combination oral hygiene device of FIG. 19.
Figure 22:
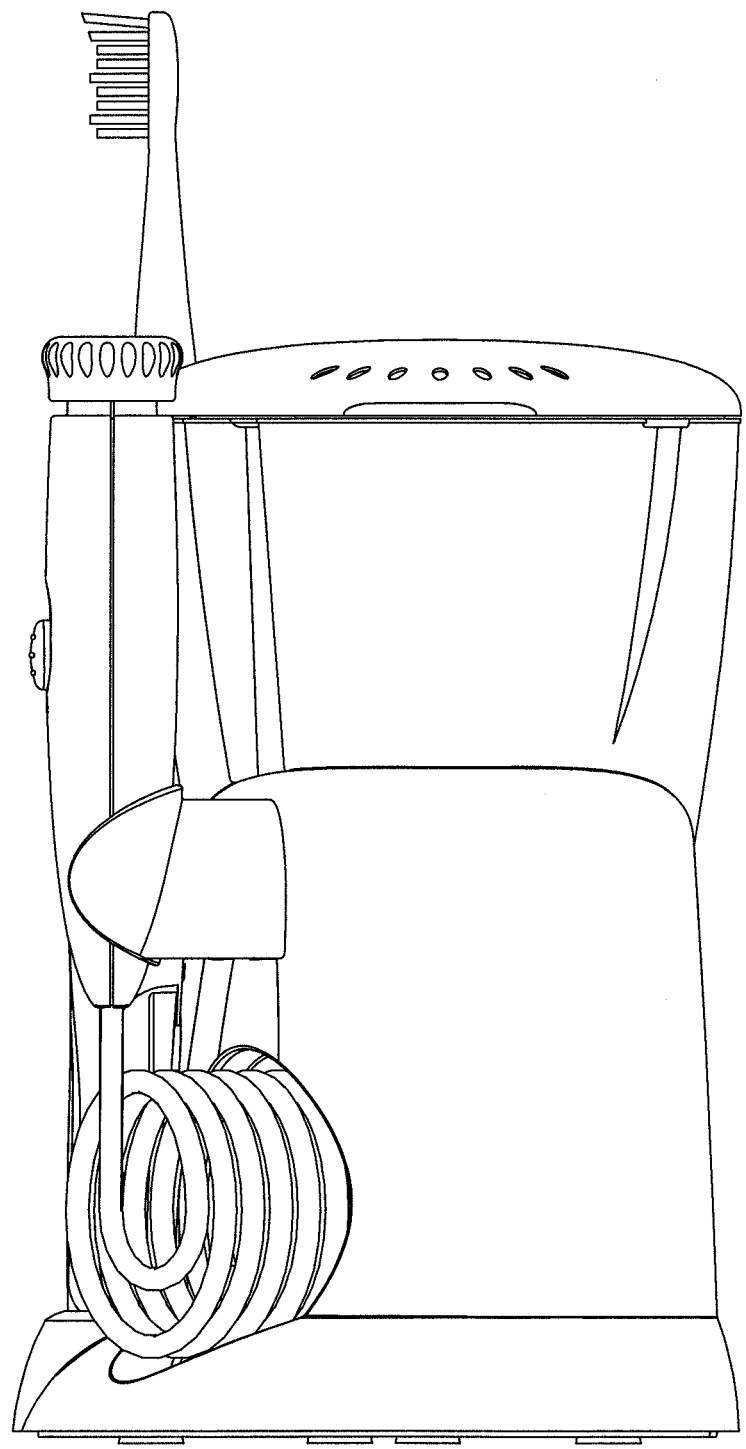
FIG. 22 is a right side elevation view of the combination oral hygiene device of FIG. 19.
Figure 23:
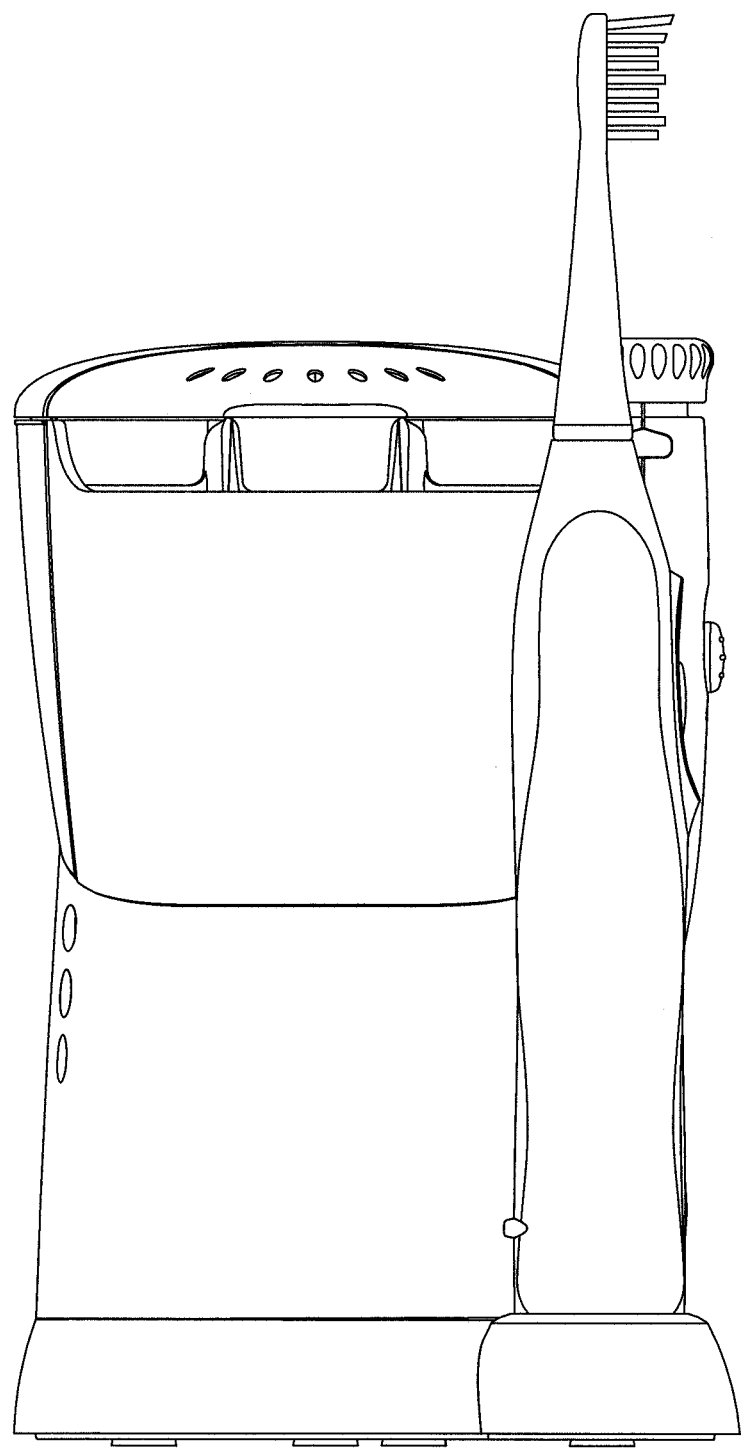
FIG. 23 is a left side elevation view of the combination oral hygiene device of FIG. 19.
Figure 24:
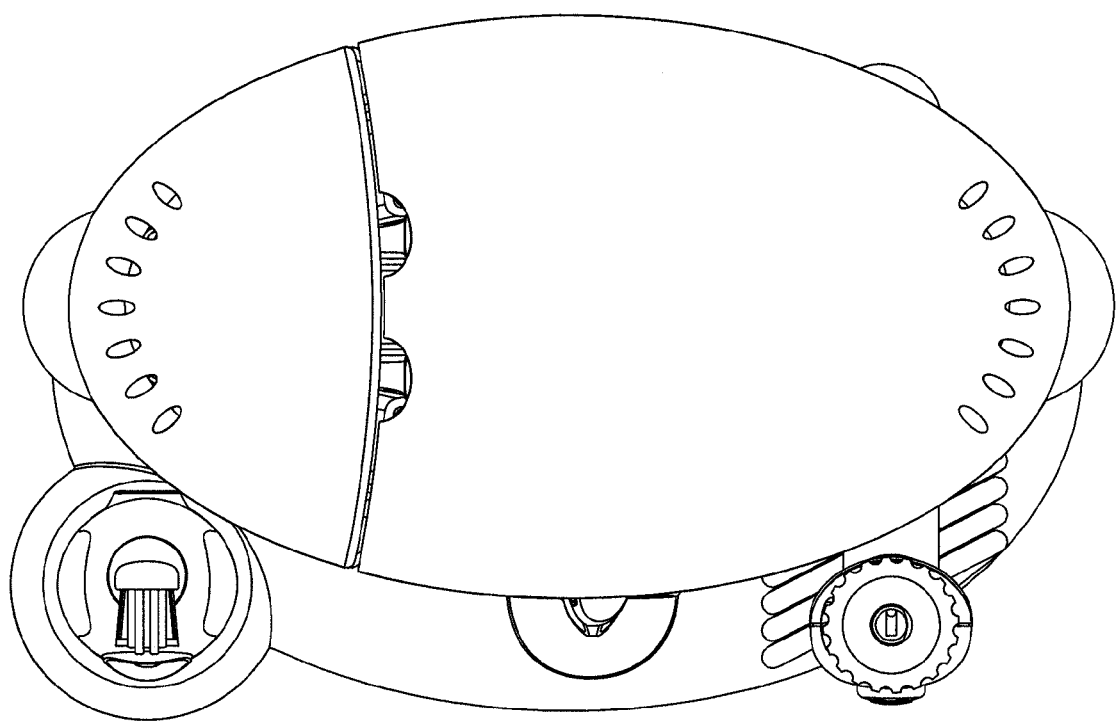
FIG. 24 is a top plan view of the combination oral hygiene device of FIG. 19.
Figure 25:
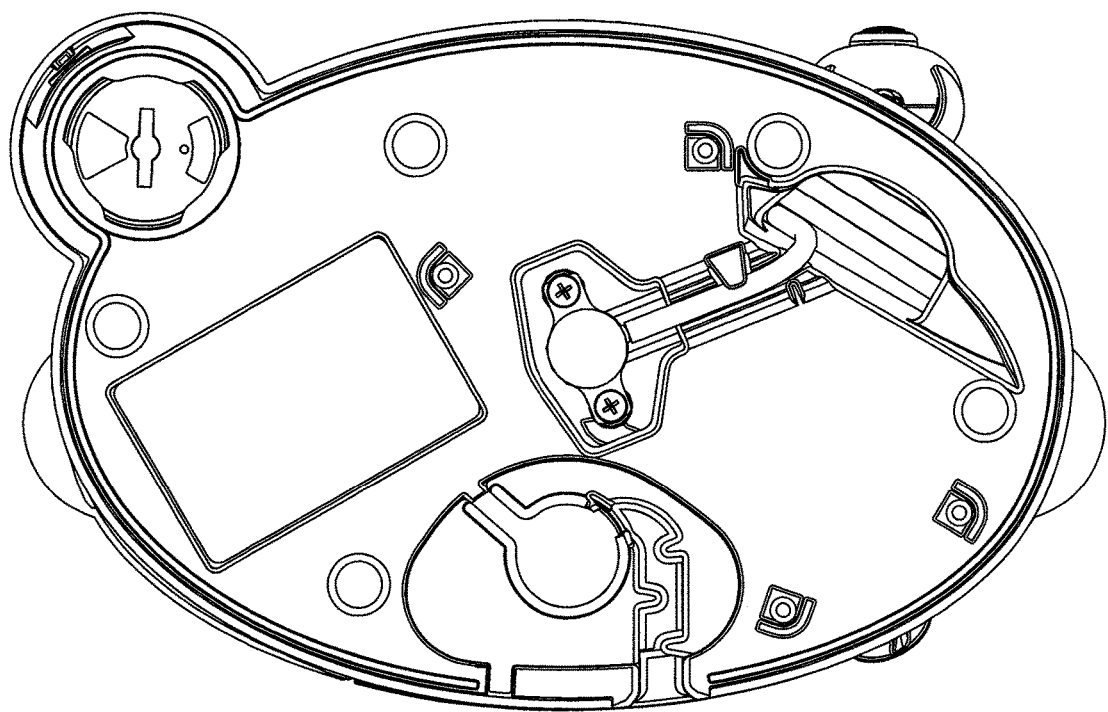
FIG. 25 is a bottom plan view of the combination oral hygiene device of FIG. 19.

As depicted in FIGS. 13C-D and 17A-B, a top surface 321 of the latch body 308 comprises guide walls 320 that extend partially around the perimeter of the latch body 308. The guide walls 320 extend laterally away from the aperture 319 to form a part of latch body 308. The guide walls 320 may be a uniform or variable width. The width may be great enough at a given point along a body 308 that, when the handle 200 is assembled, the guide walls 320 rest on or between the second interior shelves 370*a*, 370*b*, 374*a*, 374*b* as shown in FIG. 18A-B.

The latch body 308 also comprises an interior lip 318 that extends generally radially inward above an interior wall 316. The interior lip 318 may be chamfered, as depicted in FIG. 17B, or may be smooth. The perimeter defined by the interior wall 316 may be an irregular oval or bell shape or may be any other shape. The shape of the perimeter may be complementary to the tip 150 that is received in the tip-receiving aperture 319. The latch 212 may be positioned adjacent to the valve cap 214 such that the latch 212 may receive the tip 114 that passes through the tip-receiving aperture 319. The interior walls 316 may define a passage, which define the tip-receiving aperture 319.

In the embodiment depicted in FIGS. 13A-E and 17A-B, the latch 212 may include a tip eject button 238. The button 238 may also have a ribbed or grooved outer surface which may help provide traction for a user's finger or hand to more easily operate the tip eject button 238 and prevent the user's finger or hand from slipping off the tip eject button 238.

As described in more detail below and shown in FIG. 12-13, the handle 200 may include a generally circular collar 208, the exterior surface of which may be grooved or ribbed. The interior surface of the collar 208 may define a first tip-receiving aperture 209 for receiving the tip 150. A first spring 210 may be positioned in or under the collar 208, such as by being inserted into an annular wall defining the interior cavity of the collar 208 or molded into the collar 208 (see FIGS. 13A-I). A polygonal wall 129 may extend longitudinally above tip-receiving aperture 209. The tip 150 may engage the polygonal wall 129 limiting the movement of the tip 150 in a rotating axial direction with respect to the handle 200.

The neck 342a, 342b of each handle-housing segment 204, 206 comprises a tip receiving portion 341a, 341b configured to receive a tip 150. The neck 342a, 342b also includes an annular recess 346a, 346b for receiving the first spring 210. When the handle 200 is assembled, the collar 208 may be positioned over the neck 342a, 342b and may be secured to the handle housing 202 by several arcuate tabs 345 extending radially inward from a sidewall of the collar 208 that capture an annular lip 343a, 343b of the neck 342a, 342b (see FIGS. 13A-I). The arcuate tabs 345 of the collar 208 may be separated from the bodies 340a, 340b of the handle housing segments 204, 206 by a gap 347, the span of which may be decreased by depressing the collar 208 towards the bodies 340a, 340b.

Figure 12:
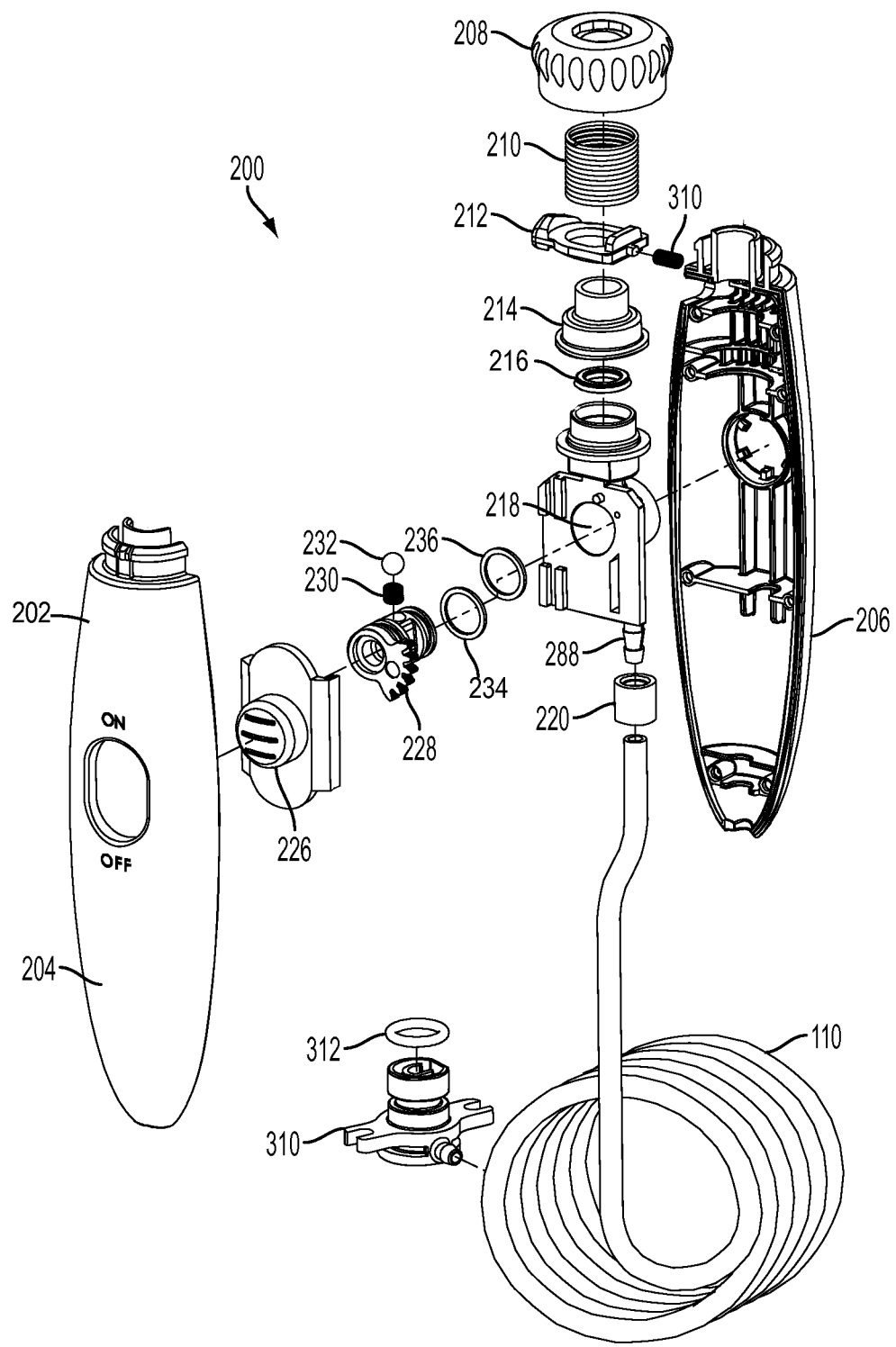
FIG. 12 is an exploded perspective view of the oral irrigator handle.

With reference to FIGS. 12 and 18A-B the bodies 340a, 340b of the first and second handle housing segments 204, 206 together define a handle cavity 392 in which a latch 212, valve cap 214, valve body 218, and tube 110 may reside. The first handle housing segment 204 may include first, second, third, fourth, fifth, and sixth shelves 370a, 374a, 378a, 380a, 382a, and 384a, respectively, for aligning, receiving, retaining, and/or supporting the latch 212, valve cap 214, valve body 218, and tube 110 within the handle cavity 392 (see FIGS. 13A-I And 18A-B). The shelves 370a, 374a, 378a, 380a, 382a, and 384a generally extend in a horizontal plane with respect to a longitudinal axis of the handle 200, and radially inwardly from the first handle housing segment 204 within the handle cavity 392. Each shelf 370a, 374a, 378a, 380a, 382a, and 384a, may align with a mating shelf 370b, 374b, 378b, 380b, 382b, and 384b, respectively, extending from the second handle housing segment 206 when the handle 200 is assembled. As in the first handle housing segment 204, the shelves 370b, 374b, 378b, 380b, 382b, and 384b of the second handle housing segment 206 help align, receive, retain, and/or support the latch 212, valve cap 214, valve body 218, and tube 110 within the handle cavity 392 (see FIGS. 13A-I). Also as in the first handle housing segment 204, the shelves 370b, 374b, 378b, 380b, 382b, and 384b of the second handle housing segment 206 generally extend in a horizontal plane with respect to the longitudinal axis of the handle 200, and radially inwardly from the second handle housing segment 206 within the handle cavity 392.

The depth of the shelves 370a,b, 374a,b, 378a,b, 380a,b, 382a,b, and 384a,b may be the same or different, and the depth of a given shelf may vary along the width (the lateral dimension) of that shelf. Each shelf 370a,b, 374a,b, 378a,b, 380a,b, 382a,b, and 384a,b may have an edge facing the handle cavity 392. The edge may be interrupted by a recessed portion 373a,b, 375a,b, 379a,b, 381a,b, and 385a,b. Some of the recessed portions, e.g. 379a,b, 381a,b, and 385a,b, may be formed as a semicircular notch. Opposing semicircular notches 379a,b, 381a,b, and 385a,b align to form generally circular apertures for receiving a portion of the latch 212, valve cap 214, valve body 218, or tube 110.

The bodies 340a, 340b of the first and second handle housing segments 204, 206 may also include vertical support walls 354, 386 for supporting the shelves 370a,b, 374a,b, 378a,b, 380a,b, 382a,b, and 384a,b. The vertical support walls 354, 386 may also help to align, receive, retain, and/or support the latch 212, valve cap 214, valve body 218, and hose 110 within the handle cavity 392. The vertical support walls 354, 386 may be as deep as the shelves 370a,b, 374a,b, 378a,b, 380a,b, 382a,b, and 384a,b they abut, or may be less deep. The vertical support walls 354, 386 may be positioned to engage stop walls 311, 309 on latch 212. By constraining the stop walls 311, 309 between the vertical support walls 354, 386 and a sidewall 313 the lateral motion of the latch 212 may be limited.

The bodies 340a, 340b of the first and second handle housing segments 204, 206 may also include other interior walls for aligning, receiving, retaining, and/or supporting components within the handle cavity 392. For example, the second handle housing segment 206 may include a circular wall 388 with adjacent counterforts 389 extending radially inward from the circular wall 388 for aligning, receiving, retaining, and/or supporting a valve gear chamber 282 of the valve body 218.

With further reference to FIGS. 12, 17A-B, one or more pegs 360 may extend from the interior surface of one of the handle housing segments 204, 206 (e.g., in the depicted embodiment, the second handle housing segment 206) proximate the shelves 374a, 380a, 382a and 384a. Each peg 360 may extend into the handle cavity 392 beyond a plane defined by a circumferential edge of the exterior wall 358a of the second handle-housing segment 204. Each peg 360 may be adapted to mate with a corresponding boss defining holes 362 in the interior shelves 374b, 380b, 382b and 384b, respectively, of the opposing handle housing segment 206 (e.g., in the depicted embodiment, the first handle housing segment 204). The pegs 360 and the holes 362 may be dimensioned such that each peg 360 will relatively snugly fit within its corresponding hole 362. The friction resulting from this fit may resist decoupling of the handle housing segments 204, 206. Alternatively and/or additionally, the first and second handle housing segments 204, 206 may be joined using glue, epoxy, fasteners, sonic welding, any other known method for joining two items, or by a combination of known methods. For example, the pegs 360 may be glued or adhered within the holes 362.

As depicted in FIGS. 12, 13A-I, and 18A-B the outer surface of the exterior walls 358a, 358b of the first and second handle housing segments 204, 206 may each define a C-shaped depression forming an opening 352a, b when the two housing segments 204, 206 are assembled. The tip eject button 238 may protrude laterally through the opening 352a, b such that a user can depress the button 238 from the exterior of the handle 200. The tip eject button 238 is both retained within the opening 352a, b and can slide laterally within the housing 200 9.

With reference again to FIG. 17B, the first handle housing segment 204 may also include a control actuator aperture 356 for receiving a pause control actuator 226. In the depicted embodiment, the control actuator aperture 356 is oval-shaped, but may be any shape. By placing the pause control actuator 226 on the handle 200, the user may more easily change settings or pause the oral irrigator 5 while using the oral irrigator 5.

With reference to FIGS. 12 and 18A-B, the conical portion 344a, 344b of each handle housing segment 204, 206 comprises a semicircular notch 368a, 368b and the notches 368a, 368b together define a substantially circular second tube aperture 369 through which the tube 110 passes. The conical portions 344a, 344b may also be configured to secure a liner of a strain relief. The strain relief for the tube 110 may be constructed of a flexible or deformable material, such as an elastomer. The strain relief may be designed to isolate stress on the tube 110 at the region where the tube 110 enters the handle housing 202 at the second tube aperture 369 to prevent transfer of any strain on the tube 110 to where the tube 110 connects to the valve body 218. The strain relief may fit snugly around the tube 110 at a first tube aperture in the strain relief through which the tube 110 passes. The strain relief may be formed about a liner that aids in connection of the strain relief to the handle 200. The liner may be constructed a relatively rigid material such as a plastic, similar to or the same as the material forming the handle 200. The liner may further be formed with features as further described below for engagement with the handle 200. The liner may be shorter than the length of the strain relief to allow for flexibility in the area of engagement between the strain relief and the tube 110. The strain relief may be over-molded on the liner or otherwise secured thereto, such as by gluing, fastening, any other known method for joining two items. The strain relief may fit snugly around the liner.

With reference to FIGS. 12-13 and 14A-14C, after passing through the tube aperture 369, the tube 110 may pass through another tube aperture 387 formed by mating of the semicircular notches 385a, 385b in the eighth interior shelves 384a, 384b of the first and second handle housing segments 204, 206.

A valve body 218 may be positioned within the handle housing 202 above a terminal end of the tube 110. The valve body 218 may be considered to have a lower portion 276 and an upper portion 275 connected to each other by a neck 277. A fluid conduit 286 may extend downward from the lower portion 276 of the valve body 218 in a direction generally aligned with the longitudinal axis of the handle 200.

The end of the tube 110 fits over a barbed tip 288 of the fluid conduit 286 that extends from the valve body 218. A hollow cylindrical tube clamp 220 may clamp the end of the tube 110 against the fluid conduit 286. The tube clamp 220 may be positioned proximate to, and may be supported by, the eighth interior shelves 384a, 384b. A first fluid inlet 289 in the terminus of the barbed tip 288 provides fluid communication between the tube 110 and the valve body 218.

The lower portion 276 of the valve body 218 also comprises a valve chamber 282 on one face, and a valve chamber aperture 283, walls 300, and a post 296 on an opposing face. The walls 300 define a slot 302. The exemplary embodiment of FIGS. 14B and 14C has four walls 300 that are generally rectangular cuboids in shape and are each shorter than the length of the lower portion 276 of the valve body 218, but any number, shape, and length of walls 300 may be included. The post 296 is generally cylindrical in shape and extends normally from the opposing face, but may be any size and shape. In some embodiments, the lower portion 276 also includes a generally circular aperture 298 and an elongate well 304. The lower portion 276 of the valve body 218 is connected to the upper portion 275 at a neck 277.

Figure 14B:
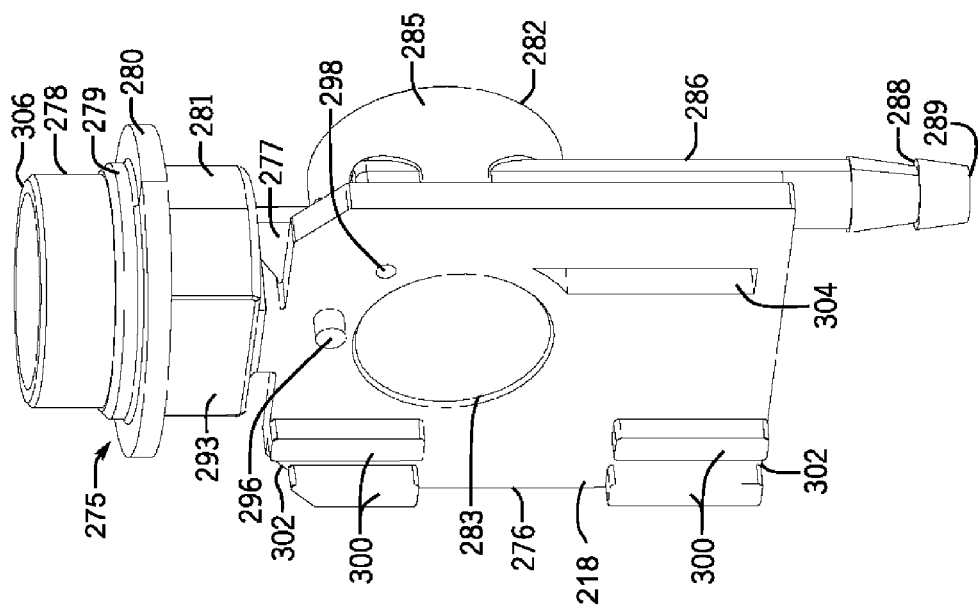
FIG. 14B is a perspective front view of the valve body.
Figure 14A:
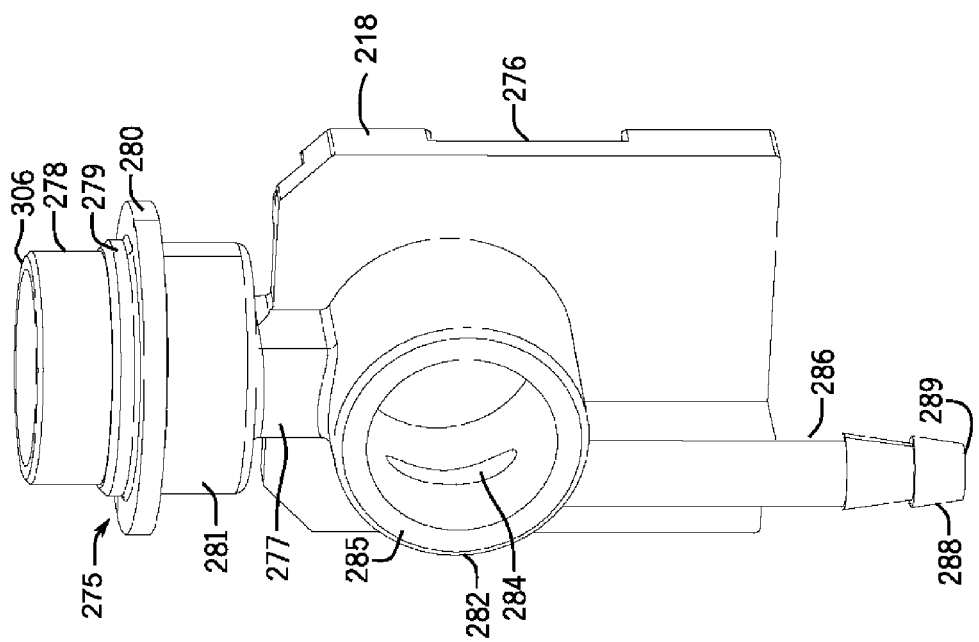
FIG. 14A is a perspective rear view of the valve body.

The valve chamber 282 is generally cylindrical and extends away from the valve body 218 toward the second handle-housing segment 206 in a direction generally aligned with a horizontal axis of the handle 200. The valve chamber 282 is configured to receive a valve spool 228. A second fluid inlet 284 is formed within the chamber wall 285, opens into the valve chamber 282, and is positioned to be in fluid communication with the fluid conduit 286. In the embodiment of FIG. 14A, the second fluid inlet 284 is generally oblong, but may be any size and shape.

A fluid outlet 294 is formed within the chamber wall 285 at a location separated from the second fluid inlet 284, for example, in the direction of the neck 277. The fluid outlet 294 is positioned to be in fluid communication with a well 290 formed in the neck 277 of the valve body 218.

Figure 14C:
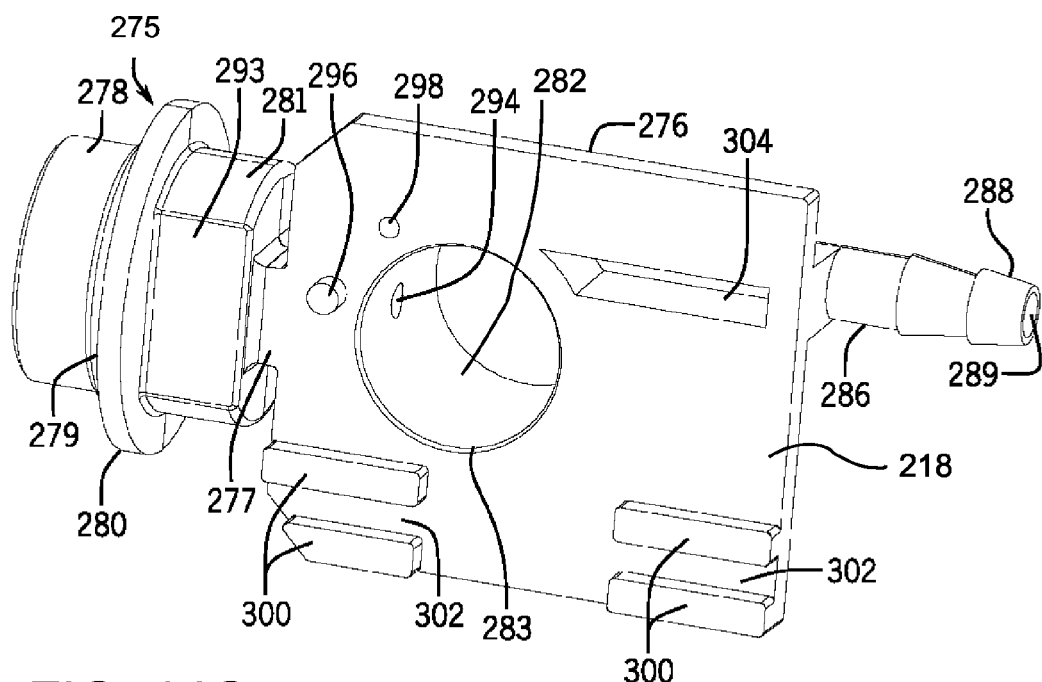
FIG. 14C is a perspective bottom view of the valve body.

The valve spool 228 is received in the valve chamber 282 through a valve chamber aperture 283 on the opposing face of the valve body 218 from which the valve chamber 282 extends. In the embodiment of FIGS. 14B and 14C, the valve chamber aperture 283 is generally circular in shape, but may be any shape that accommodates the valve spool 228.

As depicted in FIGS. 14A-14D, the upper portion 275 of the valve body 218 comprises a mouth 278, a first rim 279, a second rim 280, and a tip receiving portion 281. Each of the mouth 278, first rim 279, and second rim 280 may be generally circular in shape. The second rim 280 may have a greater circumference than the first rim 279, such that the upper portion 275 of the valve body 218 has a stepped outer surface.

Figure 13C:
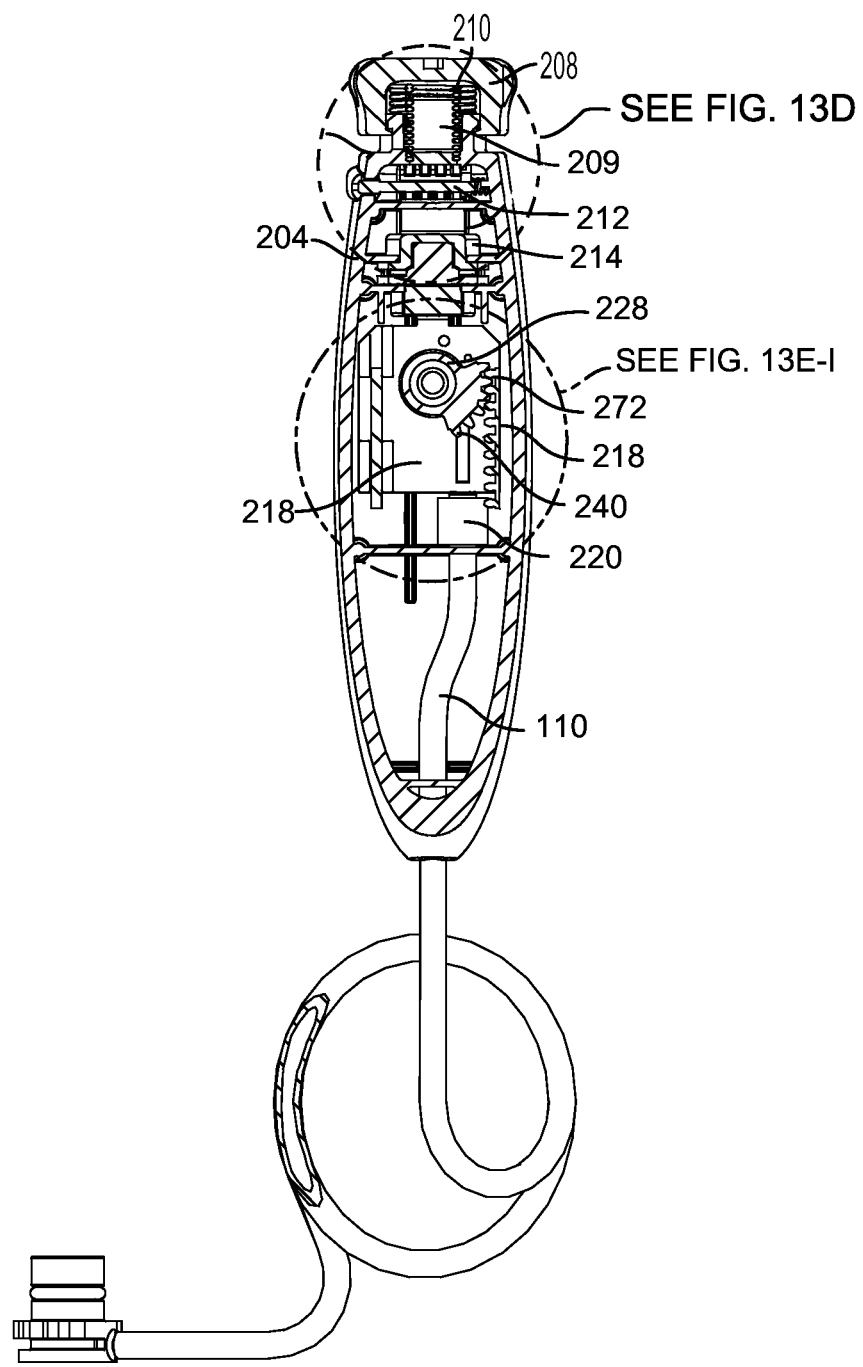
FIG. 13C is a cross-sectional view of the irrigator handle along line 13C-13C in FIG. 4.
Figure 13D:
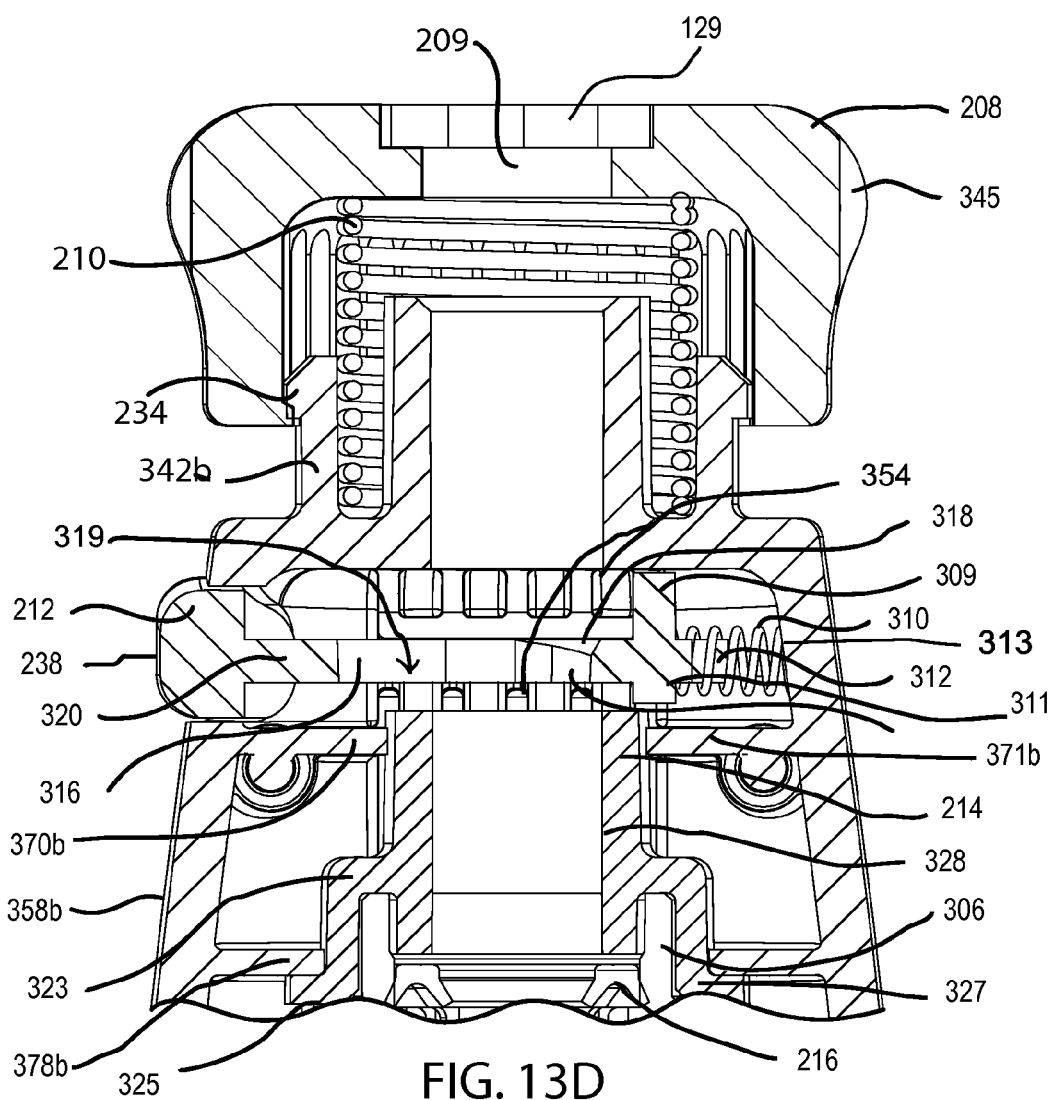
FIG. 13D is a sectional view of the cross-sectional view of FIG. 13C depicting the oral irrigator handle along line 13C-13C in FIG. 4.
Figure 13E:
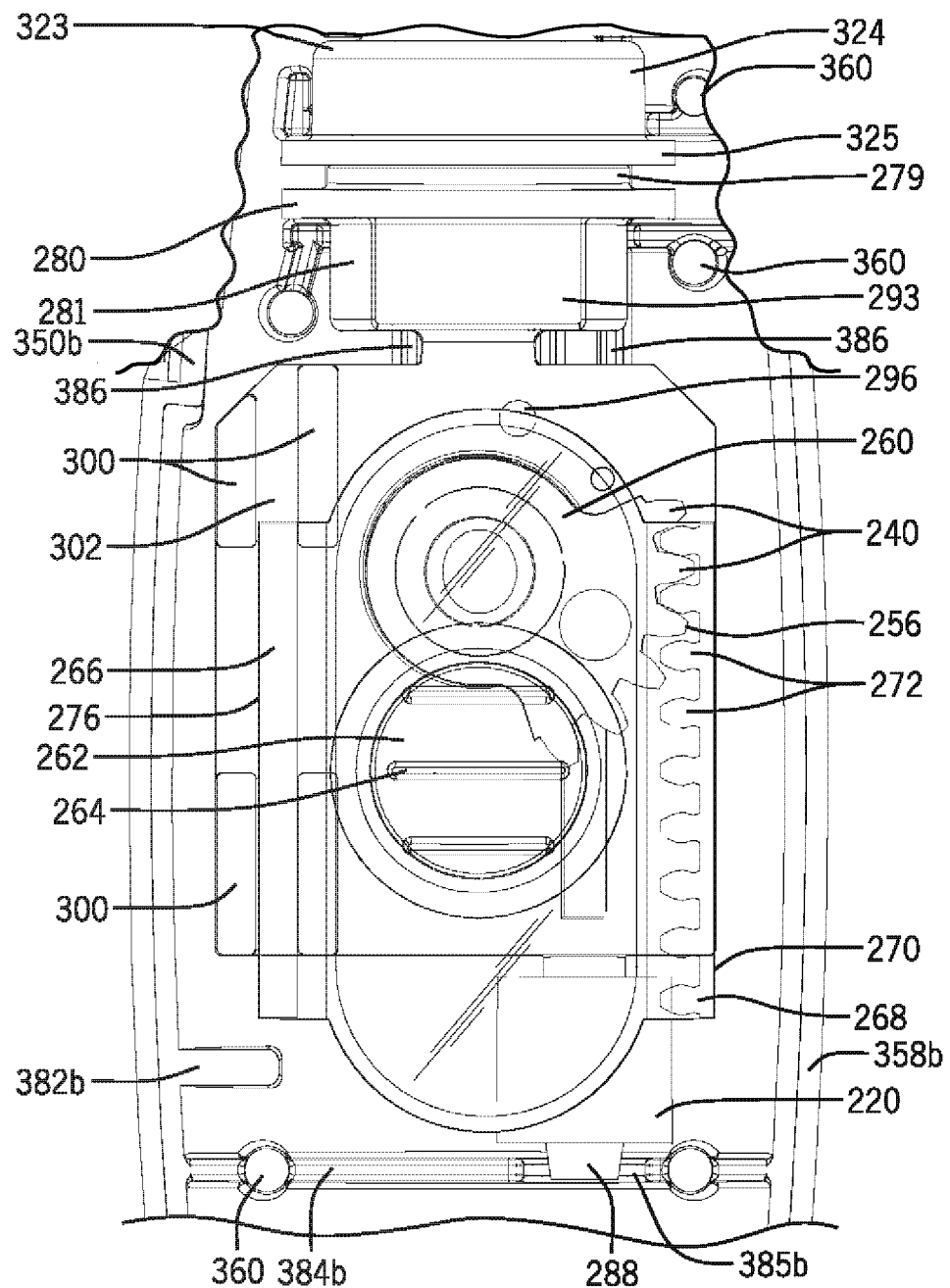
FIG. 13E is a sectional transparent view of the oral irrigator handle showing the pause mechanism.
Figure 13F:
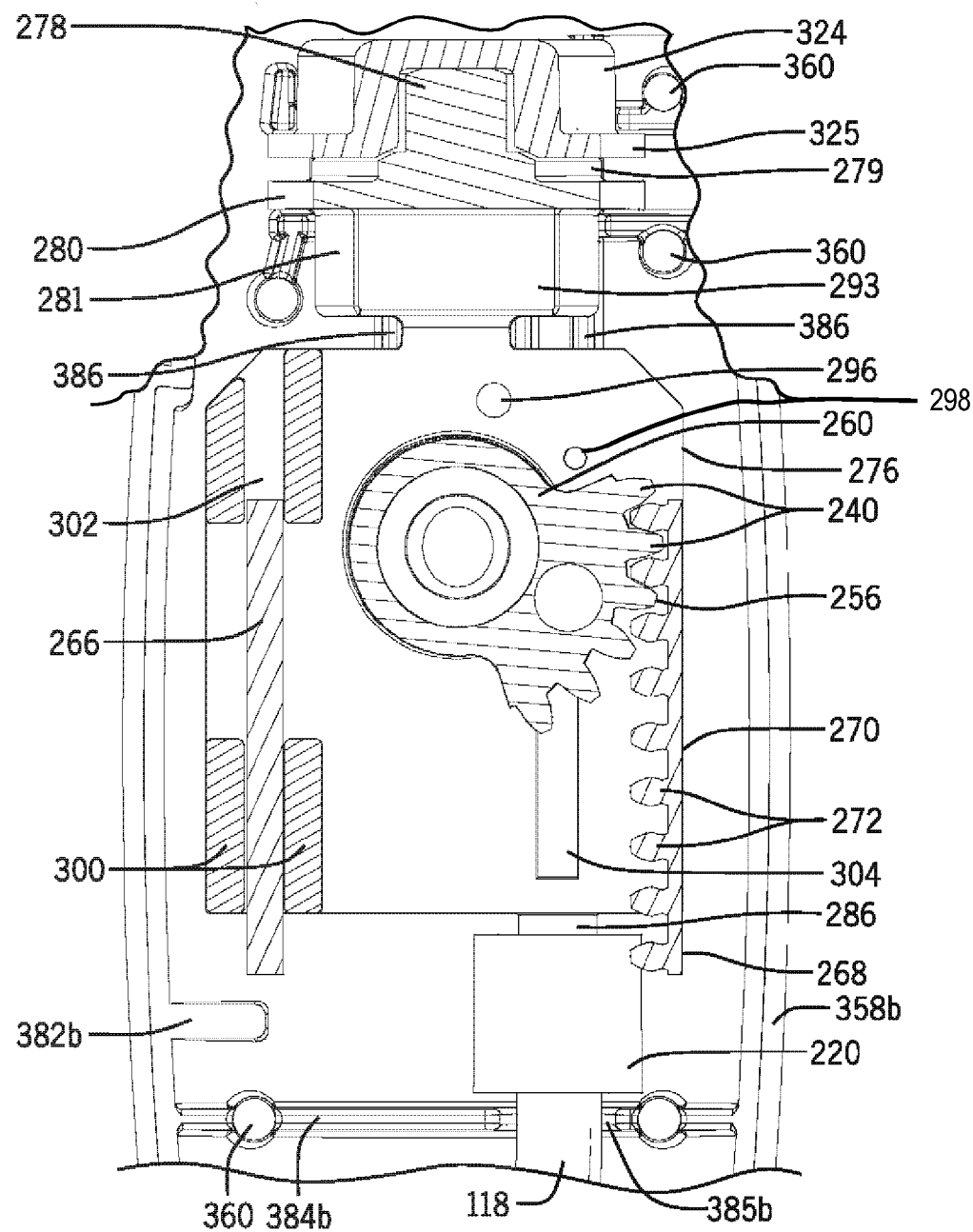
FIG. 13F is a sectional view of the cross-sectional view of FIG. 13C depicting the oral irrigator handle along line 13C-13C in FIG. 4.
Figure 13G:
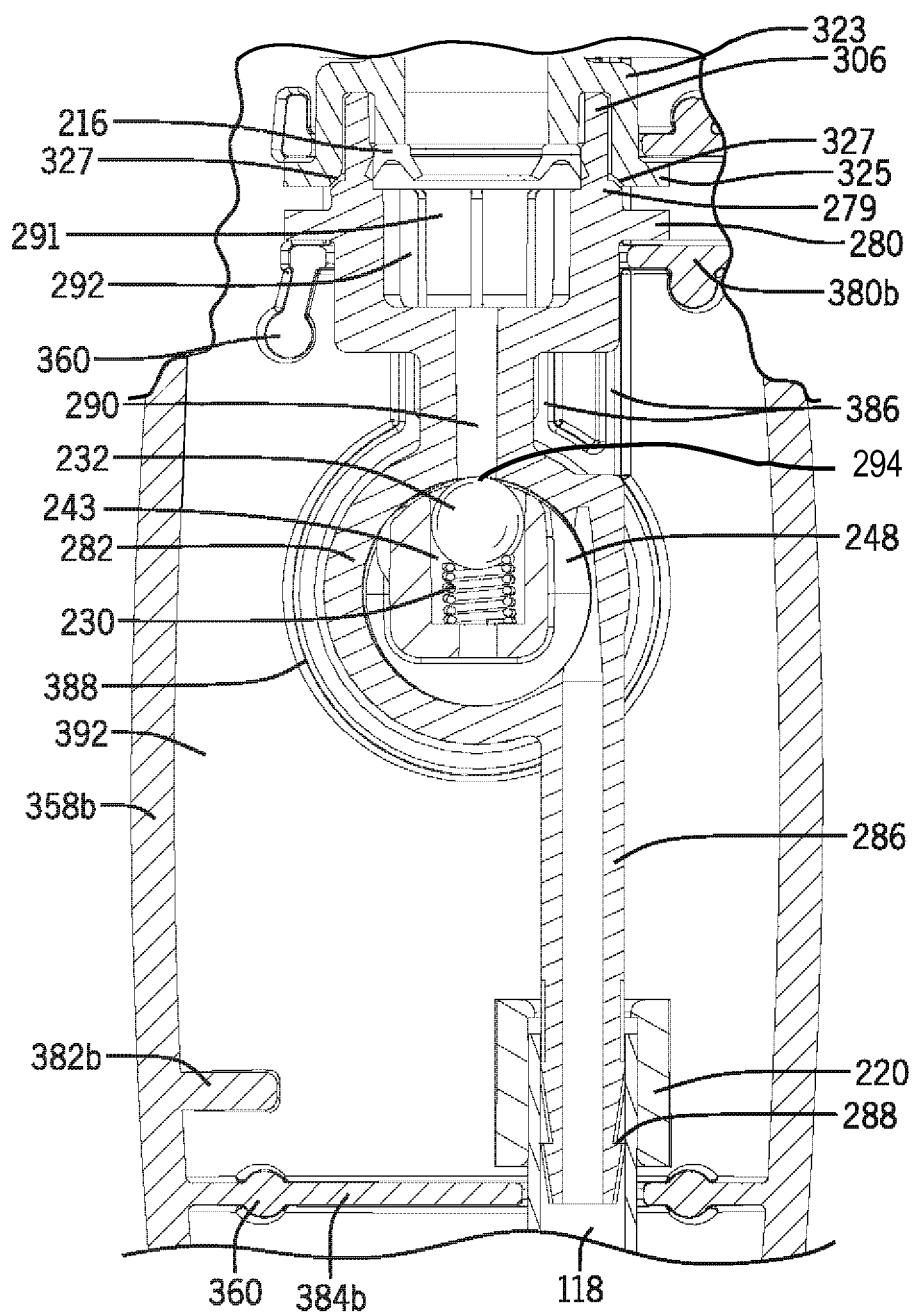
FIG. 13G is a sectional view of the cross-sectional view of the oral irrigator handle along line 13G-13G in FIG. 4.
Figure 13H:
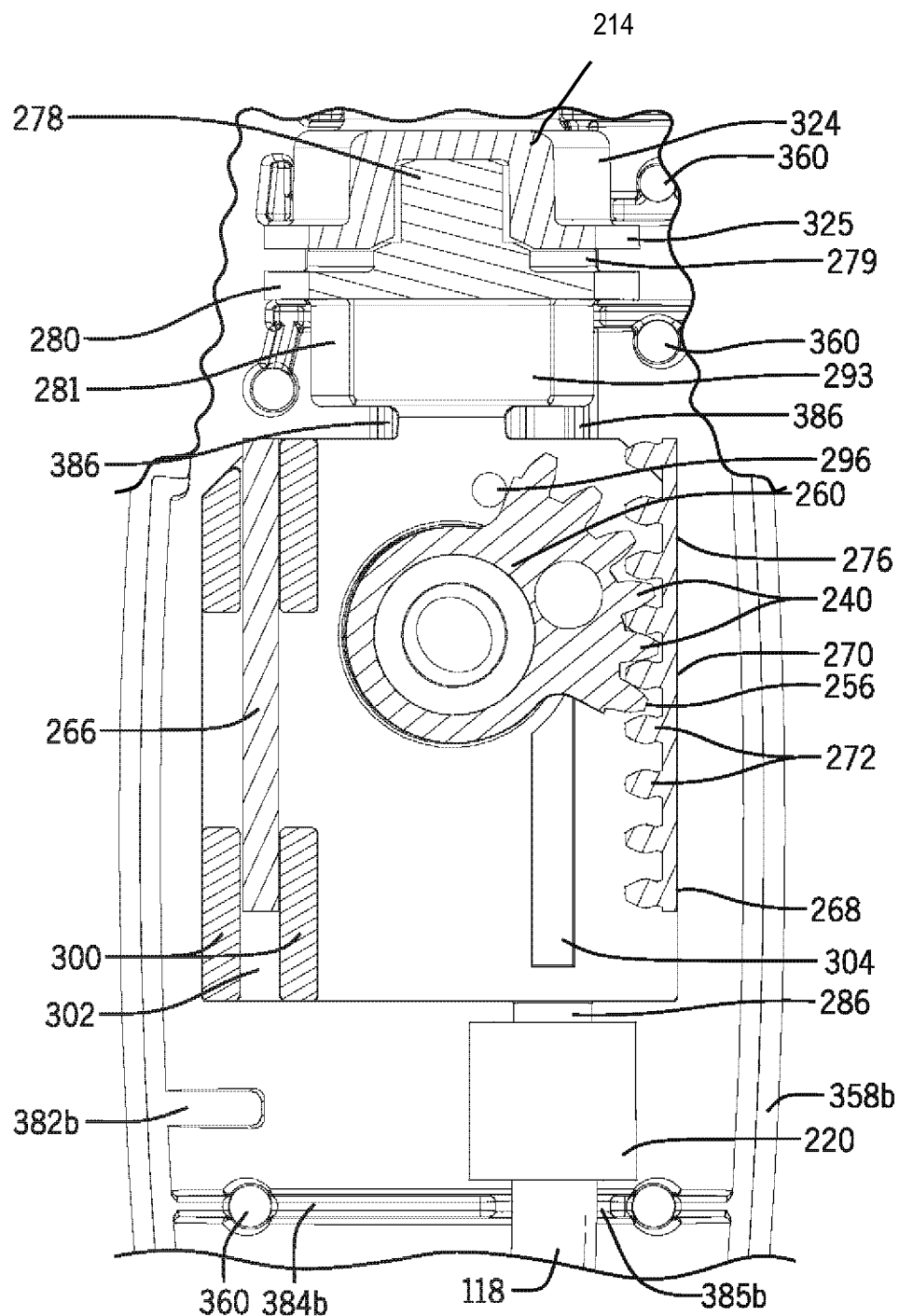
FIG. 13H is a sectional view of the cross-sectional view of FIG. 13C depicting the oral irrigator handle along line 13C-13C in FIG. 4.
Figure 13I:
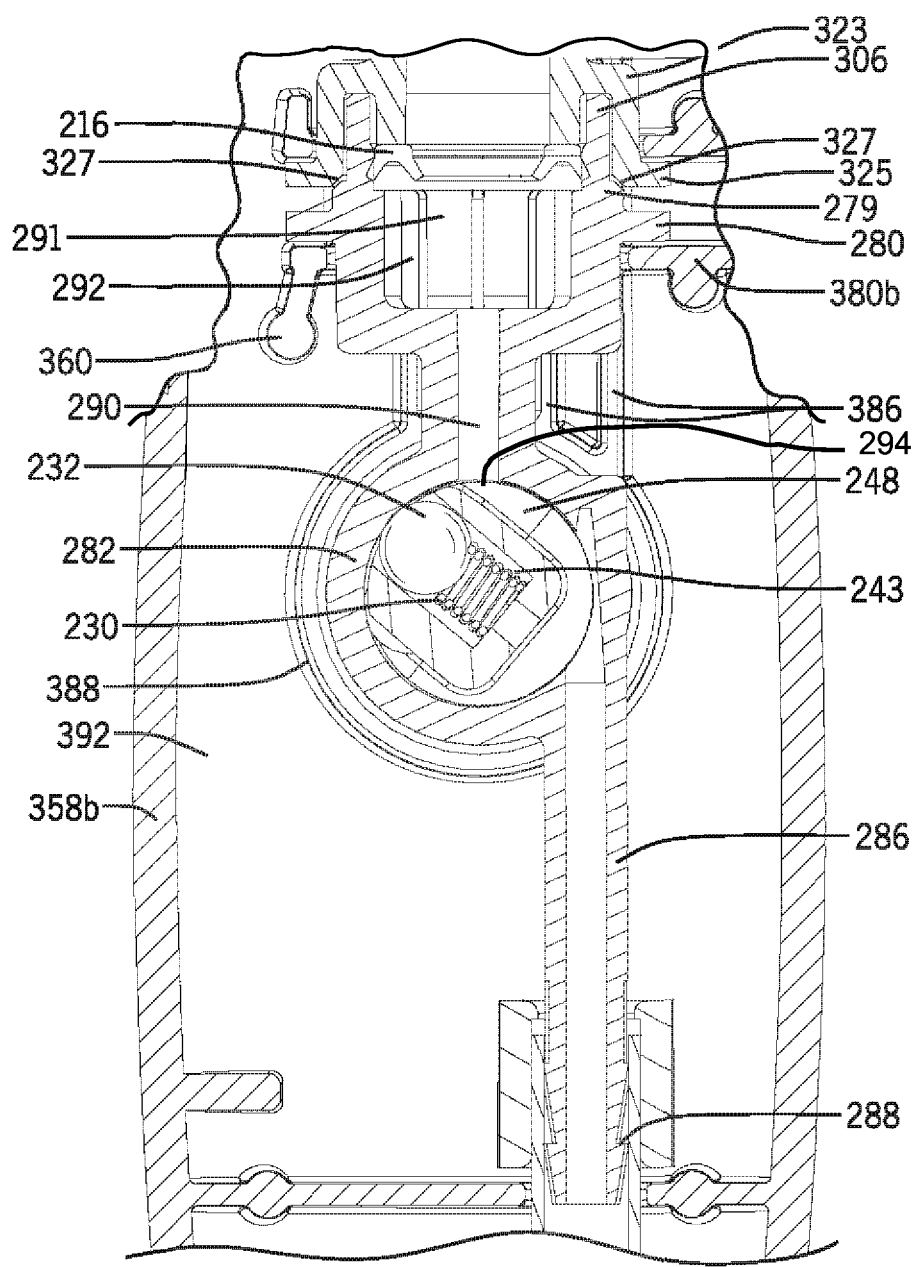
FIG. 13I is a sectional view of the cross-sectional view of the oral irrigator handle along line 13G-13G in FIG. 4.
Figure 14D:
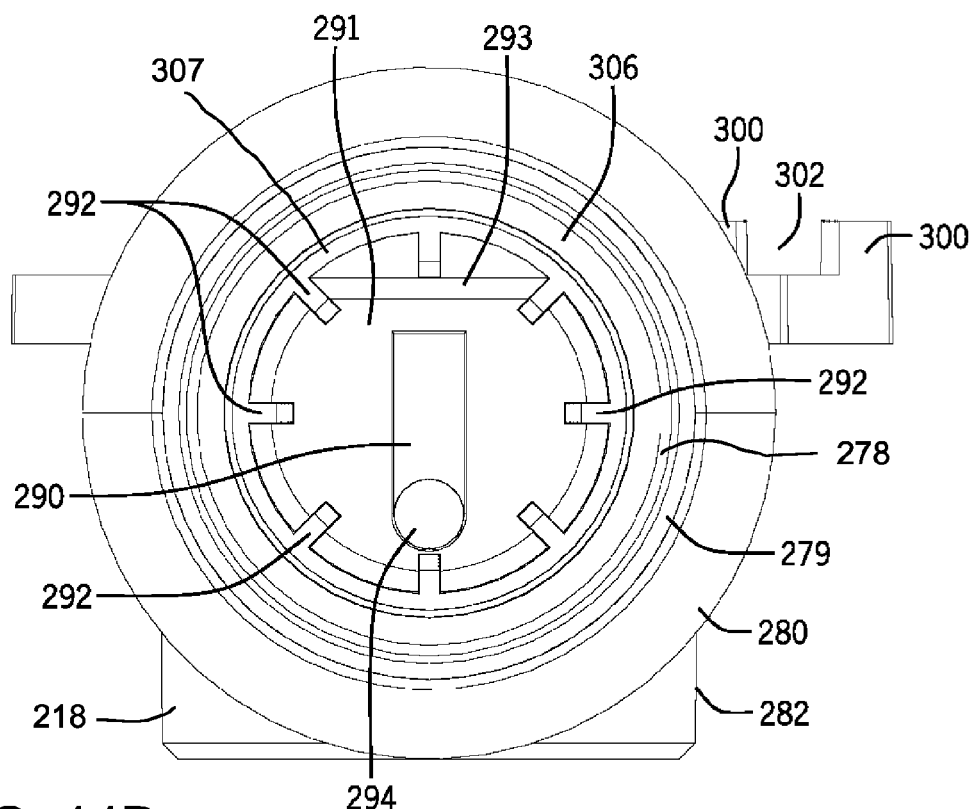
FIG. 14D is a top view of the valve body.
Figure 16A:
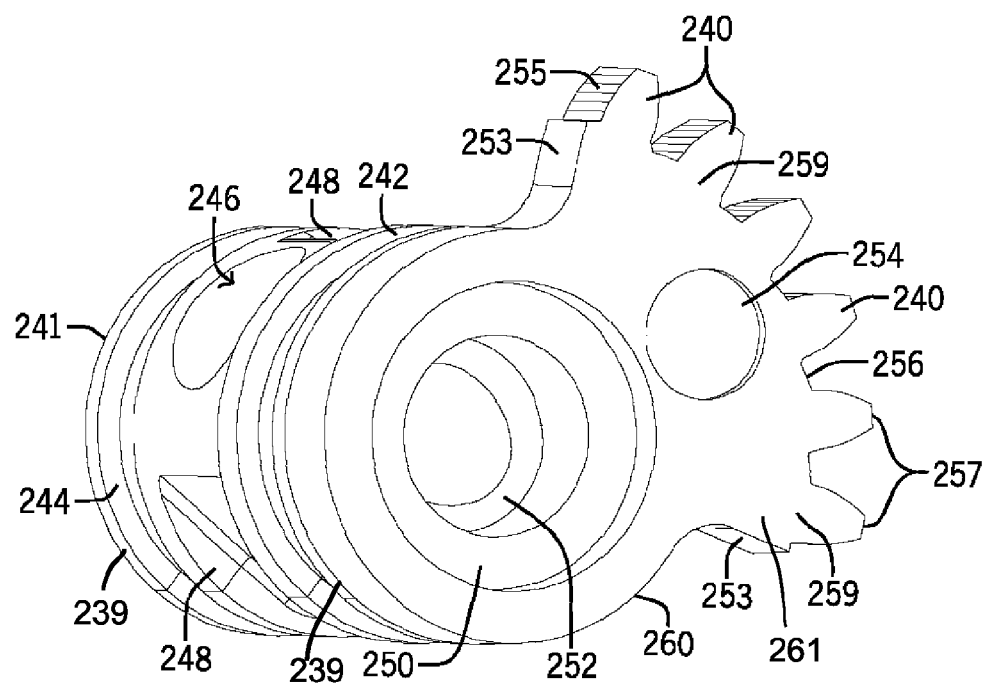
FIG. 16A is a perspective front view of the spool body.
Figure 16B:
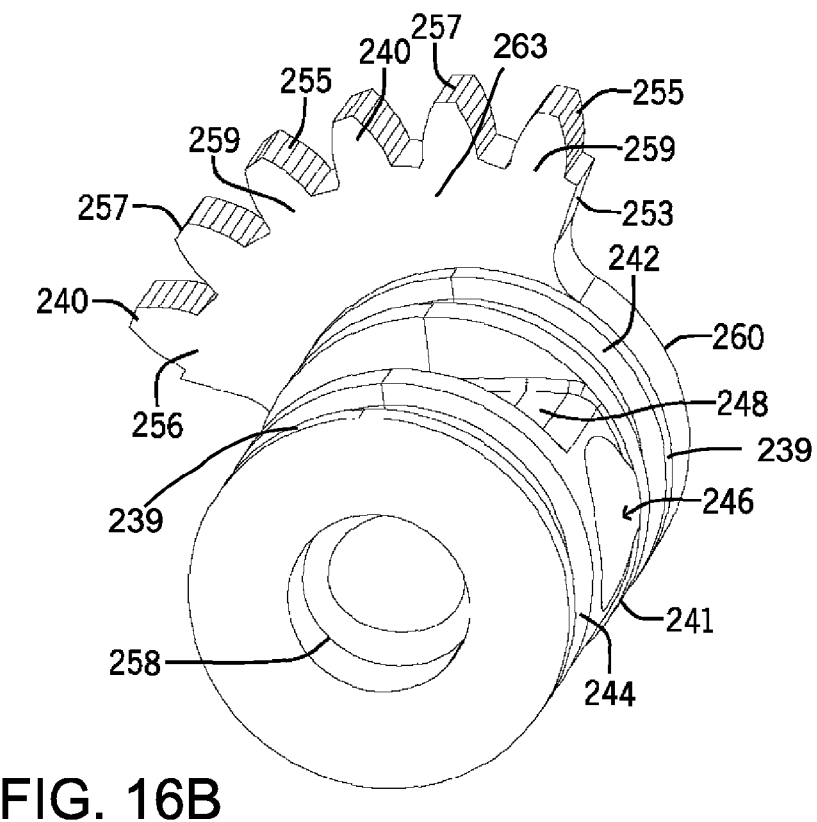
FIG. 16B is a perspective rear view of the spool body.
Figure 16C:
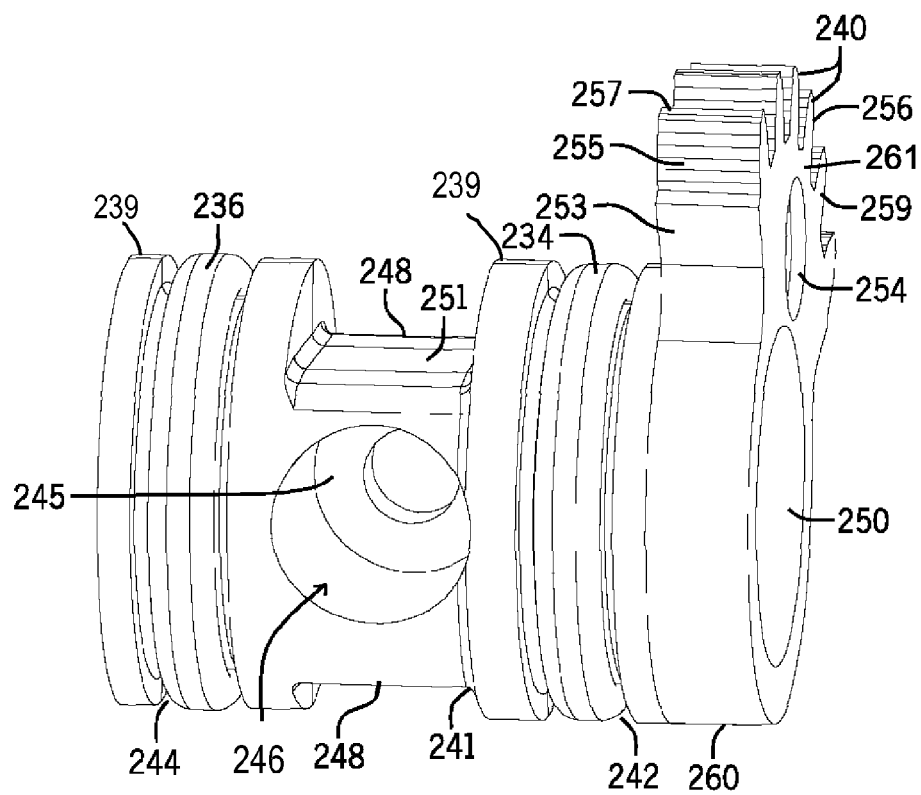
FIG. 16C is a left view of the spool body.
Figure 16D:
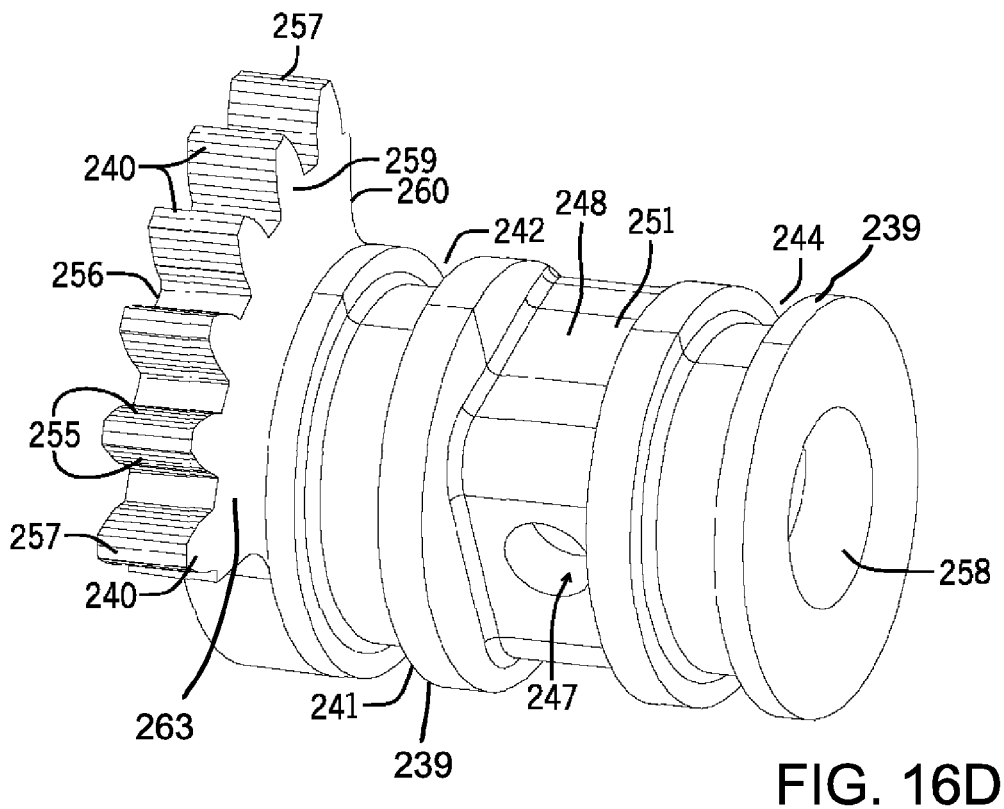
FIG. 16D is a right view of the spool body.

As shown in FIGS. 13G and 14C-D, the mouth 278 may define a cylindrical cavity. The tip receiving portion 281 positioned below the mouth 278 may be substantially cylindrical or, as depicted in FIG. 14B, may be squared off on one side by a front wall 293 to form a D-shaped cavity in the tip receiving portion 281. The tip receiving member 281 may also include interior ribs 292 extending radially inward from the curved walls of the tip receiving member 281 and for a length in a direction generally aligned with the longitudinal axis of the handle 200. An interior wall from which the ribs 292 extend that defines the cavity in the tip receiving portion 281 may be smaller in diameter than the mouth 278 and thereby form an annular ledge 307 between the mouth 278 and the tip receiving portion coterminous with the height of the ribs 292. A cup seal 216 may be positioned inside the mouth 278, above the tip-receiving portion 281, and proximate to the first rim 279. An outer edge of the cup seal 216 may be supported by the annular ledge 307.

A substantially keyhole-shaped well 290 may be formed in the neck 277 of the valve body 218. The well 290 may extend through the neck 277 between the fluid outlet 294 in the valve spool chamber 282 and the cavity defined in the tip-receiving portion 281 in the upper portion 275 of the valve body 218.

With reference to FIGS. 13A-I, when the handle 200 is assembled, the tip receiving member 281 is received in semicircular notches 381a, 381b of the sixth interior shelf 380a, 380b. The valve chamber 282 of the valve body 218 is positioned within or adjacent to the circular wall 388 and/or counterforts 389 of the second handle-housing segment 206. The second rim 280 is positioned above and adjacent to the sixth interior shelf 380a, 380b.

As shown in FIGS. 12 and 13A-I, a valve cap 214 may be positioned on top of the mouth 278 of the valve body 218. The valve cap 214 comprises a body 322 and a skirt 324. The body 322 is generally cylindrical in shape and comprises a cavity wall 328 that defines a first tip cavity 330 for receiving a tip 150. The skirt 324 may include an annular recess 326, a hip 323, a foot 325, and a heel 327. The hip 323 may have a circumference greater than the circumference of the body 322, and the foot 325 may have a still greater circumference than that of the hip 323, which may create a stepped outer surface of the valve cap 214. The annular recess 326 is configured to receive the wall 306 of the mouth 278 of the valve body 218. The first rim 279 of the valve body 218 is positioned under the heel 327 of the foot 325 of the valve cap 214.

Figure 10:
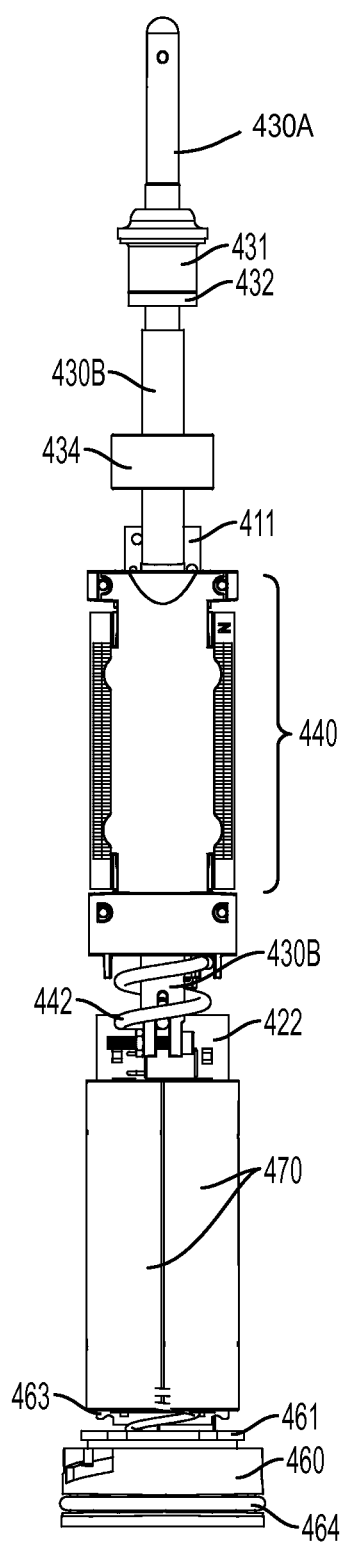
FIG. 10 is a rear partial view of the toothbrush depicted with the shell removed.
Figure 11:
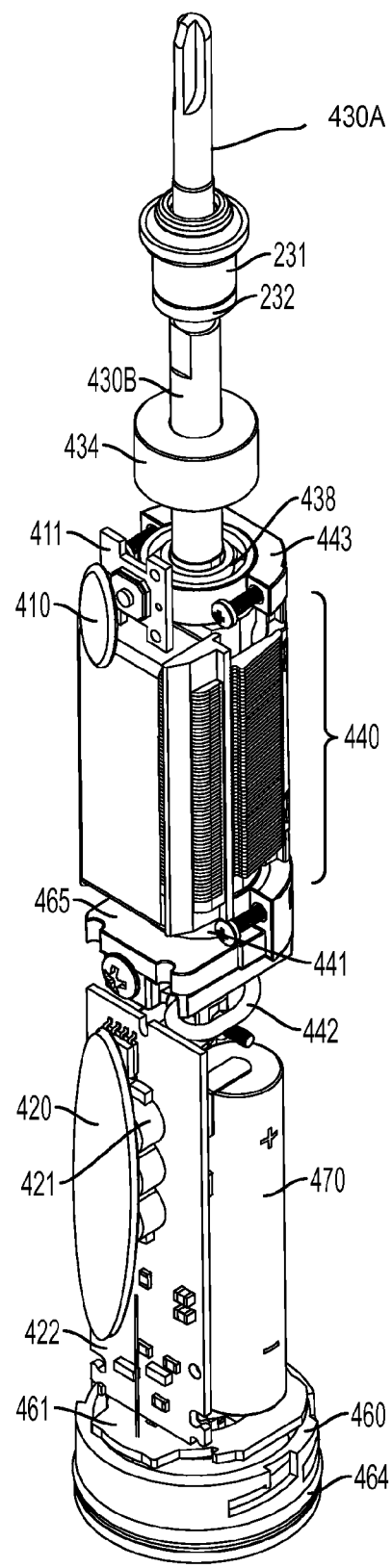
FIG. 11 is a perspective view of a front partial view of the toothbrush depicted with the shell removed.

In the embodiment depicted in FIG. 10, the cavity wall 328 terminates above the plane created by the foot 325 of the valve cap 214. In other embodiments, the cavity wall 328 may extend to or beyond the plane created by the foot 325 of the valve cap 214. When the handle 200 is assembled, the portion of the cavity wall 328 proximal to the foot 325 may be adjacent to the cup seal 216.

With reference to FIGS. 13A-I and 18A-B, when the handle 200 is assembled, the body 322 of the valve cap 214 may be received in semicircular notches. For example, the skirt 324 is received in semicircular notches 379a, 379b in the interior shelves 378a, 378b. Similarly, the foot 325 is positioned below, and may be retained by, the interior shelves 378a, 378b. The heel 327 of the foot 325 is positioned adjacent to the first rim 279 of the upper portion 275 of the valve body 218.

With reference to FIGS. 13A-I and 18A-B, when the handle 200 is assembled, the top of the latch 212 may be below and adjacent to the interior shelves 370a, 370b, and at least a portion of the bottom of the latch 212 may be adjacent to or rest upon the interior shelves 374a, 374b. As described above, the guide walls 320 of the latch body 308 may rest on the second interior shelves 370a,b, 374a,b.

With reference now to FIGS. 12 and 15A-15C, the handle 200 may also comprise a pause control actuator 226, which may include a button 262, a first flange 266, and a second flange 268. Although depicted in FIG. 15A as round with ribs 264 and raised from the face of the pause control actuator 226, the button 262 may be any size or shape, and have any texture that helps provide traction against a user's finger or hand. The face of each of the first and second flanges 266, 268 on the same side of the pause control actuator 226 as the button 262 may be substantially rectangular and flat.

With reference to FIGS. 15B and 15C, one of the flanges, such as the first flange 266, may have a substantially rectangular cuboid shape. The face of the opposing flange, i.e., the second flange 268, on the opposite side of the pause control actuator 226 as the button 262 includes a rack gear 270. The rack gear 270 comprises one or more rack gear teeth 272 that extend laterally in the direction of the first flange 266. Part or all of the edge 267 of each rack gear tooth 272 may be chamfered. The width of the base 271 of a rack gear tooth 272 may be wider than the tip 273 of that rack gear tooth 272. The width of one or both of the base 271 and tip 273 may be less than the width of that rack gear tooth 272 between the base 271 and the tip 273. The plane of a tip 273 may be flat and parallel to the plane of its base 271, as shown in FIGS. 15B and 15C, or the tip 273 may be rounded or pointed. Nine rack gear teeth 272 are depicted in the embodiment of FIGS. 15B and 15C, but any number of rack gear teeth 272 may be present. The rack gear teeth 272 may be substantially evenly spaced along the length of the rack gear 270.

In some embodiments, and as depicted in FIGS. 12, 16A-D, and 14, the handle 200 includes a valve gear assembly that comprises the pause control actuator 226, as described above, the valve spool 228, a ball spring 230, and a ball 232.

The valve spool 228, which may be a spool housing a ball valve, comprises at least a spool body 241 and a gear portion 260. The spool body 241 may have lateral cylindrical portions 239 that define annular recesses 242, 244, each for receiving an o-ring 234, 236 or other seal. The o-rings 234, 236 may help prevent fluid, including pressurized fluid, from leaking into the handle housing 202 along the interface of the spool body 241 and the valve chamber 282 of the valve body 218 when the spool body 241 is positioned inside the valve body 218, as described below.

A cylindrical cavity 246 may be formed in a sidewall of the spool body 241 between the cylindrical portions 239. An outer perimeter surface of the spool body 241 defining the cavity 246 is of the same diameter and follows the curvature of the cylindrical portions 239. An interior wall 245 may define a base of the cavity 246. The interior wall 245 may further define a central aperture 247 there through such that the interior wall 245 takes the form of an annular shelf in the base of the cavity 246. The central aperture 247 is smaller in diameter than the diameter of the cavity 246. The cavity 246 is configured to receive a second spring 230 and a ball 232, which may be a rubber or elastomeric ball 232.

When the valve gear assembly is assembled, the second spring 230 may be positioned adjacent to the interior wall 245. The ball 232 has a diameter at least marginally less than the diameter of the cavity 246 but greater than the diameter of the central aperture 247, and is positioned within the cavity 246 against the second spring 230.

The spool body 241 may also define a channel 248 conducting fluid. The channel 248 may be formed between the cylindrical portions 239. In the exemplary embodiment depicted in FIGS. 16A-16D, the channel 248 traverses approximately three quarters of the circumference of the spool body 241. The channel 248 does not traverse the cavity 246, but does traverse, and therefore intersect with, the central aperture 247. The channel 248 may have a flat base 251, or the base 251 may be curved along a shorter radius from the center axis of the spool body 241 than the radius of the cylindrical portions 239.

The spool body 241 may also include one or more recesses or cavities 250, 252, 254, 258, which may be substantially circular in shape and may have varying depths. In the exemplary embodiment, these recesses may be artifacts of the molding process, for example, to reduce wall thicknesses and provide uniform cooling of the molded material forming the spool body 241, but otherwise may not have any particular role with respect to the function of the valve spool 228.

The gear portion 260 of the valve spool 228 is positioned adjacent one of the cylindrical portions 239 and may be generally circular in shape with a radially extending, arcuate pinion gear 256. The pinion gear 256 may have an outer face 261 and an inner face 263. The pinion gear 256 comprises one or more pinion gear teeth 240 that extend generally radially away from the valve body 241 at one end. The arc of the pinion gear 256 may be bounded laterally by sidewalls 253. Part or all of the edges 255 of each pinion gear tooth 240 may be chamfered. The width of a base 259 of a pinion gear tooth 240 may be wider than a tip 257 of that pinion gear tooth 240. Each tip 257 may be flat and generally parallel to a plane of its base 259, as shown in FIGS. 16A-16D, or the tip 257 may be rounded or pointed. Six pinion gear teeth 240 are depicted in the embodiment of FIGS. 16A-16D, but any number of pinion gear teeth 240 may be provided. The pinion gear teeth 240 may be substantially evenly spaced along the arc-length of the pinion gear 256.

With reference to FIGS. 13A and 13E, when the handle 200 is assembled, the second spring 230 and ball 232 are inserted into the cavity 246 of the spool body 241 and o-rings 234, 236 are positioned in the annular recesses 242, 244 of the spool body 241. The spool body 241 may be inserted through the valve chamber aperture 283 and positioned within the valve chamber 282 of the lower portion 276 of the valve body 218. The o-rings 234, 236 create a fluid tight seal between the valve spool 228 and the valve chamber 282. The ball 232 may be positioned adjacent to the chamber wall 285, and the ball 232 may compress the second spring 230 against the interior wall 245 of the spool body 241 of the valve spool 228. The ball 232 is thus biased toward the chamber wall 285 to create a fluid-tight seal over the fluid outlet 294 in the valve body 218 when the ball 232 is positioned adjacent thereto.

The gear portion 260 of the valve spool 228 extends out of the aperture 283 in the valve body 218. The inner face 263 of the pinion gear 256 may be flush with the surface of the valve 218 body defining the apertures 283 and the teeth 240 of the pinion gear 256 may be oriented opposite and extend away from the walls 300 on the lower portion 276 of the valve body 218.

The first flange 266 of the pause control actuator 226 may be received in the slot 302 created by the walls 300 of the lower portion 276 of the valve body 218. The rack gear 270 of the pause control actuator 226 is operably associated with the pinion gear 256 of the gear portion 260 of the valve spool 228 via mating or interfacing of some or all of the rack gear teeth 272 with some or all of the pinion gear teeth 240.

When the handle 200 is assembled, and the pause control actuator 226 is moved upwards toward the collar 208, rotation of the pinion gear 256 is stopped when the button 262 of pause control actuator 226 contacts the first handle housing segment 204, and/or when the upper sidewall 253 of the pinion gear 256 contacts the post 296. When the pause control actuator 226 is moved downwards, sliding of the rack gear 270 is stopped when the button 262 contacts the first handle housing segment 204, and/or when the first flange 266 contacts the seventh interior shelf 382a, 382b.

Insertion and Ejection of a Tip into the Handle

By way of example, but not limitation, a user may insert a tip 150 into, and eject a tip 150 from, the handle 200 of the oral irrigator 5 of FIGS. 1-18 according to the following procedures.

A tip 150 is inserted into the handle 200 by passing a proximal end of the tip 150 through the first tip-receiving aperture 209 of the collar 208, through the tip receiving portions 341a, 341b of the first and second handle housing segments 204, 206, and into the tip-receiving aperture 319 of the latch body 308. Before the tip 150 enters the handle 200, the tip-receiving aperture 319 of the latch body 308 is partially offset from the first tip cavity 330 of the valve cap 214, which is positioned below the second tip-receiving aperture 319. The tip 150 engages the latch body 308 and pushes the lip 318 of the latch body 308 laterally in the direction of the spring 310 until the tip-receiving aperture 319 of the latch body 308 and the first tip cavity 330 of the valve cap 214 vertically align. The spring 310 is compressed and is positioned adjacent to the side wall 313.

The proximal end of the tip 150 can then proceed through the first tip cavity 330 of the valve cap 214, past the cup seal 216, and into the second tip cavity 291 of the tip receiving member 281 of the upper portion 275 of the valve body 218. The well 290 may help fluid to flow into a tip 150 even when the fluid outlet 294 is not positioned directly below the fluid inlet of the tip 150. For example, as shown in FIG. 14D, the fluid outlet 294 is positioned off-center in the neck 277, but the well 290 transfers the fluid flow into the center of the cavity in the tip receiving portion 281 and thus under the fluid inlet of the tip 150. The outer diameter of the proximal end of the tip 150 is slightly larger than the inner diameter of the cup seal 216, thereby creating a fluid-tight seal between the cup seal 216 and the tip 150. The D-shape of the perimeter of the first interior walls 318 of the latch body 308, and the shape of the interior surface of the tip receiving member 281, either or both of which are complimentary or keyed to the D-shape of the proximal end of the tip 150, help to align the tip 150 in the handle 200. The tip 150 may also be aligned with and/or supported by the interior ribs 292 of the tip receiving member 281. The tip 150 may be coupled to the latch 212 by capturing the lip 318 of the latch body 308 within an annular recess (not shown) of the tip 150.

The collar 208 of the handle 200 is depressed toward the bodies 340a, 340b of the first and second handle housing segments 204, 206 when the tip 150 is coupled with the latch 212. As the collar 208 is depressed, the finger 345 of the collar 208 moves along the necks 342a, 342b of the first and second handle housing segments 204, 206 toward the bodies 340a, 340b, which decreases the height of the gap 347, as the first spring 210 is compressed. The compressed first spring 210 exerts an upward force, which will return the collar 208 back to its original position (i.e., separated from the bodies 340a, 340b by a gap 347) in the absence of another force opposing this upward force. When the tip 150 is coupled with the latch 212, this upward force will be opposed by a channel 151 on the tip 150 that holds the collar 208 down, thereby maintaining the collar 208 in a position adjacent the handle housing 202.

An audible click or other similar noise may occur when the latch 212 captures the annular recess 151 of the tip 150, thereby providing an audible indication that the tip 150 is attached to the handle 200. The noise may be mechanically produced (for example, a click resulting from a portion of the tip 150 impacting a portion of the handle 200, or a click resulting from a portion of the tip 150 springing outward or mechanically deforming).

In another example of inserting a tip 150, a user slides the tip eject button 238 laterally towards the spring 310. The second tip-receiving aperture 319 of the latch body 308 is thus aligned over the first tip cavity 330 of the valve cap 214 before the tip 150 is inserted. The inserted tip 150 can then proceed into the second tip cavity 291 as described above. The force on the button 238 forces the latch 212 to move laterally in the direction of the spring 310. The lip 318 disengages from the annular recess 151 in the tip 150 and the tip 150 is decoupled. The spring force of the first spring 210 on the collar 208 helps to eject the tip 150 by forcing the collar 208 upward against the flange 152 of the tip 150.

As noted, when the tip 150 is decoupled, the force opposing the upward force exerted by the first spring 210 is removed, thereby allowing the first spring 210 to move the collar 208 back to its original position. This movement of the collar 208 from a position adjacent to the bodies 340a, 340b to its original position provides a visual indication that the tip 150 has been decoupled from the latch 212.

Operation of the Oral Irrigator

By way of example, but not limitation, a user may use the oral irrigator 5 and components of FIGS. 1-17 for oral irrigation and/or cleaning of the teeth, gums, and tongue according to the following procedure.

Once a tip 150 is connected to the handle 200 as described above, and the reservoir 20 is filled and connected to the base 10, the reservoir valve is opened and the oral irrigator 5 can be used. To activate the oral irrigator 5, the use selects the first control actuator 40, which provides power to the motor to activate the pump. The pump pulls fluid from the reservoir 20 and forces it through the tube connector 125 into the tube 110.

Fluid flows through the tube 110 into the first fluid inlet 289 in the terminus of the barbed tip 288, and through the fluid conduit 286 of the valve body 218 towards the second fluid inlet 284 in the valve chamber 282 of the lower portion 276 of the valve body 218.

When the valve spool 228 is in the open position, fluid flows from the second fluid inlet 284 into and around the channel 248 of the spool body 241. From the channel 248, fluid flows into the fluid outlet 294 in the valve chamber 282, and into the well 290 that extends between the fluid outlet 294 and the tip receiving portion 281 in the upper portion 275 of the valve body 218. Fluid can then enter the proximal end of the tip 150, which is positioned in the second tip cavity 291 of the tip receiving portion 281, and exit the tip outlet 122 into the user's mouth.

During use, the user may select one or more of the second, third, and pause control actuators 110, 113, 226 on the oral irrigator 5 or handle 200 to vary one or more characteristics of the fluid flow output from the tip 150. For example, the second control actuator 110 may be selected to vary fluid pressure of the fluid as it exits the tip 150 or the third control actuator 113 may be selected to activate a massage mode.

Irrigate Mode and Pause Mode

During irrigate mode, fluid flows to the tip 150 as described above when the valve gear assembly is placed in an open position as follows (see FIGS. 13A-I). When the pause control actuator 226 including the rack gear 270 is positioned toward the collar 208 (i.e., in the up or on position), the pinion gear 256 of the gear portion 260 of the valve spool 228, which is operably connected to the rack gear 270, is moved to a position proximate to the post 296 and covers the aperture 298. In this position of the valve spool 228, the cavity 246 of the spool body 241 is positioned such that the ball 232 is not pressed against the fluid outlet 294 and therefore does not block the path of fluid through the valve body 218. The channel 248 of the spool body 241 is positioned such that it fluidly connects the second fluid inlet 284 in the valve chamber 282 of the lower portion 276 of the valve body 218 to the fluid outlet 294 in the valve chamber 282.

During pause mode, no, or very little, fluid flows into or out of the tip 150. To initiate pause mode without turning off power to the oral irrigator 5, the valve gear assembly is moved to a closed position as follows (see FIGS. 13A-I). A user manually slides the pause control actuator 226 downward by sliding the button 262 away from the collar 208 (i.e., in the down or off position), which also slides the rack gear 270 downward. Translational movement of the rack gear 270 is converted to rotational movement of the operably associated pinion gear 256 via the interlocked rack gear teeth 272 and pinion gear teeth 240. The pinion gear 256 is thus rotated clockwise away from the post 296, which rotates the operably connected spool body 241, including the cavity 246. The ball 232 in the cavity 246 is thus brought into a position below the fluid outlet 294. The ball 232 partially or completely covers the fluid outlet 294, which partially or completely blocks fluid from flowing into the fluid outlet 294 and thereby pauses or stops fluid flow through the valve body 218 to the tip 150.

While fluid flow is paused, the force of the compressed second spring 230 against the ball 232 helps to maintain the ball 232 securely positioned against the fluid outlet 294 and helps the ball 232 create a fluid-tight seal. Fluid may enter the cavity 246 beneath the ball 232 through the central aperture 247 in the interior wall 245. Fluid pressure against the ball 232 may also help to maintain the ball 232 securely positioned against the fluid outlet 294.

The pause mode is selected by mechanical, not electrical, operation of the pause control actuator 226. A mechanically selectable pause mode avoids the need for electrical circuitry in the handle 200, which thereby helps improve the safety of the handle 200 and the oral irrigator 5 because electrical circuits are not in close physical proximity to fluid conduits. A mechanically instead of an electrically controlled pause mode also decreases the manufacturing cost of the handle 200 and the oral irrigator 5. No separate battery is required in the handle 200 to power such circuits. Alternatively, the handle 200 need not be electrically wired to the base unit of the oral irrigator 5. Thus, an easily accessible and selectable pause mode is provided to the user with significantly less manufacturing cost and greater safety.

Other Examples of the Combination Oral Hygiene Device

FIGS. 19-25 illustrate various views of another example of the oral hygiene device. In the example shown in FIGS. 19-25, the lid of the device includes lips or tabs that extend further outwards from the edge of the lid past the reservoir to provide an increased gripping surface for a user to grasp and lift the lid. Additionally, the grip pads extending on opposing lateral sides of the toothbrush body are larger and extend further along the length of the toothbrush than in the example of the oral hygiene device shown in FIG. 1. The extended length and size of the grip pads provides for increased comfort and gripping for the user while the user is holding the toothbrush and also allows for users with a variety of hand sizes, such as those with large hands, to use the toothbrush with increased comfort.

CONCLUSION

All directional references (e.g., upper, lower, upward, downward, left, right, leftward, rightward, top, bottom, above, below, vertical, horizontal, clockwise, and counterclockwise) are only used for identification purposes to aid the reader's understanding of the embodiments of the present invention, and do not create limitations, particularly as to the position, orientation, or use of the invention unless specifically set forth in the claims. Joinder references (e.g., attached, coupled, connected, joined, and the like) are to be construed broadly and may include intermediate members between a connection of elements and relative movement between elements. As such, joinder references do not necessarily infer that two elements are directly connected and in fixed relation to each other.

In some instances, components are described with reference to "ends" having a particular characteristic and/or being connected with another part. However, a person skilled in the art will recognize that the present invention is not limited to components which terminate immediately beyond their points of connection with other parts. Thus, the term "end" should be interpreted broadly, in a manner that includes areas adjacent, rearward, forward of, or otherwise near the terminus of a particular element, link, component, part, member or the like. In methodologies directly or indirectly set forth herein, various steps and operations are described in one possible order of operation, but those skilled in the art will recognize that steps and operations may be rearranged, replaced, or eliminated without necessarily departing from the spirit and scope of the present invention. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A dental hygiene apparatus comprising
    a base housing including a toothbrush receptacle formed as a contiguous part of the base housing;
    a reservoir having a volume for holding a fluid mounted on the base housing;
    a pump system enclosed within the base housing and in fluid communication with the reservoir, the pump system comprising
        a high voltage direct current motor;
        a helical pinion gear connected to the high voltage direct current motor;
        a helical driven gear in meshed engagement with the helical pinion gear;
        an eccentric bushing mounted on a top surface of the helical driven gear; and
        a plunger operably connected to the eccentric bushing;
    an oral irrigation handle with a removable tip fluidly connected to the pump system via a tube;
    a toothbrush removably positioned within the toothbrush receptacle; and
    an accessory storage container connected to the base housing and positioned adjacent the reservoir; wherein activation of the high voltage direct current motor causes rotation the helical pinion gear, which in turn drives the helical driven gear, and causes the plunger to selectively pump the fluid from the reservoir to the tube and out the removable tip.

2. The dental hygiene apparatus of claim 1, further comprising
    a first lid pivotably movable relative to the accessory storage container; and
    a second lid removably connected to and covering the reservoir.

3. The dental hygiene apparatus of claim 1, wherein the toothbrush is a sonic toothbrush driven by a motor located within a housing of the toothbrush.

4. The dental hygiene apparatus of claim 1, wherein the toothbrush receptacle further comprises
    a support collar for supporting the toothbrush within the receptacle; and
    an inductive coil operable to charge a rechargeable battery within the toothbrush.

5. The dental hygiene apparatus of claim 4, further comprising a power source in electrical communication with the high voltage direct current motor and with the inductive coil.

6. The dental hygiene apparatus of claim 1, wherein the oral irrigation handle includes a sliding pause switch which translates longitudinal motion into a rotational motion which engages and disengages a valve internal to the handle.

7. The dental hygiene apparatus of claim 1, wherein the oral irrigation handle includes a tip retention aperture located below a spring loaded head portion, wherein the spring loaded head portion forces the tip against the tip retention aperture.

8. The dental hygiene apparatus of claim 7, wherein the tip retention aperture slides transversely across the handle and engages a retention groove in the tip.

9. The dental hygiene apparatus of claim 1, further comprising a lid with at least one ventilation aperture located in the lid for ventilating the accessory storage container when the lid is in a closed position.

10. The dental hygiene apparatus of claim 9, wherein the accessory storage container and the lid define a substantially enclosed volume for storing at least one item, wherein the lid includes at least one hinged position.

11. The dental hygiene apparatus of claim 10, wherein when the lid is in a closed position a gap is defined between a bottom surface of the lid and a top edge of the accessory storage container.

12. The dental hygiene apparatus of claim 10, wherein the accessory storage container includes walls formed therein that are configured to receive and retain a tip therein.

13. The dental hygiene apparatus of claim 1, wherein the pump system is powered by a power cord routed through a channel on a bottom surface of the base housing.

14. The dental hygiene apparatus of claim 13, wherein the cord is supported by internal strain relief comprising a strain relief with a plurality of walls that protrude into the channel.

15. The dental hygiene apparatus of claim 13, further comprising a gear housing that houses the helical pinion gear and the helical driven gear, wherein the high voltage direct current motor is located above the gear housing and a motor shaft passes through the gear housing and into the helical pinion gear.

16. The dental hygiene apparatus of claim 15, wherein the gear housing includes an aperture that the plunger passes through and into a cavity of the base housing that encloses the pump and the high voltage direct current motor.

17. The dental hygiene apparatus of claim 16, wherein
    the cavity of the base housing receives the pump and high voltage direct current motor so as to enclose the pump and high voltage direct current motor within the base housing; and
    the gear housing includes an interior cavity into which the plunger extends via the aperture defined in the gear housing, wherein the interior cavity of the gear housing is sealed from the cavity of the base housing by an elastomer seal that contacts the gear housing and surrounds the plunger.

18. The dental hygiene apparatus of claim 17, wherein the elastomer seal is a water resistant barrier that limits contamination of the water utilized in the dental hygiene apparatus by contents of the gear housing.

19. The dental hygiene apparatus of claim 16, further comprising a drain hole located in a lower chassis that forms a bottom of the gear housing and separates the interior cavity of the gear housing from a bottom plate of the base housing, wherein the drain hole is operable to evacuate liquid and debris within the gear housing to an exterior of the base housing.

* * * * *